(12) United States Patent
Kawanishi

(10) Patent No.: US 7,541,131 B2
(45) Date of Patent: Jun. 2, 2009

(54) RESIST COMPOSITION, COMPOUND FOR USE IN THE RESIST COMPOSITION AND PATTERN FORMING METHOD USING THE RESIST COMPOSITION

(75) Inventor: Yasutomo Kawanishi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/356,048

(22) Filed: Feb. 17, 2006

(65) Prior Publication Data

US 2006/0194147 A1 Aug. 31, 2006

(30) Foreign Application Priority Data

Feb. 18, 2005 (JP) .......................... P.2005-042328
Aug. 31, 2005 (JP) .......................... P.2005-252611

(51) Int. Cl.
G03F 7/039 (2006.01)
G03F 7/038 (2006.01)

(52) U.S. Cl. .................... 430/270.1; 548/100; 526/256; 526/257; 549/12; 549/27; 549/26; 540/491; 544/5; 522/904; 522/31; 522/9; 522/15; 522/25; 430/922; 430/905; 430/910; 430/296; 430/326; 430/325; 430/330

(58) Field of Classification Search ................. 548/100; 526/256, 257; 549/12, 27, 26; 540/491; 544/5; 522/904, 31, 9, 15, 25
See application file for complete search history.

(56) References Cited

U.S. PATENT DOCUMENTS

| | | | | |
|---|---|---|---|---|
| 3,779,778 | A * | 12/1973 | Smith et al. | 430/270.1 |
| 4,090,936 | A * | 5/1978 | Barton | 430/280.1 |
| 4,318,766 | A * | 3/1982 | Smith | 156/330 |
| 4,491,628 | A * | 1/1985 | Ito et al. | 430/176 |
| 4,694,029 | A | 9/1987 | Land | |
| 4,708,925 | A * | 11/1987 | Newman | 430/270.1 |
| 5,045,431 | A * | 9/1991 | Allen et al. | 430/270.1 |
| 6,004,721 | A * | 12/1999 | Tan et al. | 430/270.1 |
| 6,548,221 | B2 | 4/2003 | Uetani et al. | |
| 6,680,157 | B1 | 1/2004 | Fedynyshyn | |
| 6,787,281 | B2 * | 9/2004 | Tao et al. | 430/163 |
| 2004/0067433 | A1 * | 4/2004 | Nirmal et al. | 430/270.1 |
| 2005/0015865 | A1 | 1/2005 | Chaix et al. | |

FOREIGN PATENT DOCUMENTS

| | | |
|---|---|---|
| EP | 1480078 A1 | 11/2004 |
| JP | 2003-149800 A | 5/2003 |
| JP | 2004-4557 A | 1/2004 |
| WO | WO-03/072567 A1 * | 9/2003 |

OTHER PUBLICATIONS

Allen et al "High performance acrylic polymers for chemically amplified photoresist applications", J.Vac. Sci. Technol. B 9 (6), Nov./Dec. 1991, pp. 3357-3361.*
Allen et al , "193 nm Single Layer Positive Resists Building Etch Resistance Into a High Resolution Imaging System", Proceedings of SPIE, vol. 243, Jun. 1995, pp. 474 to 485.*

* cited by examiner

*Primary Examiner*—Cynthia Hamilton
(74) *Attorney, Agent, or Firm*—Sughrue Mion, PLLC

(57) ABSTRACT

The invention provides a resist composition for use in the production process of a semiconductor such as IC, in the production of a circuit substrate of liquid crystal, thermal head and the like or in other photofabrication processes, a compound for use in the resist composition and a pattern forming method using the resist composition, which are a resist composition comprising (A) a sulfonium salt represented by the following formula (I); and a pattern forming method using the resist composition:

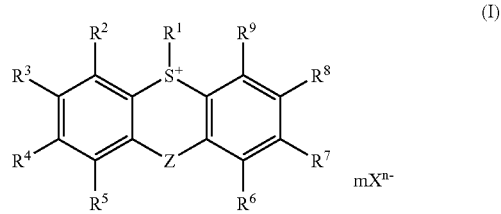

wherein
$R^1$ represents an alkyl group or an aryl group,
$R^2$ to $R^9$ each independently represents a hydrogen atom or a substituent and may combine with each other to form a ring,
Z represents an electron-withdrawing divalent linking group,
$X^{n-}$ represents an n-valent anion,
n represents an integer of 1 to 3, and
m represents the number of anions necessary for neutralizing the electric charge.

20 Claims, 1 Drawing Sheet

RESIST COMPOSITION, COMPOUND FOR USE IN THE RESIST COMPOSITION AND PATTERN FORMING METHOD USING THE RESIST COMPOSITION

BACKGROUND OF THE INVENTION

1. Field of the Invention

The present invention relates to a resist composition capable of changing in the properties by undergoing a reaction upon irradiation of actinic rays or radiation (e.g., electron beam, X-ray, EUV, UV), a compound for use in the resist composition and a pattern forming method using the resist composition. More specifically, the present invention relates to a resist composition for use in the process of producing a semiconductor such as IC, in the production of a circuit board for liquid crystal, thermal head and the like, in other photofabrication processes, or in a lithographic printing plate or an acid-curable composition, and also relates to a compound for use in the resist composition and a pattern forming method using the resist composition.

2. Background Art

A chemical amplification resist composition is a pattern forming material of forming a pattern on a substrate by producing an acid in the exposed part upon irradiation of radiation such as far ultraviolet light, and changing the solubility in a developer of the part irradiated with actinic radiation and the non-irradiated part resulting from a reaction using the generated acid as the catalyst.

In the case of using a KrF excimer laser as the exposure light source, a good pattern with high sensitivity and high resolution is formed because a resin exhibiting small absorption mainly in the 248-nm region and having poly(hydroxystyrene) as the basic skeleton is used as the main component, and this is a good system as compared with the conventional naphthoquinone diazide/novolak resin system.

On the other hand, in the case where a light source at a shorter wavelength, for example, an ArF excimer laser (193 nm) is used as the exposure light source, even the above-described chemical amplification system is not satisfied because the compound having an aromatic group inherently exhibits large absorption in the 193-nm region.

Therefore, development of a resist for an ArF excimer laser, containing a resin having an alicyclic hydrocarbon structure, is proceeding.

As for the acid generator which is a principal constituent component of the chemical amplification resist, a triphenylsulfonium salt is generally known (see, for example, Patent Document 1: U.S. Pat. No. 6,548,221).

However, this acid generator still has many insufficient points, and a resist composition enhanced in the sensitivity and the like is demanded.

Also, in the case of using a light source of emitting an electron beam, X-ray, EUV or the like, the exposure is performed in a vacuum and therefore, the outgas problem that a low boiling point compound such as solvent or a resist material decomposed due to high energy volatizes and contaminates the exposure apparatus, becomes important. Various studies are recently proceeding for the reduction of the outgas and various techniques have been attempted, for example, a technique of providing a topcoat layer to suppress the volatilization of a low molecular compound (see, for example, Patent Document 2: European Patent 1,480,078) or a technique of adding a radical trapping agent for suppressing the decomposition of a polymer (see, for example, Patent Document 3: U.S. Pat. No. 6,680,157). Thus, effort for reducing the outgas is demanded also in terms of the acid generator.

In Patent Documents 4 and 5 (JP-A-2003-149800 (the term "JP-A" as used herein means an "unexamined published Japanese patent application") and JP-A-2004-4557) or the like, a new acid generator is introduced.

On the other hand, a case of using a sulfonium salt having a specific structure in a photopolymerization composition containing an epoxy compound or the like is introduced in Patent Document 6: U.S. Pat. No. 4,694,029.

SUMMARY OF THE INVENTION

An object of the present invention is to provide a resist composition excellent in the sensitivity and outgassing properties, and a pattern forming method using the resist composition.

The present invention includes the following constitutions, whereby the above-described object of the present invention is attained.

(1) A resist composition comprising (A) a sulfonium salt represented by the following formula (I):

$$
\begin{array}{c}
R^2 \quad R^1 \quad R^9 \\
R^3 \diagdown \diagup S^+ \diagdown R^8 \\
\bigg| \qquad \bigg| \\
R^4 \diagup \diagdown Z \diagdown R^7 \\
R^5 \qquad R^6
\end{array} \quad mX^{n-} \quad (I)
$$

wherein $R^1$ represents an alkyl group or an aryl group, $R^2$ to $R^9$ each independently represents a hydrogen atom or a substituent and may combine with each other to form a ring, Z represents an electron-withdrawing divalent linking group, $X^{n-}$ represents an n-valent anion, n represents an integer of 1 to 3, and m represents the number of anions necessary for neutralizing the electric charge.

(2) The resist composition as described in (1) above, which further comprises (B) a resin capable of decomposing under the action of an acid to increase the solubility in an alkali developer.

(3) The resist composition as described in (1) above, which further comprises (D) a resin soluble in an alkali developer and (E) an acid crosslinking agent capable of crosslinking with the resin soluble in an alkali developer under the action of an acid.

(4) The resist composition as described in (1) to (3) above, which is exposed with an X-ray, an electron beam or EUV.

(5) The resist composition as described in (2) above, wherein the resin (B) has a hydroxystyrene structural unit.

(6) The resist composition as described in (2) above, wherein the resin (B) contains a repeating unit having a monocyclic or polycyclic hydrocarbon structure.

(7) The resist composition as described in (2) above, wherein the resin (B) is a resin containing a repeating unit having an alcoholic hydroxyl group and capable of decomposing under the action of an acid to increase the solubility in an alkali developer.

(8) The resist composition as described in (7) above, wherein the repeating unit having an alcoholic hydroxyl group in the resin (B) is a repeating unit having at least one member selected from a monohydroxyadamantane structure, a dihydroxyadamantane structure and a trihydroxyadamantane structure.

(9) The resist composition as described in (2) above, wherein the resin (B) is a resin containing a repeating unit having a lactone structure.

(10) The resist composition as described in (2) above, wherein the resin (B) is a resin containing at least one methacrylic acid ester repeating unit and at least one acrylic acid ester repeating unit.

(11) The resist composition as described in (2) above, wherein the resin (B) has a fluorine atom in the main or side chain.

(12) The resist composition as described in (2) above, wherein the resin (B) has a hexafluoro-2-propanol structure.

(13) The resist composition as described in any one of (5) to (12) above, which further comprises (C) a dissolution inhibiting compound capable of decomposing under the action of an acid to increase the solubility in an alkali developer and having a molecular weight of 3,000 or less.

(14) The resist composition as described in any one of (5) to (13), which further comprises (F) a basic compound and/or (G) a fluorine- and/or silicon-containing surfactant.

(15) The resist composition as described in (6) above, wherein the resin (B) comprises: at least one repeating unit selected from 2-alkyl-2-adamantyl(meth)acrylate and dialkyl (1-adamantyl)methyl(meth)acrylate; at least one repeating unit having a lactone structure; and at least one repeating unit having two or more hydroxyl groups.

(16) The resist composition as described in (15) above, wherein the resin (B) further contains a repeating unit having a carboxy group.

(17) The resist composition as described in (5) above, wherein the resin (B) comprises: at least one repeating unit selected from 2-alkyl-2-adamantyl(meth)acrylate and dialkyl (1-adamantyl)methyl(meth)acrylate; and at least one repeating unit having a hydroxystyrene structure.

(18) A pattern forming method comprising forming a photosensitive film from the resist composition described in any one of (1) to (17) above, and exposing and developing the photosensitive film.

(19) A sulfonium compound represented by formula (II):

Formula (II):

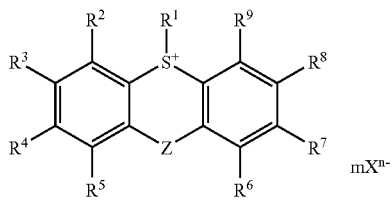

wherein
$R^1$ represents an aryl group,
$R^2$ to $R^9$ each independently represents a hydrogen atom or a substituent and may combine with each other to form a ring,
Z represents a sulfone group,
$X^{n-}$ represents an n-valent anion,
n represents an integer of 1 to 3, and
m represents the number of anions necessary for neutralizing the electric charge.

(20) A sulfonium compound represented by formula (III):

Formula (III):

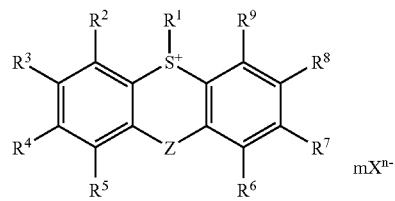

wherein
$R^1$ represents an alkyl group or an aryl group,
$R^2$ to $R^9$ each independently represents a hydrogen atom or a substituent and may combine with each other to form a ring, provided that at least one of $R^1$ to $R^9$ contains an alcoholic hydroxyl group,
Z represents an electron-withdrawing divalent linking group,
$X^{n-}$ represents an n-valent anion,
n represents an integer of 1 to 3, and
m represents the number of anions necessary for neutralizing the electric charge.

According to the present invention, a resist composition excellent in the sensitivity and outgassing properties, a compound for use in the resist composition and a pattern forming method using the resist composition can be provided.

Description of Numerical References

Figure 1:
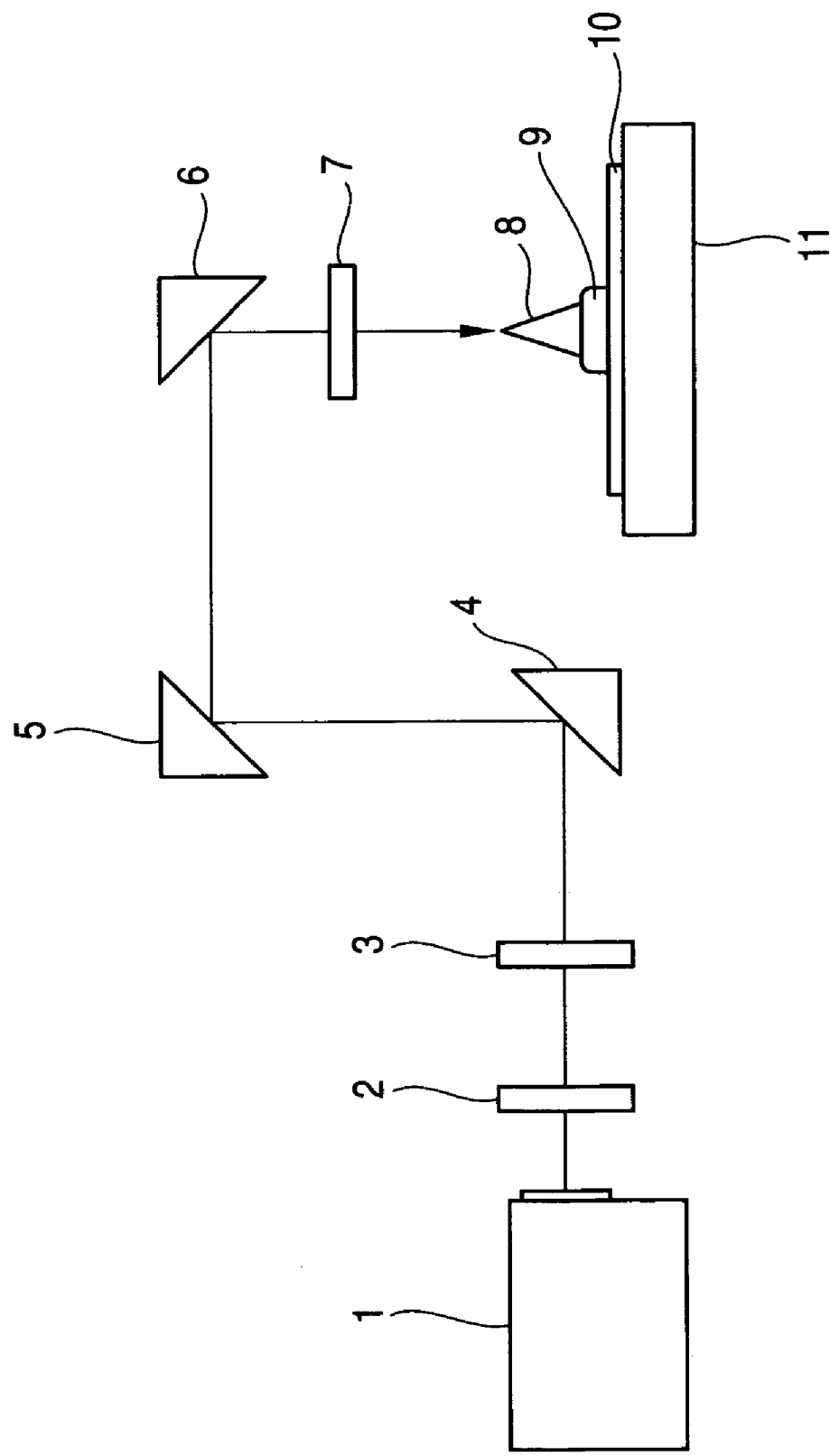
FIG. 1 is a schematic view of the two-beam interference exposure testing apparatus.

1 Laser
2 Diaphragm
3 Shutter
4, 5, 6 Reflecting mirrors
7 Condenser lens
8 Prism
9 Immersion solution
10 Wafer with antireflection film and resist film
11 Wafer stage

DETAILED DESCRIPTION OF THE INVENTION

The present invention is described in detail below.

In the present invention, when a group (atomic group) is denoted without specifying whether substituted or unsubstituted, the group includes a group having no substituent and a group having a substituent. For example, an "alkyl group" includes not only an alkyl group having no substituent (unsubstituted alkyl group) but also an alkyl group having a substituent (substituted alkyl group).

The resist composition of the present invention may be a positive resist composition or a negative resist composition.

The positive resist composition of the present invention comprises (A) a sulfonium salt represented by formula (I) and (B) a resin capable of decomposing under the action of an acid to increase the solubility in an alkali developer and, if desired, further comprises (C) a dissolution inhibiting compound capable of decomposing under the action of an acid to increase the solubility in an alkali developer and having a molecular weight of 3,000 or less.

The negative resist composition of the present invention comprises (A) a sulfonium salt represented by formula (I), (D) a resin soluble in an alkali developer, and (E) an acid crosslinking agent capable of crosslinking with the resin soluble in an alkali developer under the action of an acid.

[1] (A) Sulfonium Compound Represented by Formula (I)

The resist composition of the present invention comprises a sulfonium compound represented by formula (I) (hereinafter, sometimes simply referred to as a "sulfonium salt (A)") as a compound capable of generating an acid upon irradiation of actinic rays or radiation.

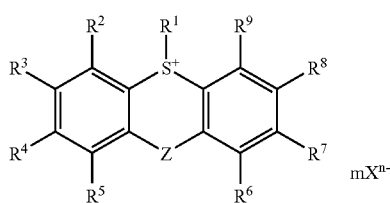

wherein $R^1$ represents an alkyl group or an aryl group, $R^2$ to $R^9$ each independently represents a hydrogen atom or a substituent and may combine with each other to form a ring, Z represents an electron-withdrawing divalent linking group, $X^{n-}$ represents an n-valent anion, n represents an integer of 1 to 3, and m represents the number of anions necessary for neutralizing the electric charge.

The sulfonium compound (A) represented by formula (I) has an anion $X^{n-}$. The anion is preferably an organic anion. The organic anion indicates an anion containing at least one carbon atom. The organic anion $X^{n-}$ is preferably a non-nucleophilic anion.

The non-nucleophilic anion is an anion having a low ability of causing a nucleophilic reaction, and this anion can suppress the decomposition in aging due to intramolecular nucleophilic reaction. Examples of the non-nucleophilic anion include a sulfonate anion, a carboxylate anion, a sulfonylimide anion, a bis(alkylsulfonyl)imide anion and a tris(alkylsulfonyl)methyl anion.

Examples of the sulfonate anion include an alkylsulfonate anion, an arylsulfonate anion and a camphorsulfonate anion.

Examples of the non-nucleophilic carboxylate anion include an alkylcarboxylate anion, an arylcarboxylate anion and an aralkylcarboxylate anion.

The alkyl moiety in the alkylsulfonate anion may be an alkyl group or a cycloalkyl group and is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a boronyl group.

The aryl group in the arylsulfonate anion is preferably an aryl group having a carbon number of 6 to 14, and examples thereof include a phenyl group, a tolyl group and a naphthyl group.

The alkyl group, cycloalkyl group and aryl group in the alkylsulfonate anion and arylsulfonate anion each may further have a substituent, and examples of the substituent which those groups may further have include a nitro group, a halogen atom (e.g., fluorine, chlorine, bromine, iodine), a carboxyl group, a hydroxyl group, an amino group, a cyano group, an alkoxy group (preferably having a carbon number of 1 to 5), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), and an alkoxycarbonyloxy group (preferably having a carbon number of 2 to 7). As for the aryl group or ring structure in each group, examples of the substituent further include an alkyl group (preferably having a carbon number of 1 to 15).

Examples of the alkyl moiety in the alkylcarboxylate anion include the same alkyl group and cycloalkyl group as those described above for the alkylsulfonate anion.

Examples of the aryl group in the arylcarboxylate anion include the same aryl group as those described above for the arylsulfonate anion.

The aralkyl group in the aralkylcarboxylate anion is preferably an aralkyl group having a carbon number of 6 to 12, and examples thereof include a benzyl group, a phenethyl group, a naphthylethyl group and a naphthylmethyl group.

The alkyl group, cycloalkyl group, aryl group and aralkyl group in the alkylcarboxylate anion, arylcarboxylate anion and aralkylcarboxylate anion each may further have a substituent, and examples of the substituent which those groups may further have include the same halogen atom, alkyl group, cycloalkyl group, alkoxy group and alkylthio group as those described above for the arylsulfonate anion.

Examples of the sulfonylimide anion include a saccharine anion.

The alkyl group in the bis(alkylsulfonyl)imide anion and tris(alkylsulfonyl)methyl anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. This alkyl group may further have a substituent, and examples of the substituent which the alkyl group may further have include a halogen atom, an alkoxy group substituted by a halogen atom, an alkoxy group and an alkylthio group, with an alkyl group substituted by fluorine atom being preferred.

Other examples of the non-nucleophilic anion include a phosphorus fluoride anion, a boron fluoride anion and an antimony fluoride anion.

The non-nucleophilic anion is preferably a sulfonate anion. Specific preferred examples of the sulfonate anion include trifluoromethanesulfonate anion, pentafluoroethanesulfonate anion, heptafluoropropanesulfonate anion, perfluorobutanesulfonate anion, perfluorohexanesulfonate anion, perfluorooctanesulfonate anion, pentafluorobenzenesulfonate anion, 3,5-bistrifluoromethylbenzenesulfonate anion, 2,4,6-triisopropylbenzenesulfonate anion, perfluoroethoxyethanesulfonate anion, 2,3,5,6-tetrafluoro-4-dodecyloxybenzenesulfonate anion, methanesulfonate anion, p-toluenesulfonate anion, 3,5-bistrifluorobenzenesulfonate anion, pentafluorobenzenesulfonate anion and 2,4,6-trimethylbenzenesulfonate anion.

The anion present in the sulfonium salt (A) together with the cation represented by formula (I) may be monovalent or may be divalent or more. In the case where the anion is divalent or more, the sulfonium salt (A) may have two or more cations represented by formula (I).

$R^1$ represents an alkyl group or an aryl group.

The alkyl group of $R^1$ is preferably a linear or branched alkyl group having a carbon number of 1 to 20, more preferably a linear or branched alkyl group having a carbon number of 1 to 12, and examples thereof include a methyl group, an ethyl group, a propyl group, an isopropyl group, an n-butyl group and an isobutyl group. The cycloalkyl group is preferably a cycloalkyl group having a carbon number of 3 to 20, more preferably a cycloalkyl group having a carbon number of 5 to 15, and examples thereof include a cyclopentyl group, a cyclohexyl group, a cycloheptyl group, a norbornyl group and an adamantyl group.

Examples of the aryl group of $R^1$ include a phenyl group and a naphthyl group, with a phenyl group being preferred.

$R^1$ is preferably an aryl group which may be substituted or unsubstituted, more preferably an aryl group having a substituent, still more preferably a phenyl group having a substituent.

Examples of the substituent which the alkyl group and the aryl group of $R^1$ each may have include a halogen atom, an alkyl group, an alkenyl group, an alkynyl group, an aryl group, a cyano group, a hydroxyl group, a nitro group, a carboxyl group, an alkoxy group, an aryloxy group, a silyloxy group, an acyloxy group, a carbamoyloxy group, an alkoxycarbonyloxy group, an aryloxycarbonyloxy group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an imido group, a silyl group and a ureido group.

The substituent which the alkyl group and the aryl group of $R^1$ each has is preferably an alkyl group, an alkenyl group, an alkynyl group, an alkoxy group, an acyloxy group, a sulfamoylamino group, an alkyl- or aryl-sulfonylamino group, an alkylthio group, an arylthio group, a sulfamoyl group, an alkyl- or aryl-sulfinyl group, an alkyl- or aryl-sulfonyl group, an acyl group, an aryloxycarbonyl group, an alkoxycarbonyl group or a carbamoyl group, more preferably an alkyl group, an alkoxy group, an alkylsulfonylamino group, an alkylthio group, a sulfamoyl group, an alkyl- or aryl sulfonyl group or an alkoxycarbonyl group.

These substituents each may further have a substituent, and examples of the substituent include the substituents described above for $R^1$.

$R^2$ to $R^9$ each is independently a hydrogen atom or a substituent, and examples of the substituent include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a cyano group, a hydroxyl group, a nitro group, a carboxyl group, an alkoxy group, an aryloxy group, a silyloxy group, an acyloxy group, a carbamoyloxy group, an alkoxycarbonyloxy group, an aryloxycarbonyloxy group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an imido group, a silyl group and a ureido group.

Also, two members out of $R^2$ to $R^9$ may form a ring in cooperation (may form an aromatic or non-aromatic hydrocarbon ring or may combine with a heterocyclic ring to form a polycyclic condensed ring; examples thereof include a benzene ring, a naphthalene ring, an anthracene ring, a phenanthrene ring, a fluorene ring, a triphenylene ring, a naphthacene ring, a biphenyl ring, a furan ring, a thiophene ring, an oxazole ring, a thiazole ring, a benzofuran ring, a benzothiophene ring and an isobenzofuran ring).

$R^2$ to $R^9$ each is preferably a hydrogen atom or an electron-withdrawing group, and specific examples of the electron-withdrawing group include a halogen atom (e.g., fluorine, chlorine, bromine, iodine), a cyano group, a nitro group, a carboxyl group, an acyloxy group (preferably a formyloxy group, a substituted or unsubstituted alkylcarbonyloxy group having a carbon number of 2 to 30, or a substituted or unsubstituted arylcarbonyloxy group having a carbon number of 6 to 30, e.g., formyloxy, acetyloxy, pivaloyloxy, stearoyloxy, benzoyloxy, p-methoxyphenylcarbonyloxy), a carbamoyloxy group (preferably a substituted or unsubstituted carbamoyloxy group having a carbon number of 1 to 30, e.g., N,N-dimethylcarbamoyloxy, N,N-diethylcarbamoyloxy, morpholinocarbonyloxy, N,N-di-n-octylaminocarbonyloxy, N-n-octylcarbamoyloxy), an alkoxycarbonyloxy group (preferably a substituted or unsubstituted alkoxycarbonyloxy group having a carbon number of 2 to 30, e.g., methoxycarbonyloxy, ethoxycarbonyloxy, tert-butoxycarbonyloxy, n-octylcarbonyloxy), an aryloxycarbonyloxy group (preferably a substituted or unsubstituted aryloxycarbonyloxy group having a carbon number of 7 to 30, e.g., phenoxycarbonyloxy, p-methoxyphenoxycarbonyloxy, p-n-hexadecyloxyphenoxycarbonyloxy), an acylamino group (preferably a formylamino group, a substituted or unsubstituted alkylcarbonylamino group having a carbon number of 1 to 30, a substituted or unsubstituted arylcarbonylamino group having a carbon number of 6 to 30, e.g., formylamino, acetylamino, pivaloylamino, lauroylamino, benzoylamino, 3,4,5-tri-n-octyloxyphenylcarbonylamino), an aminocarbonylamino group (preferably a substituted or unsubstituted aminocarbonylamino group having a carbon number of 1 to 30, e.g., carbamoylamino, N,N-dimethylaminocarbonylamino, N,N-diethylaminocarbonylamino, morpholinocarbonylamino), an alkoxycarbonylamino group (preferably a substituted or unsubstituted alkoxycarbonylamino group having a carbon number of 2 to 30, e.g., methoxycarbonylamino, ethoxycarbonylamino, tert-butoxycarbonylamino, n-octadecyloxycarbonylamino, N-methylmethoxycarbonylamino), an aryloxycarbonylamino group (preferably a substituted or unsubstituted aryloxycarbonylamino group having a carbon number of 7 to 30, e.g., phenoxycarbonylamino, p-chlorophenoxycarbonylamino, m-(n-octyloxyphenoxycarbonylamino), a sulfamoylamino group (preferably a substituted or unsubstituted sulfamoylamino group having a carbon number of 0 to 30, e.g., sulfamoylamino, N,N-dimethylaminosulfonylamino, N-n-octylaminosulfonylamino), an alkyl- or aryl-sulfonylamino group (preferably a substituted or unsubstituted alkylsulfonylamino group having a carbon number of 1 to 30, a substituted or unsubstituted arylsulfonylamino group having a carbon number of 6 to 30, e.g., methylsulfonylamino, butylsulfonylamino, phenylsulfonylamino, 2,3,5-trichlorophenylsulfonylamino, p-methylphenylsulfonylamino), a sulfamoyl group (preferably a substituted or unsubstituted sulfamoyl group having a carbon number of 0 to 30, e.g., N-ethylsulfamoyl, N-(3-dodecyloxypropyl)sulfamoyl, N,N-dimethylsulfamoyl, N-acetylsulfamoyl, N-benzoylsulfamoyl, N-(N'-phenylcarbamoyl)sulfamoyl), an alkyl- or aryl-sulfinyl group (preferably a substituted or unsubstituted alkylsulfinyl group having a carbon number of 1 to 30, or a substituted or unsubstituted arylsulfinyl group having a carbon number of 6 to 30, e.g., methylsulfinyl, ethylsulfinyl, phenylsulfinyl, p-methylphenylsulfinyl), an alkyl- or aryl-sulfonyl group (preferably a substituted or unsubstituted alkylsulfonyl group having a carbon number of 1 to 30, or a substituted or unsubstituted arylsulfonyl group having a carbon number of 6 to 30, e.g., methylsulfonyl, ethylsulfonyl, phenylsulfonyl, p-methylphenylsulfonyl), an acyl group (preferably a formyl group, a substituted or unsubstituted alkylcarbonyl group having a carbon number of 2 to 30, a substituted or unsubstituted arylcarbonyl group having a carbon number of 7 to 30, or a substituted or unsubstituted heterocyclic carbonyl group having a carbon number of 4 to 30 bonded to a carbonyl group via a carbon atom, e.g., acetyl, pivaloyl, 2-chloroacetyl, stearoyl, benzoyl, p-n-octyloxyphenylcarbonyl, 2-pyridylcarbonyl, 2-furylcarbonyl), an aryloxycarbonyl group (preferably a substituted or unsubstituted aryloxycarbonyl group having a carbon number of 7 to 30, e.g., phenoxycarbonyl, o-chlorophenoxycarbonyl, m-nitrophenoxycarbonyl, p-tert-butylphenoxycarbonyl), an alkoxycarbonyl group (preferably a substituted or unsubstituted alkoxycarbonyl group having a carbon number of 2 to 30, e.g., methoxycarbonyl, ethoxycarbonyl, tert-butoxycarbonyl, n-octadecyloxycarbonyl), and a carbamoyl group (preferably a substituted or unsubstituted carbamoyl group having a carbon number of 1 to 30, e.g., carbamoyl, N-methylcarbamoyl, N,N-dimethylcarbamoyl, N,N-di-n-octylcarbamoyl, N-(methylsulfonyl)carbamoyl).

$R^1$ to $R^9$ each preferably contains an alcoholic hydroxyl group. The alcoholic hydroxyl group is a hydroxyl group substituted to an alkyl group.

Z represents an electron-withdrawing divalent linking group, and specific examples thereof include a carbonyl group, a sulfoxide group, a sulfone group, —COO—, —CONH—, —SO$_2$NH—, —CF$_2$—, —CF$_2$CF$_2$—, —OCF$_2$O—, —CF$_2$OCF$_2$—, —SS—, —CH$_2$SO$_2$CH$_2$—, —CH$_2$COCH$_2$—, —COCF$_2$CO—, —COCO—, —OCOO— and —OSO$_2$O—.

Z is preferably a carbonyl group, a sulfoxide group, a sulfone group, —COO—, —CONH—, —SO$_2$NH—, —CF$_2$—, —CF$_2$CF$_2$— or —COCO—, more preferably a carbonyl group, a sulfoxide group or a sulfone group, still more preferably a sulfone group.

As the sulfonium salt (A) represented by the formula (I), a sulfonium compound represented by formula (II) or (III) also is preferable.

Formula (II):

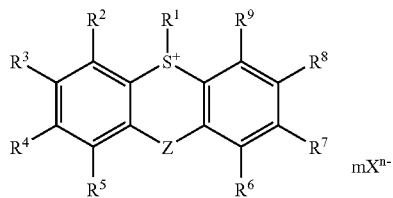

wherein
$R^1$ represents an aryl group,
$R^2$ to $R^9$ each independently represents a hydrogen atom or a substituent and may combine with each other to form a ring, Z represents a sulfone group,
$X^{n-}$ represents an n-valent anion,
n represents an integer of 1 to 3, and
m represents the number of anions necessary for neutralizing the electric charge.

Formula (III):

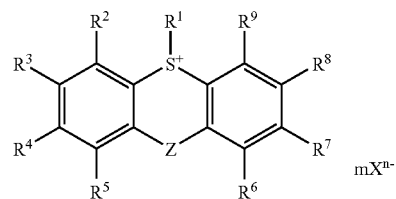

wherein
$R^1$ represents an alkyl group or an aryl group,
$R^2$ to $R^9$ each independently represents a hydrogen atom or a substituent and may combine with each other to form a ring, provided that at least one of $R^1$ to $R^9$ contains an alcoholic hydroxyl group, Z represents an electron-withdrawing divalent linking group,
$X^{n-}$ represents an n-valent anion,
n represents an integer of 1 to 3, and
m represents the number of anions necessary for neutralizing the electric charge.

Specific examples of the sulfonium salt (A) represented by formula (I) are set forth below, but the present invention is not limited thereto.

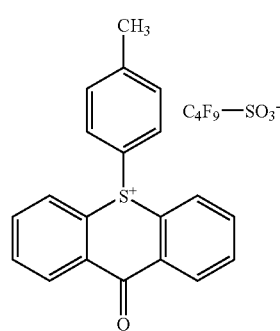

(A1)

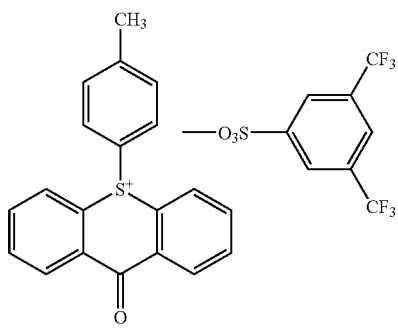

(A2)

-continued
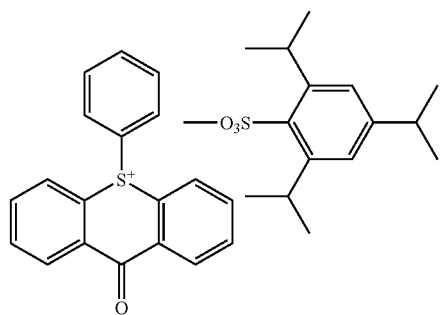 (A3)
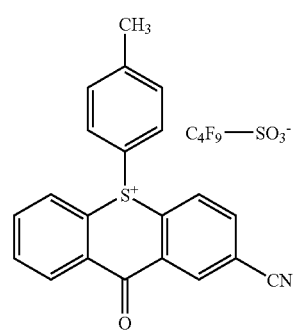 (A4)
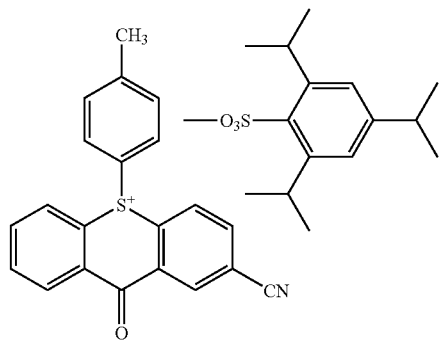 (A5)
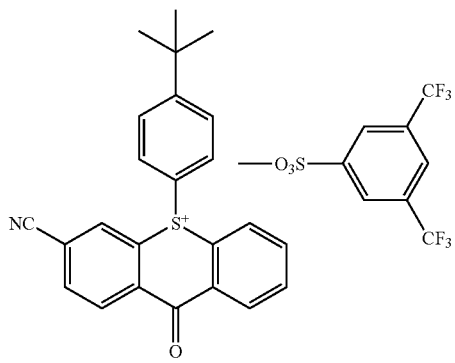 (A6)
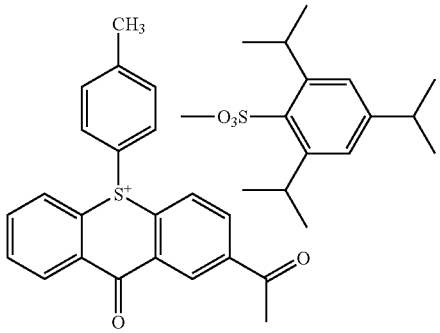 (A7)
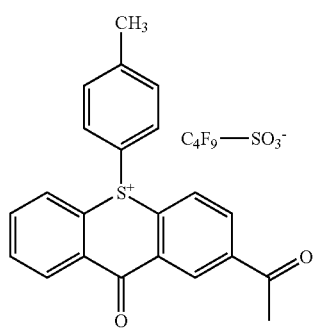 (A8)
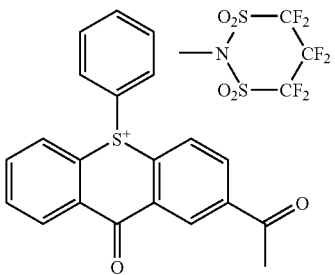 (A9)
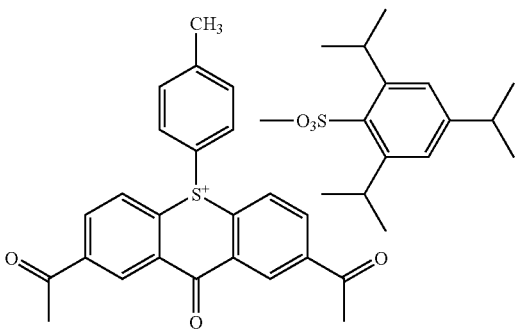 (A10)
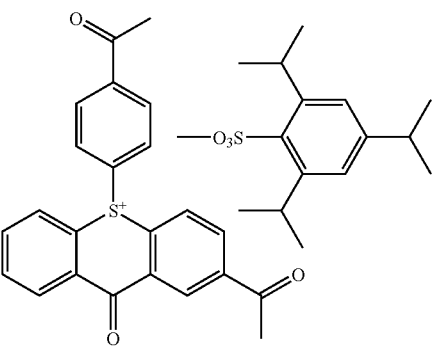 (A11)

-continued
(A12)
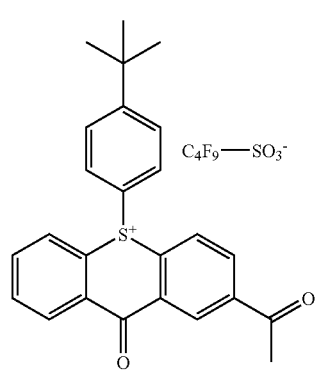
(A13)
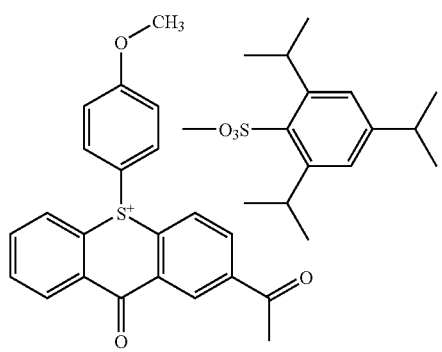
(A14)
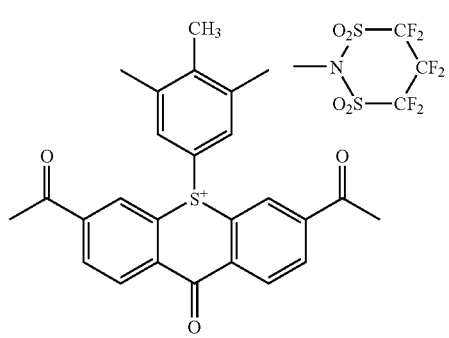
(A15)
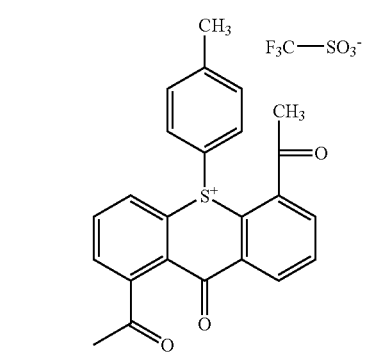
-continued
(A16)
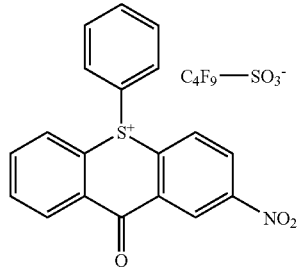
(A17)
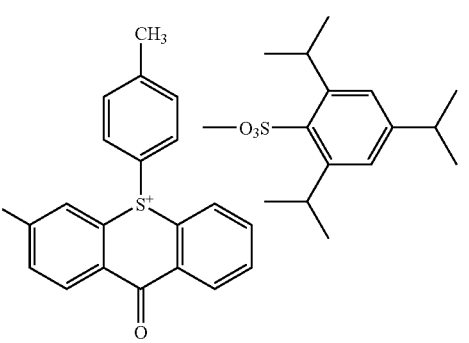
(A18)
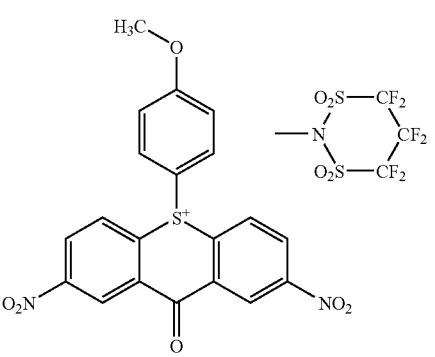
(A19)
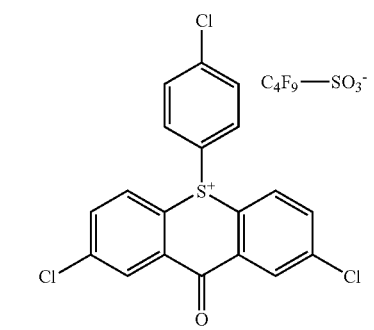

-continued
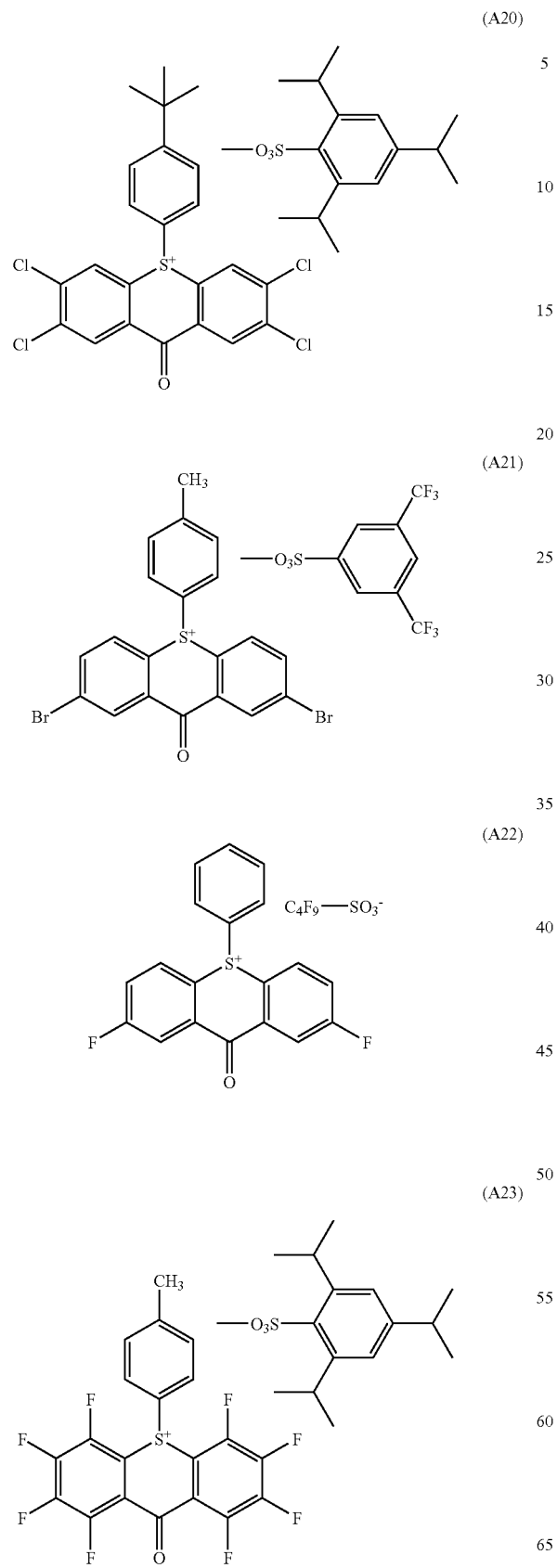
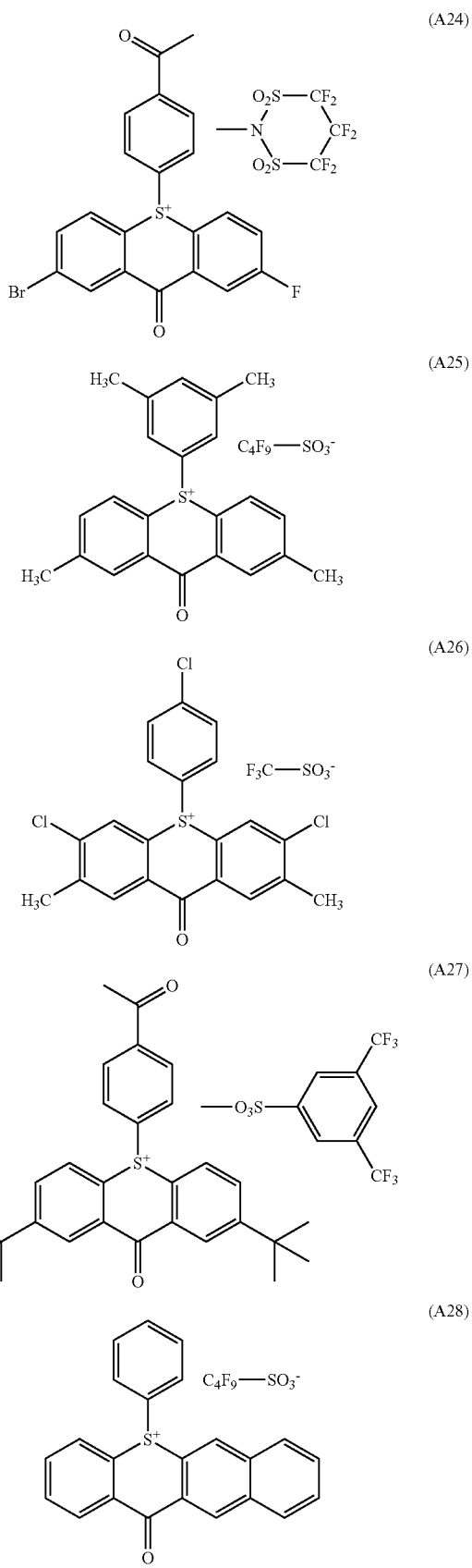

-continued
(A29)
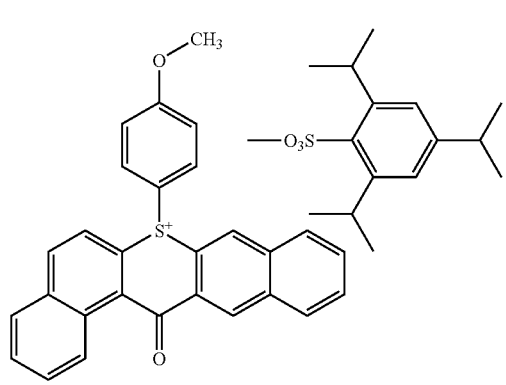
(A30)
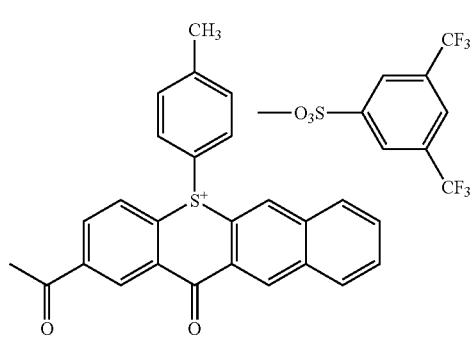
(A31)
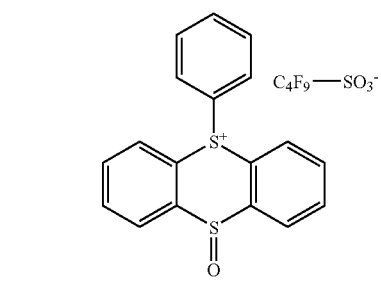
(A32)
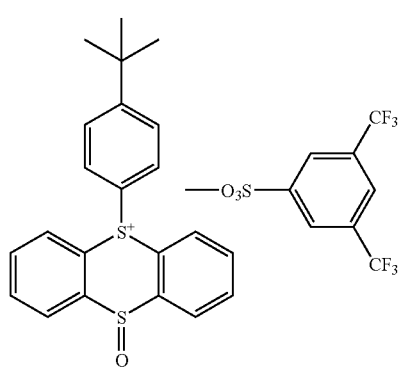
-continued
(A33)
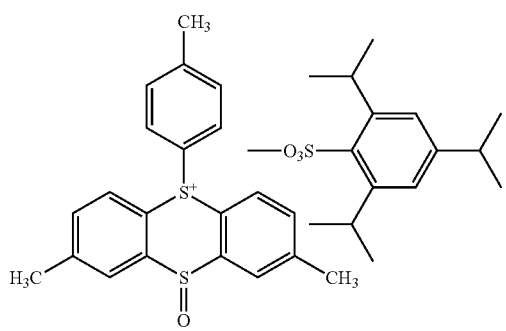
(A34)
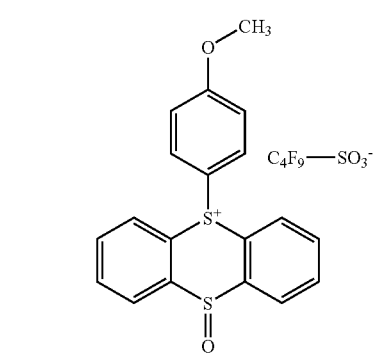
(A35)
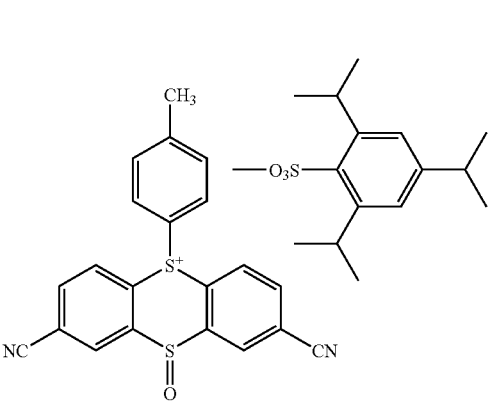
(A36)
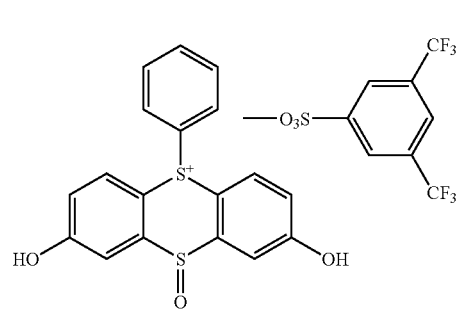

-continued
(A37)
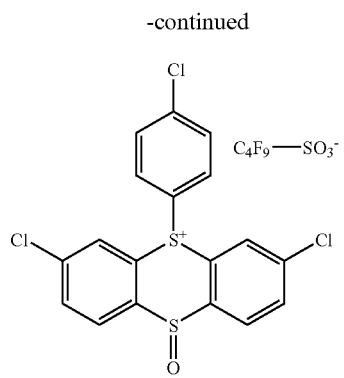
(A38)
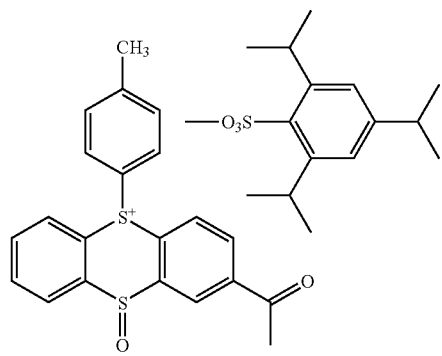
(A39)
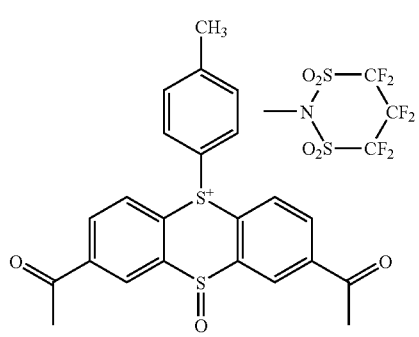
(A40)
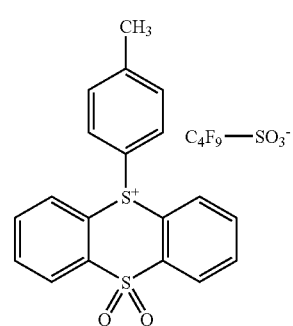
-continued
(A41)
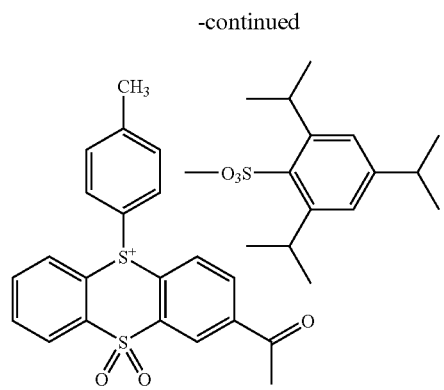
(A42)
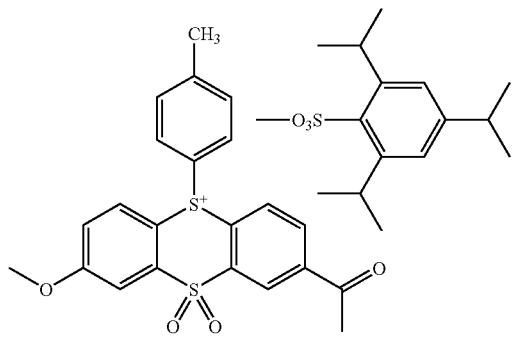
(A43)
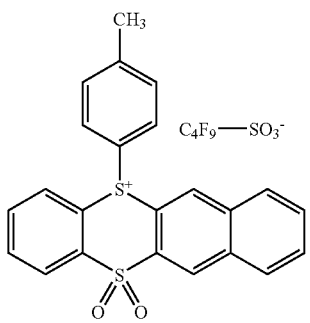
(A44)
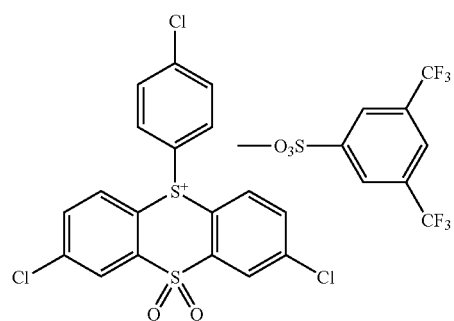

-continued
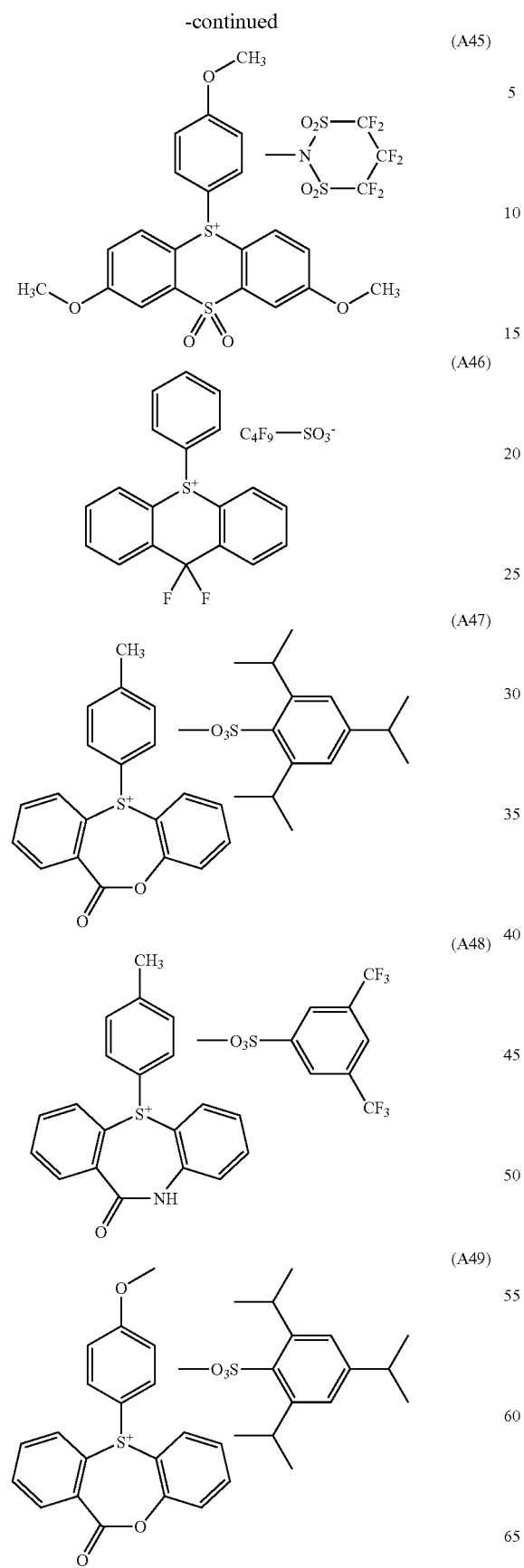
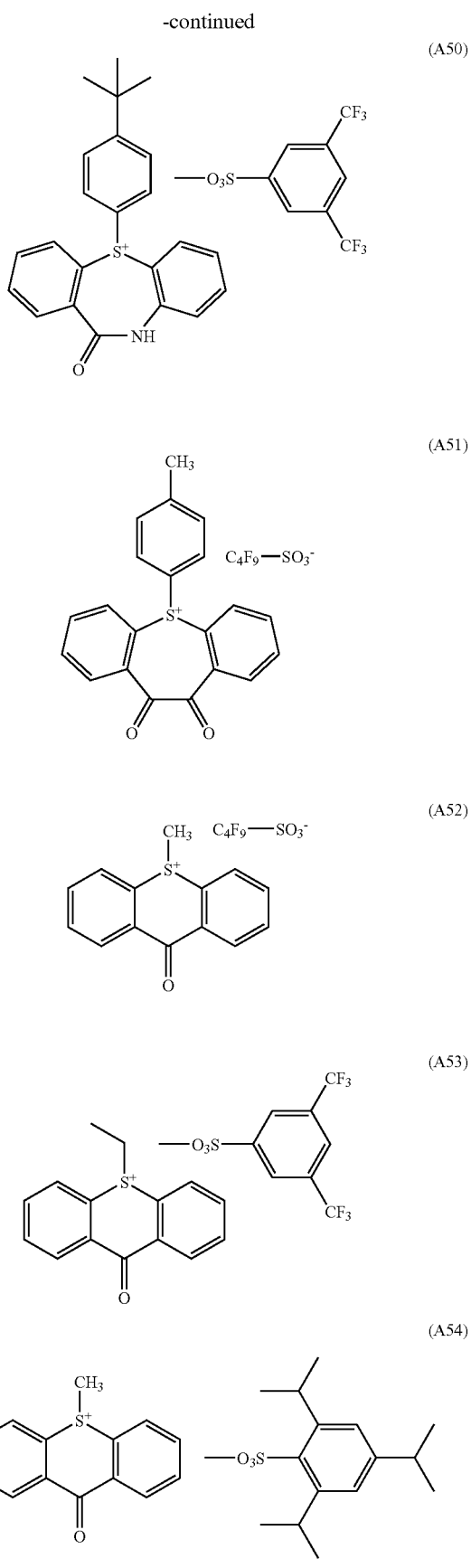

-continued (A55) (A60) (A56) (A57) (A61) (A58) (A62) (A59)

(A62) 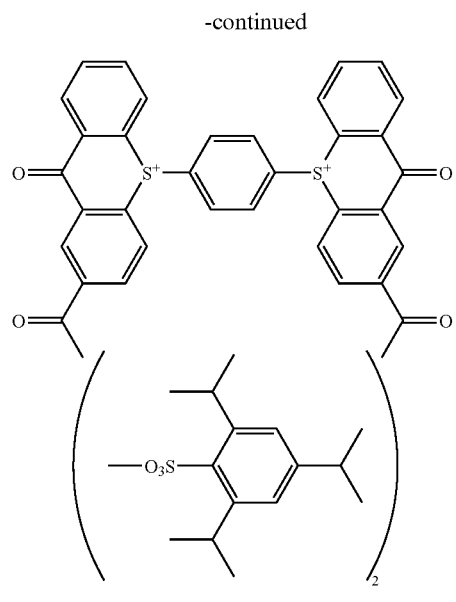
(A63) 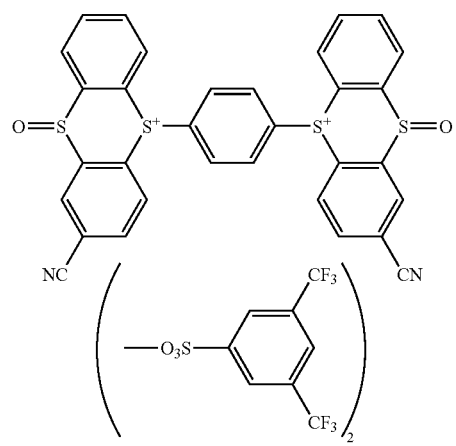
(A64)
(A65) 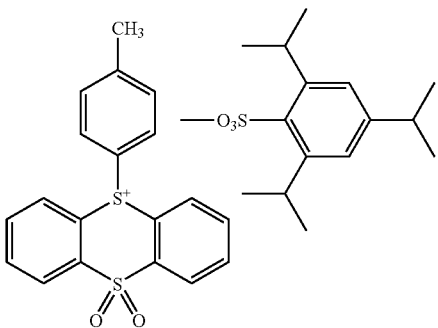
(A66) 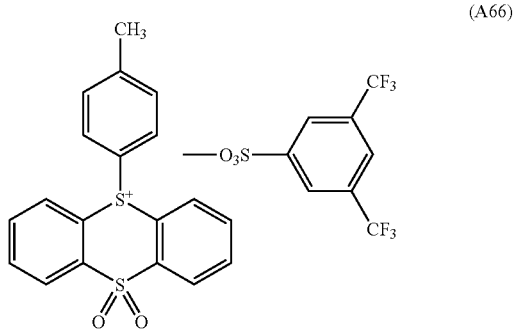
(A67) 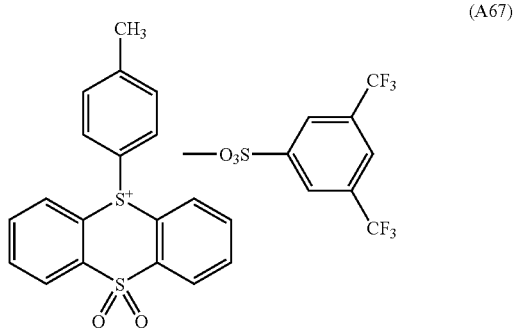
(A68) 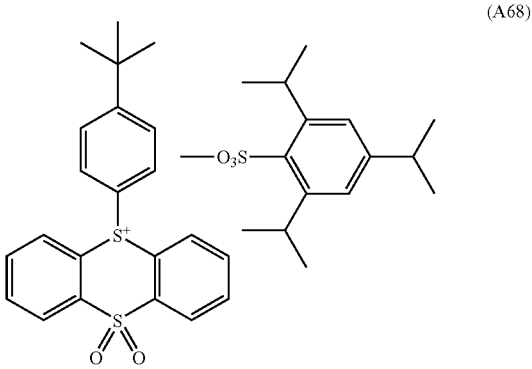

-continued
(A69)
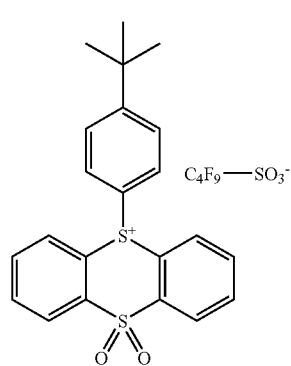
(A70)
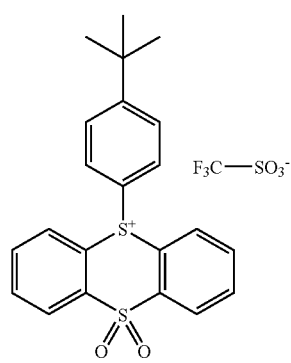
(A71)
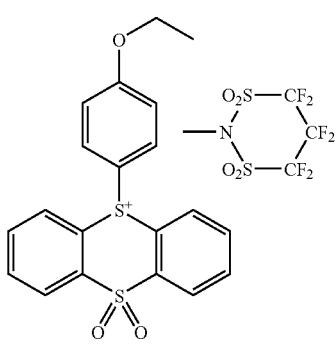
(A72)
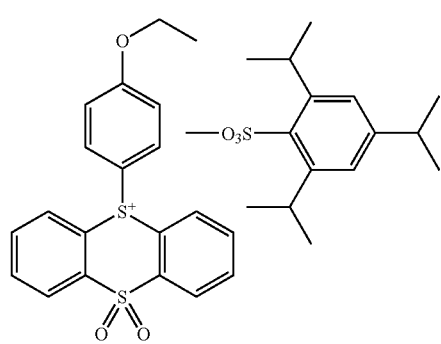
-continued
(A73)
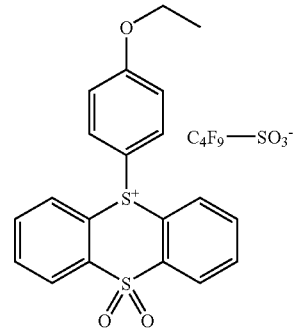
(A74)
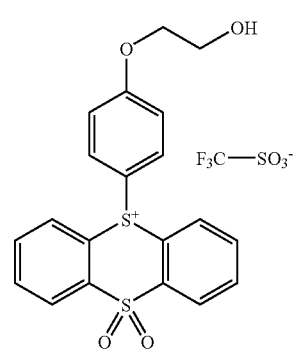
(A75)
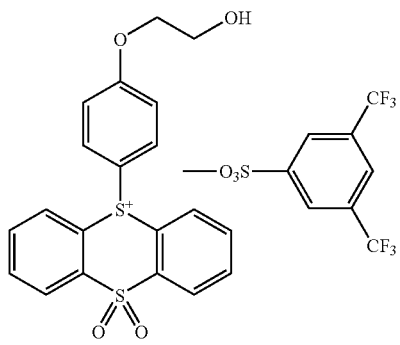
(A76)
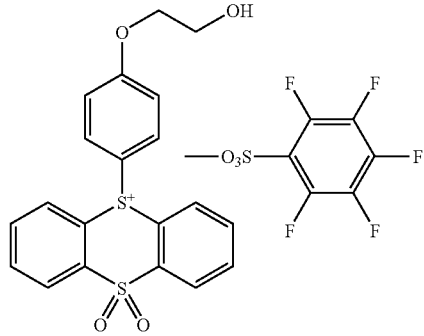

-continued
(A77) 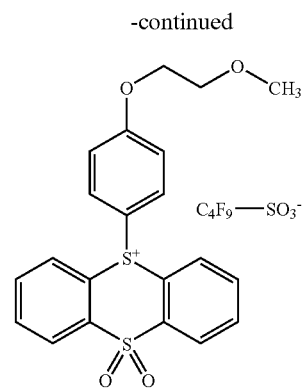
(A78) 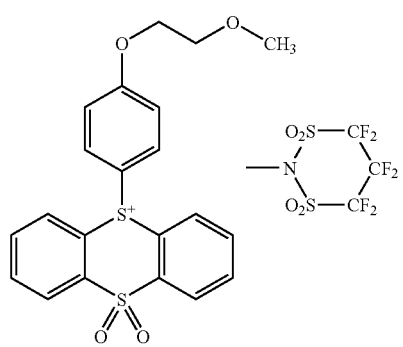
(A79) 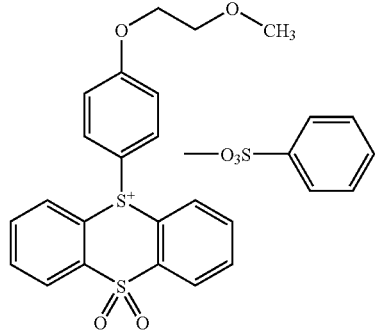
(A80) 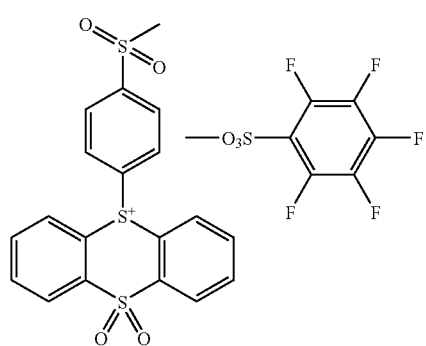
-continued
(A81) 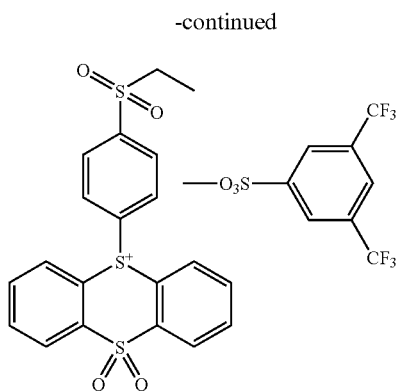
(A82) 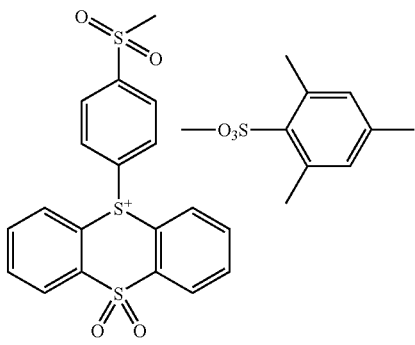
(A83) 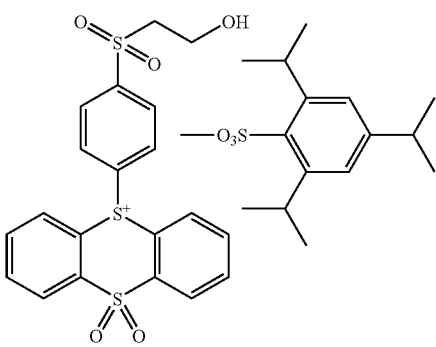
(A84) 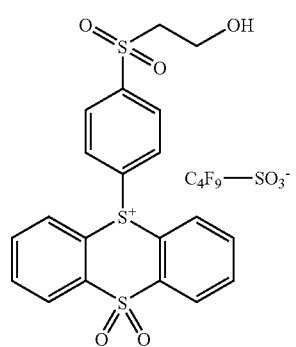

-continued
(A85) 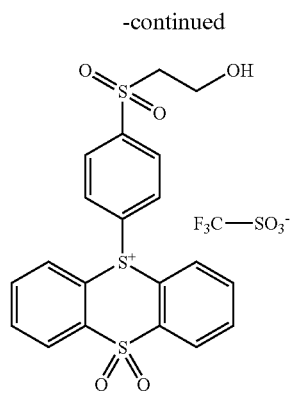
(A86) 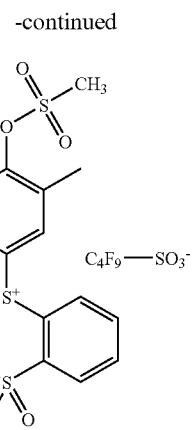
(A87)
(A88)
(A89) 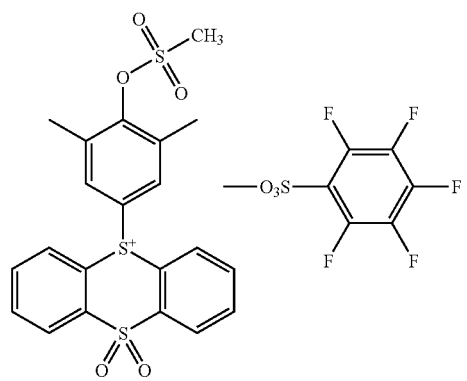
(A90)
(A91) 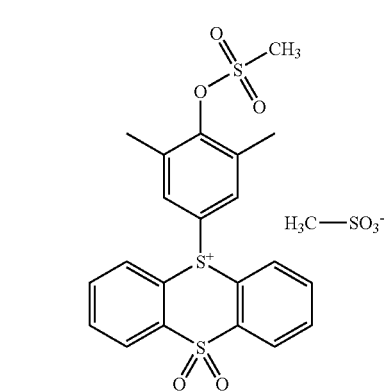
(A92) 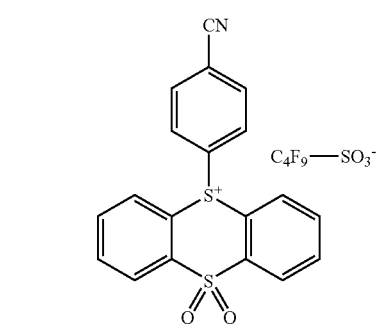

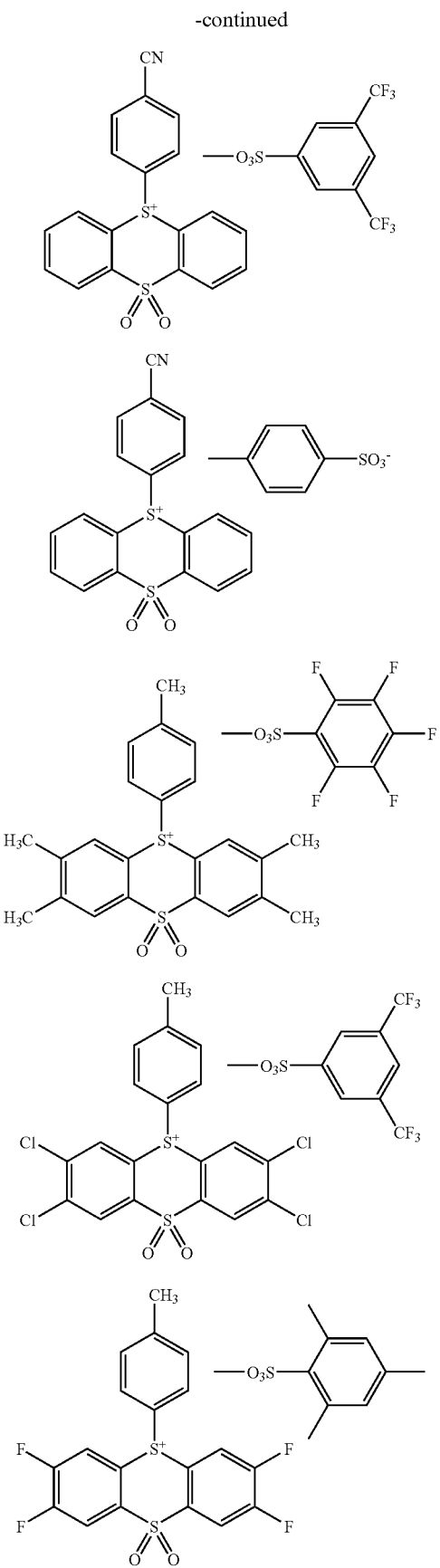
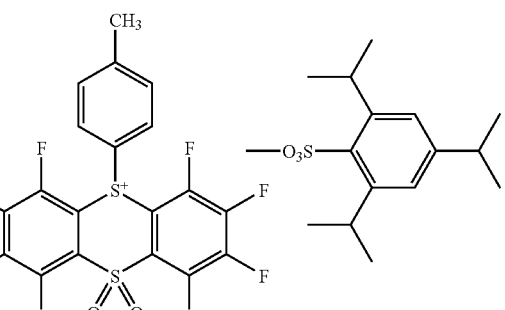

-continued
(A102)
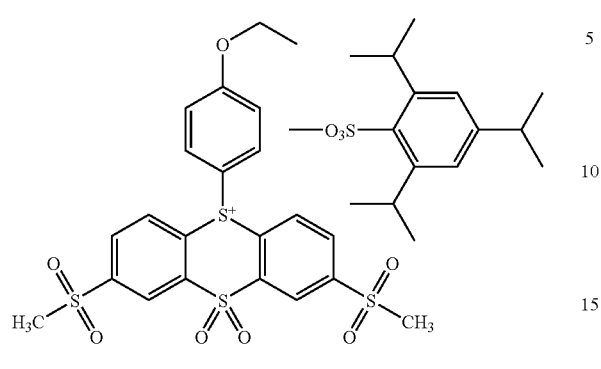
(A103)
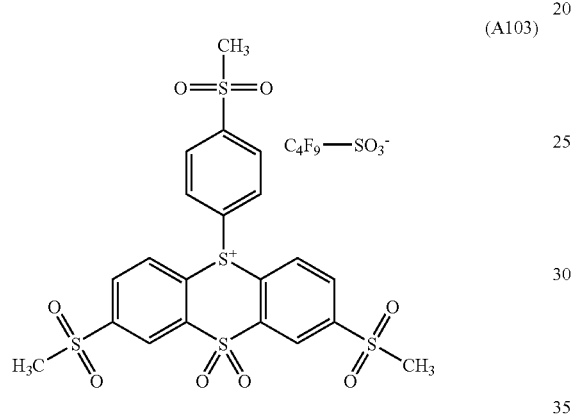
(A104)
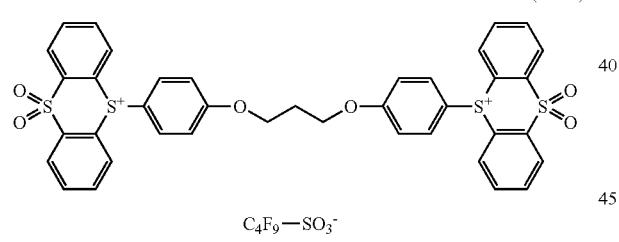
(A105)
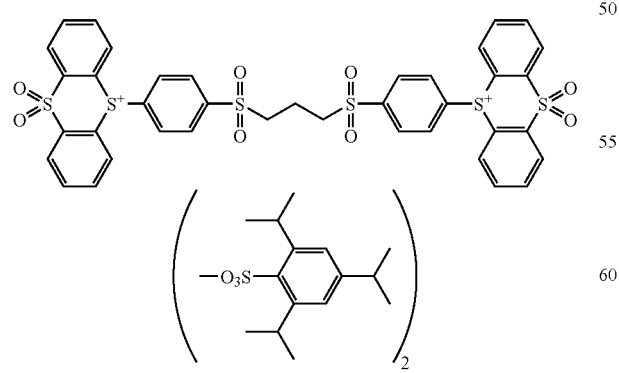
-continued
(A106)
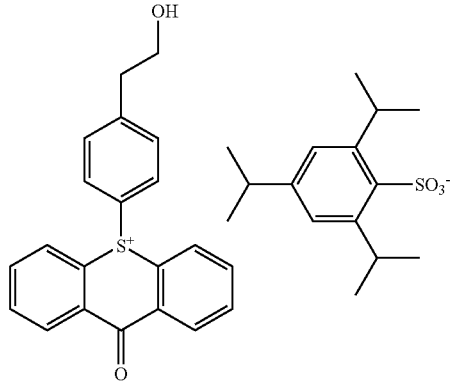
(A107)
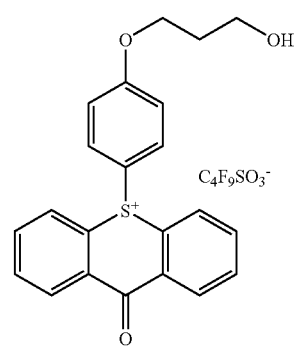
(A108)
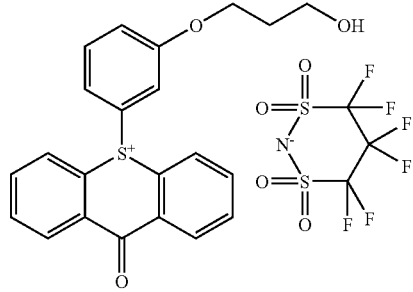
(A109)
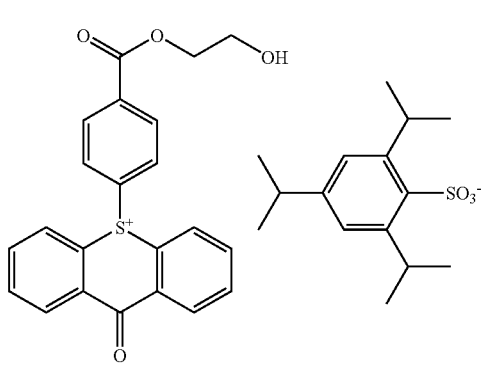

-continued (A110)
(A111)
(A112)
(A113)
(A114)
(A115)
(A116)
(A117)

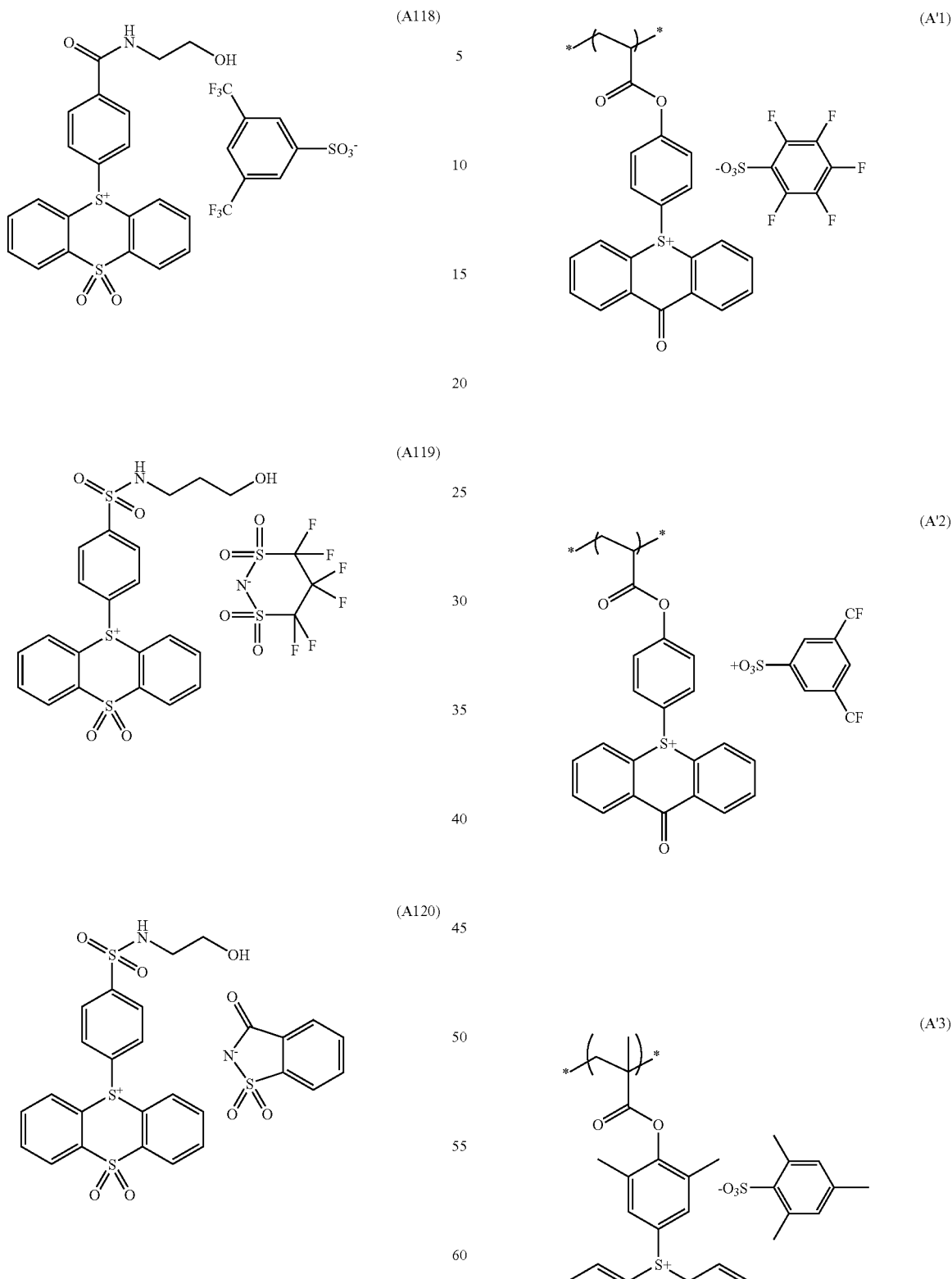
The sulfonium salt (A) represented by formula (I) may be bonded to the resin (B) described later. Examples of the repeating structural unit in the case of bonding to the resin are set forth below, but the present invention is not limited thereto.

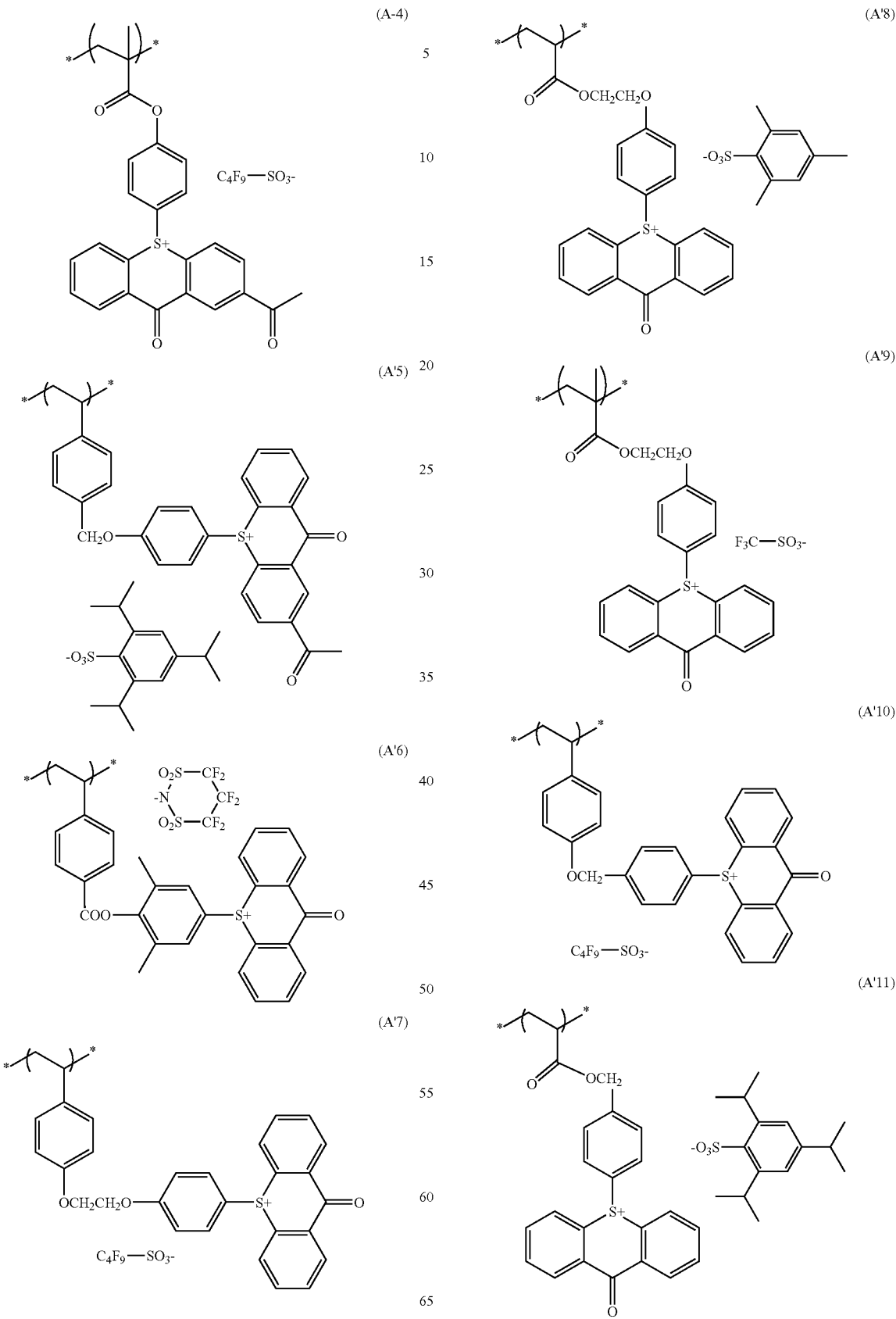

-continued
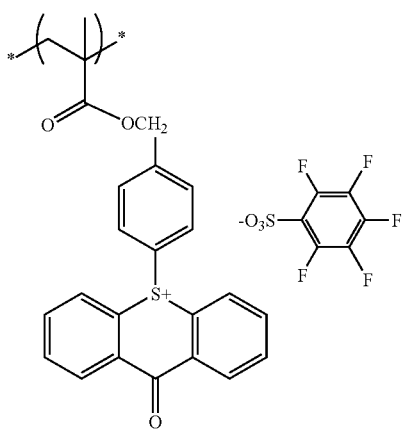 (A'12)
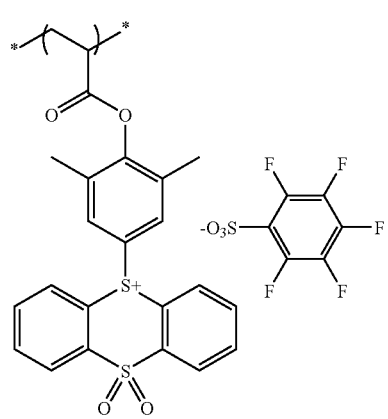 (A'13)
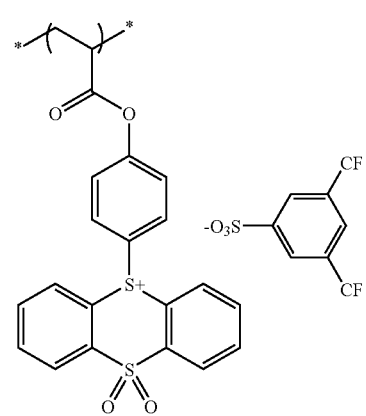 (A'14)
-continued
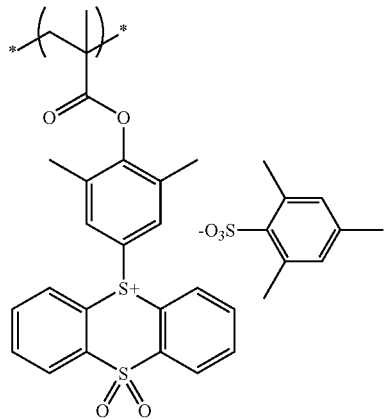 (A'15)
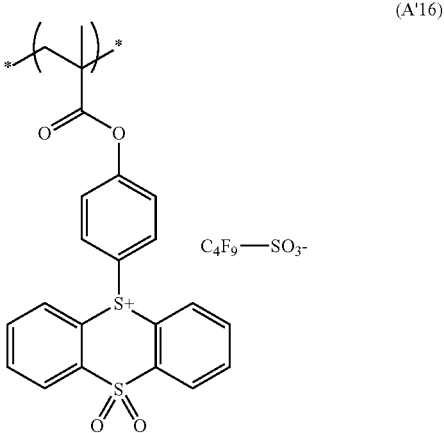 (A'16)
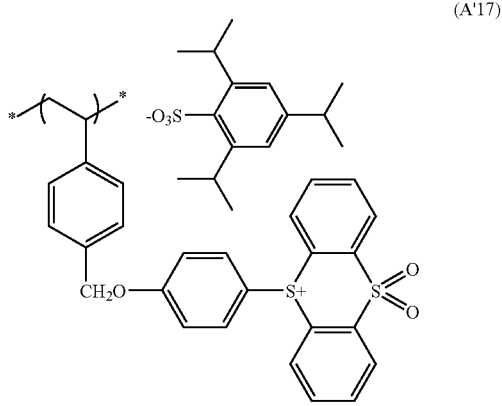 (A'17)
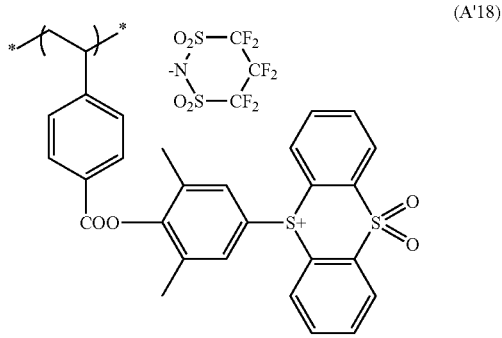 (A'18)

-continued
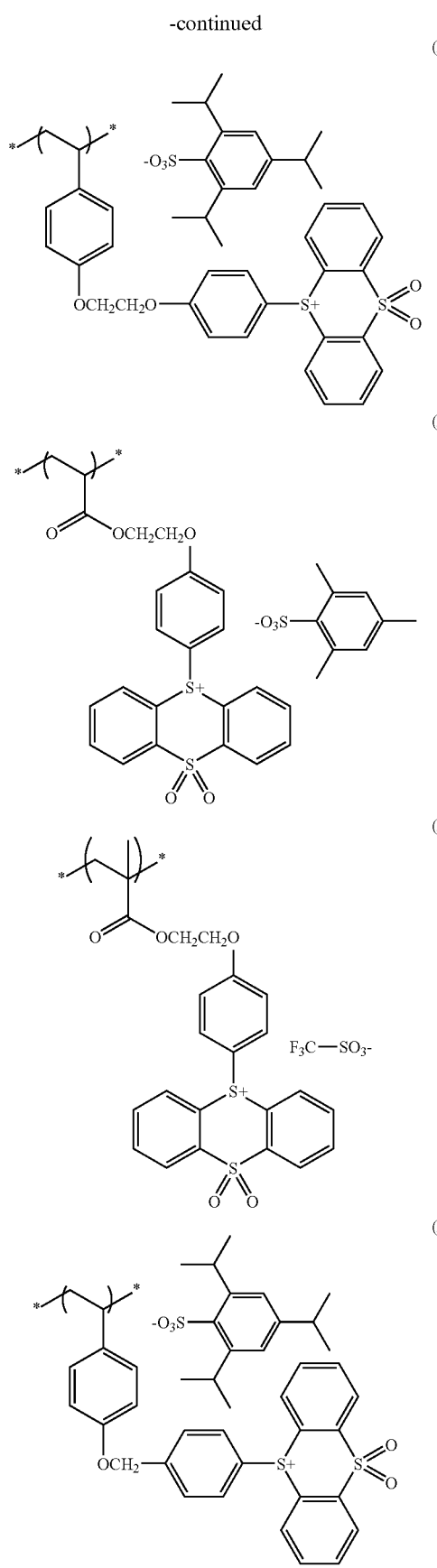
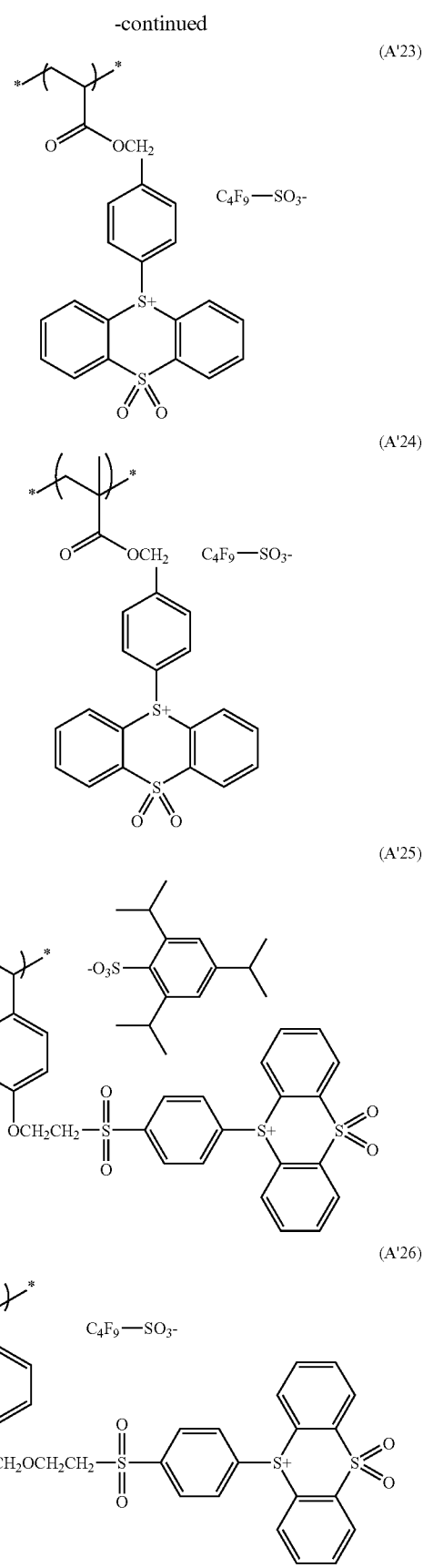

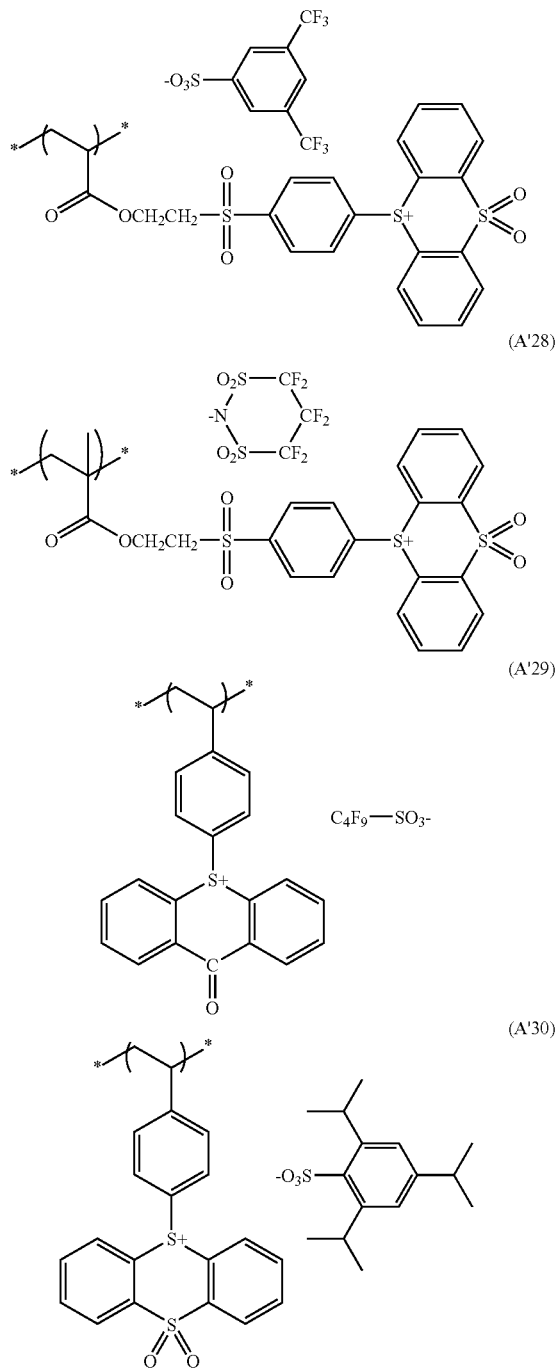

The compound of formula (1) can be synthesized by converting a cyclic sulfide compound into a sulfoxide through oxidation with hydrogen peroxide, reacting a diphenylsulfoxide compound therewith in the presence of an acid catalyst to produce a triphenylsulfonium salt structure, and then performing salt exchange with a desired anion.

The content of the sulfonium salt (A) is preferably from 0.1 to 20 mass %, more preferably from 0.5 to 10 mass %, still more preferably from 1 to 7 mass %, based on the entire solid content of the composition.

Acid Generator for Use in Combination:

Besides compound (A), a compound capable of decomposing and generating an acid upon irradiation with an actinic ray or radiation (an acid generator) may further be used in combination in the present invention.

The addition amount of other acid generators used in combination is generally from 100/0 to 20/80 in the molar ratio of (compound (A)/other acid generator], preferably from 100/0 to 40/60, and still more preferably from 100/0 to 50/50.

As such acid generators usable in combination, photo-initiators of photo-cationic polymerization, photo-initiators of photo-radical polymerization, photo-decoloring agents of dyes, photo-discoloring agents, or well-known compounds capable of generating an acid upon irradiation with an actinic ray or radiation that are used in the process of micro-resist, and mixtures of these compounds can be used by arbitrary selection.

For example, diazonium salt, phosphonium salt, sulfonium salt, iodonium salt, imidosulfonate, oximesulfonate, diazodisulfone, disulfone, and o-nitrobenzyl sulfonate are exemplified as acid generators.

Further, compounds obtained by introducing a group or a compound capable of generating an acid upon irradiation with an actinic ray or a radiation to the main chain or the side chain of polymers, for example, the compounds disclosed in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029 can be used as acid generators.

The compounds generating an acid by the action of lights as disclosed in U.S. Pat. No. 3,779,778, EP-126712 can also be used.

As preferred acid generators that can be used in the invention, the compounds represented by the following formula (ZI), (ZII) or (ZIII) can be exemplified.

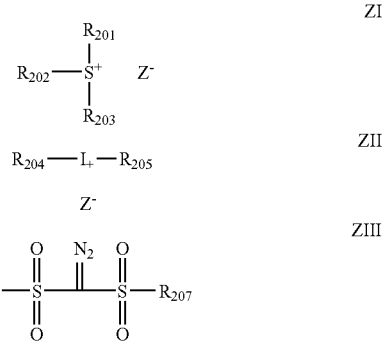

In formula (ZI), $R_{201}$, $R_{202}$ and $R_{203}$ each represents an organic group.

The number of carbon atoms of the organic groups represented by $R_{201}$, $R_{202}$ and $R_{203}$ is generally from 1 to 30, preferably from 1 to 20.

Two of $R_{201}$, $R_{202}$ and $R_{203}$ may be bonded to form a cyclic structure, and an oxygen atom, a sulfur atom, an ester bond, an amido bond or a carbonyl group may be contained in the ring.

As the group formed by bonding two of $R_{201}$, $R_{202}$ and $R_{203}$, an alkylene group (e.g., a butylene group, a pentylene group) can be exemplified.

$Z^-$ represents a non-nucleophilic anion.

The examples of non-nucleophilic anions represented by $Z^-$ include, e.g., a sulfonate anion, a carboxylate anion, a sulfonylimide anion, a bis(alkylsulfonyl)imide anion, and a tris(alkylsulfonyl)methyl anion.

A non-nucleophilic anion is an anion having extremely low ability of causing a nucleophilic reaction and capable of restraining the aging decomposition due to an intramolecular nucleophilic reaction, so that the aging stability of a resist can be improved with a non-nucleophilic anion.

As sulfonate anions, e.g., an alkyl sulfonate anion, an aryl sulfonate anion and a camphor sulfonate anion are exemplified.

As carboxylate anions, e.g., an alkyl carboxylate anion, an aryl carboxylate anion and an aralkylcarboxylate anion are exemplified.

The alkyl moiety in an alkyl sulfonate anion may be an alkyl group or a cycloalkyl group, preferably an alkyl group having from 1 to 30 carbon atoms and a cycloalkyl group having from 3 to 30 carbon atoms, e.g., a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbonyl group and a boronyl group are exemplified.

The aryl group in an aryl sulfonate anion is preferably an aryl group having from 6 to 14 carbon atoms, e.g., a phenyl group, a tolyl group, and a naphthyl group are exemplified.

As the substituents of the alkyl group, cycloalkyl group and aryl group in the above alkyl sulfonate anion and aryl sulfonate anion, e.g., a nitro group, a halogen atom (a fluorine atom, a chlorine atom, a bromine atom, and an iodine atom), a carboxyl group, a hydroxyl group, an amino group, a cyano group, an alkoxyl group (preferably having from 1 to 5 carbon atoms), a cycloalkyl group (preferably having from 3 to 15 carbon atoms), an aryl group (preferably having from 6 to 14 carbon atoms), an alkoxycarbonyl group (preferably having from 2 to 7 carbon atoms), an acyl group (preferably having from 2 to 12 carbon atoms), and an alkoxycarbonyloxy group (preferably having from 2 to 7 carbon atoms) are exemplified. With respect to the aryl group and the cyclic structure of each group, an alkyl group (preferably having from 1 to 15 carbon atoms) can be further exemplified as the substituent.

As the alkyl moiety in an alkyl carboxylate anion, the same alkyl group and cycloalkyl group as in the alkyl sulfonate anion can be exemplified.

As the aryl moiety in an aryl carboxylate anion, the same aryl group as in the aryl sulfonate anion can be exemplified.

As the aralkyl group in an aralkylcarboxylate anion, preferably an aralkyl group having from 6 to 12 carbon atoms, e.g., a benzyl group, a phenethyl group, a naphthylmethyl group, a naphthylethyl group, and a naphthylmethyl group can be exemplified.

As the substituents of the alkyl group, cycloalkyl group, aryl group and aralkyl groups in the alkyl carboxylate anion, aryl carboxylate anion and aralkylcarboxylate anion, e.g., the same halogen atom, alkyl group, cycloalkyl group, alkoxyl group and alkylthio group as in the aryl sulfonate anion can be exemplified.

As a sulfonylimide anion, e.g., a saccharin anion can be exemplified.

The alkyl group in a bis(alkylsulfonyl)imide anion, and a tris(alkylsulfonyl)methyl anion is preferably an alkyl group having from 1 to 5 carbon atoms, e.g., a methyl group, an ethyl group, a propyl group, an isopropyl group, an n-butyl group, an isobutyl group, a sec-butyl group, a pentyl group and a neopentyl group are exemplified. As the substituents of these alkyl groups, a halogen atom, an alkyl group substituted with a halogen atom, an alkoxyl group, and an alkylthio group can be exemplified, and an alkyl group substituted with a fluorine atom is preferred.

As other non-nucleophilic anions, e.g., fluorinated phosphorus, fluorinated boron and fluorinated antimony can be exemplified.

As the non-nucleophilic anions represented by $Z^-$, an alkane sulfonate anion in which the α-position of the sulfonic acid is substituted with a fluorine atom, an aryl sulfonate anion substituted with a fluorine atom or a group having a fluorine atom, a bis(alkylsulfonyl)imide anion in which the alkyl group is substituted with a fluorine atom, and a tris(alkylsulfonyl)methide anion in which the alkyl group is substituted with a fluorine atom are preferred. Especially preferred non-nucleophilic anions are an alkane perfluorosulfonate anion having from 4 to 8 carbon atoms and a benzenesulfonate anion having a fluorine atom, and most preferred non-nucleophilic anions are a nonafluorobutanesulfonate anion, a perfluorooctanesulfonate anion, a pentafluorobenzenesulfonate anion, and a 3,5-bis(trifluoro-methyl)benzenesulfonate anion.

As the specific examples of the organic groups represented by $R_{201}$, $R_{202}$ and $R_{203}$, the corresponding groups in the later-described compounds represented by formula (ZI-1), (ZI-2) or (ZI-3) can be exemplified.

A compound represented by formula (ZI) may be a compound having a plurality of structures represented by formula (ZI). For instance, compound (ZI) may be a compound having a structure that at least one of $R_{201}$, $R_{202}$ and $R_{203}$ of a compound represented by formula (ZI) is bonded to at least one of $R_{201}$, $R_{202}$ and $R_{203}$ of another compound represented by formula (ZI).

The following compounds (ZI-1), (ZI-2) and (ZI-3) can be exemplified as more preferred components (ZI).

Compound (ZI-1) is an arylsulfonium compound that at least one of $R_{201}$ to $R_{203}$ in formula (ZI) represents an aryl group, i.e., a compound having arylsulfonium as a cation.

All of $R_{201}$ to $R_{203}$ of the arylsulfonium compound may be aryl groups, or a part of $R_{201}$ to $R_{203}$ may represent an aryl group and the remainder may represent an alkyl group or a cycloalkyl group.

As the arylsulfonium compounds, e.g., a triarylsulfonium compound, a diarylalkylsulfonium compound, an aryldialkyl-sulfonium compound, a diarylcycloalkylsulfonium compound, and an aryldicycloalkylsulfonium compound are exemplified.

As the aryl groups of the arylsulfonium compound, a phenyl group and a naphthyl group are preferred, and the more preferred group is a phenyl group. When the arylsulfonium compound has two or more aryl groups, these two or more aryl groups may be the same or different.

As an alkyl group or a cycloalkyl group that the arylsulfonium compound has according to necessity, a straight chain or branched alkyl group having from 1 to 15 carbon atoms and a cycloalkyl group having from 3 to 15 carbon atoms are preferred, e.g., a methyl group, an ethyl group, a propyl group, an n-butyl group, a sec-butyl group, a t-butyl group, a cyclopropyl group, a cyclobutyl group and a cyclohexyl group can be exemplified.

The aryl group, alkyl group and cycloalkyl group represented by $R_{201}$, $R_{202}$ and $R_{203}$ may have a substituent and, e.g., an alkyl group (e.g., having from 1 to 15 carbon atoms), a cycloalkyl group (e.g., having from 3 to 15 carbon atoms), an aryl group (e.g., having from 6 to 14 carbon atoms), an alkoxyl group (e.g., having from 1 to 15 carbon atoms), a halogen atom, a hydroxyl group, and a phenylthio group are exemplified. The preferred substituents are a straight chain or branched alkyl group having from 1 to 12 carbon atoms, a cycloalkyl group having from 3 to 12 carbon atoms, and a straight chain, branched or cyclic alkoxyl group having from 1 to 12 carbon atoms, and the most preferred substituents are an alkyl group having from 1 to 4 carbon atoms and an alkoxyl group having from 1 to 4 carbon atoms. The substituent may be substituted on any one of three of $R_{201}$ to $R_{203}$, or may be substituted on all of three. When $R_{201}$, $R_{202}$ and $R_{203}$ each represents an aryl group, it is preferred that the substituent be substituted on the p-position of the aryl group.

Compound (ZI-2) is described below.

Compound (ZI-2) is a compound in the case where $R_{201}$, $R_{202}$ and $R_{203}$ in formula (ZI) each represents an organic group not containing an aromatic ring. The aromatic ring also includes an aromatic ring containing a hetero atom.

The organic groups not containing an aromatic ring represented by $R_{201}$ to $R_{203}$ generally have from 1 to 30 carbon atoms, preferably from 1 to 20 carbon atoms.

$R_{201}$, $R_{202}$ and $R_{203}$ each preferably represents an alkyl group, a cycloalkyl group, an allyl group, or a vinyl group, more preferably a straight chain or branched 2-oxoalkyl group, a 2-oxocycloalkyl group or an alkoxycarbonylmethyl group, and particularly preferably a straight or branched 2-oxoalkyl group.

The alkyl group and cycloalkyl group represented by $R_{201}$ to $R_{203}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbonyl group). The alkyl group is more preferably a 2-oxoalkyl group or an alkoxycarbonylmethyl group. The cycloalkyl group is more preferably a 2-oxocycloalkyl group.

The 2-oxoalkyl group may be either a straight chain or branched group, and a group having >C=O on the 2-position of the above alkyl group can be exemplified as a preferred group.

The 2-oxocycloalkyl group is preferably a group having >C=O on the 2-position of the above cycloalkyl group.

As the alkoxyl group in the alkoxycarbonylmethyl group, an alkoxyl group preferably having from 1 to 5 carbon atoms (e.g., a methoxy group, an ethoxy group, a propoxy group, a butoxy group, a pentoxy group) can be exemplified.

$R_{201}$ to $R_{203}$ may further be substituted with a halogen atom, an alkoxyl group (e.g., having from 1 to 5 carbon atoms), a hydroxyl group, a cyano group or a nitro group.

Two of $R_{201}$ to $R_{203}$ may combine from each other to form a ring, which may contain an oxygen atom, sulfur atom, ester bond, amide bond or carbonyl group. As the group formed by combination of two of $R_{201}$ to $R_{203}$, an alkylene group such as butylenes group and pentylene group is exemplified.

Compound (ZI-3) is a compound represented by the following formula (ZI-3), which compound has a phenacyl-sulfonium salt structure.

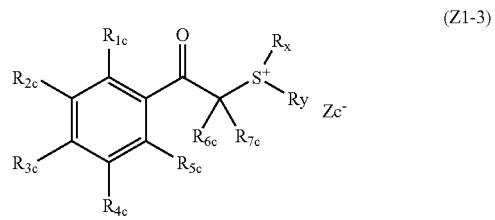

In formula (ZI-3), $R_{1c}$, $R_{2c}$, $R_{3c}$, $R_{4c}$ and $R_{5c}$ each represents a hydrogen atom, an alkyl group, a cycloalkyl group, an alkoxyl group or a halogen atom.

$R_{6c}$ and $R_{7c}$ each represents a hydrogen atom, an alkyl group or a cycloalkyl group.

$R_x$ and $R_y$ each represents an alkyl group, a cycloalkyl group, an allyl group or a vinyl group.

Any two or more of $R_{1c}$ to $R_{5c}$, $R_{6c}$ and $R_{7c}$, and $R_x$ and $R_y$ may be bonded to each other to form a cyclic structure. As the groups formed by the bonding of these groups, a butylene group and a pentylene group can be exemplified. An oxygen atom, a sulfur atom, an ester bond or an amide bond may be contained in the cyclic structure.

$Z_c^-$ represents a non-nucleophilic anion, and the same anion as the non-nucleophilic anion represented by $X^-$ in formula (ZI) can be exemplified.

The alkyl groups represented by $R_{1c}$ to $R_{7c}$ may be either straight chain or branched, e.g., a straight chain or branched alkyl group having from 1 to 20 carbon atoms, preferably from 1 to 12 carbon atoms (e.g., a methyl group, an ethyl group, a straight chain or branched propyl group, a straight chain or branched butyl group, a straight chain or branched pentyl group) can be exemplified. As the cycloalkyl groups represented by $R_{1c}$ to $R_{7c}$, a cycloalkyl group having from 3 to 8 carbon atoms (e.g., a cyclopentyl group and a cyclohexyl group) can be exemplified.

The alkoxyl groups represented by $R_{1c}$ to $R_{7c}$ may be any of straight chain, branched and cyclic, e.g., an alkoxyl group having from 1 to 10 carbon atoms, a straight chain or branched alkoxyl group having from 1 to 5 carbon atoms (e.g., a methoxy group, an ethoxy group, a straight chain or branched propoxy group, a straight chain or branched butoxy group, a straight chain or branched pentoxy group), a cyclic alkoxyl group having from 3 to 8 carbon atoms (e.g., a cyclopentyloxy group and a cyclohexyloxy group) can be exemplified.

It is preferred that any of $R_{1c}$ to $R_{5c}$ represents a straight chain or branched alkyl group, a cycloalkyl group, or a straight chain, branched or cyclic alkoxyl group, it is more preferred that the sum total of the carbon atoms of $R_{1c}$ to $R_{5c}$ is from 2 to 15, by which the solubility in a solvent increases and generation of particles during preservation can be restrained.

As the alkyl group and cycloalkyl group represented by $R_x$ and $R_y$, the same alkyl groups and cycloalkyl groups represented by $R_{1c}$ to $R_{7c}$ can be exemplified, and a 2-oxoalkyl group, a 2-oxocycloalkyl group and an alkoxycarbonylmethyl group are more preferred.

As the 2-oxoalkyl group and the 2-oxocycloalkyl group, groups having >C=O on the 2-position of the alkyl group and the cycloalkyl group represented by $R_{1c}$ to $R_{7c}$ can be exemplified.

As the alkoxyl group of the alkoxycarbonylmethyl group, the same alkoxyl groups as those represented by $R_{1c}$ and $R_{5c}$ can be exemplified.

Examples of the group formed by combining $R_x$ and $R_y$ include a butylene group and a pentylene group.

$R_x$ and $R_y$ each preferably represents an alkyl group or a cycloalkyl group having 4 or more carbon atoms, more preferably an alkyl group or a cycloalkyl group having 6 or more carbon atoms, and still more preferably an alkyl group or a cycloalkyl group having 8 or more carbon atoms.

In formulae (ZII) and (ZIII), $R_{204}$, $R_{205}$, $R_{206}$ and $R_{207}$ each represents an aryl group, an alkyl group or a cycloalkyl group.

The aryl group represented by $R_{204}$ to $R_{207}$ is preferably a phenyl group or a naphthyl group, and more preferably a phenyl group.

The alkyl group and the cycloalkyl group represented by $R_{204}$ to $R_{207}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbonyl group).

As the substituents that the groups represented by $R_{204}$ to $R_{207}$ may have, e.g., an alkyl group (e.g., having from 1 to 15 carbon atoms), a cycloalkyl group (e.g., having from 3 to 15 carbon atoms), an aryl group (e.g., having from 6 to 15 carbon atoms), an alkoxyl group (e.g., having from 1 to 15 carbon atoms), a halogen atom, a hydroxyl group and a phenylthio group can be exemplified.

$X^-$ represents a non-nucleophilic anion, and the same non-nucleophilic anions as those represented by $X^-$ in formula (ZI) can be exemplified.

As the acid generators that can be used in combination, the compounds represented by the following formula (ZIV), (ZV) or (ZVI) can further be exemplified.

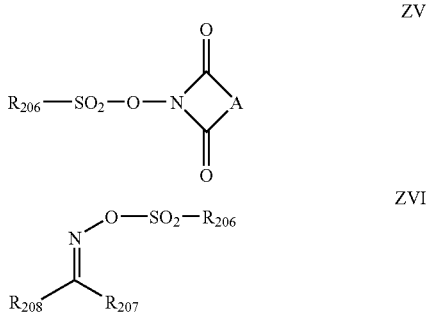

In formulae (ZIV), (ZV) and (ZVI), $Ar_3$ and $Ar_4$ each represents an aryl group.

$R_{206}$, $R_{207}$ and $R_{208}$ each represents an alkyl group, a cycloalkyl group or an aryl group.

A represents an alkylene group, an alkenylene group or an arylene group.

Of the acid generators that can be used in combination, more preferred compounds are the compounds represented by formulae (ZI), (ZII) and (ZIII).

Further, as the acid generators usable in combination, a compound generating a sulfonic acid having one sulfonic acid group is preferred, and a compound generating a monovalent perfluoroalkanesulfonic acid, and a compound generating an aromatic sulfonic acid substituted with a fluorine atom or a group containing a fluorine atom are more preferred, and a sulfonium salt of a monovalent perfluoroalkanesulfonic acid is particularly preferred.

Of the acid generators that can be used in combination, particularly preferred examples are shown below.

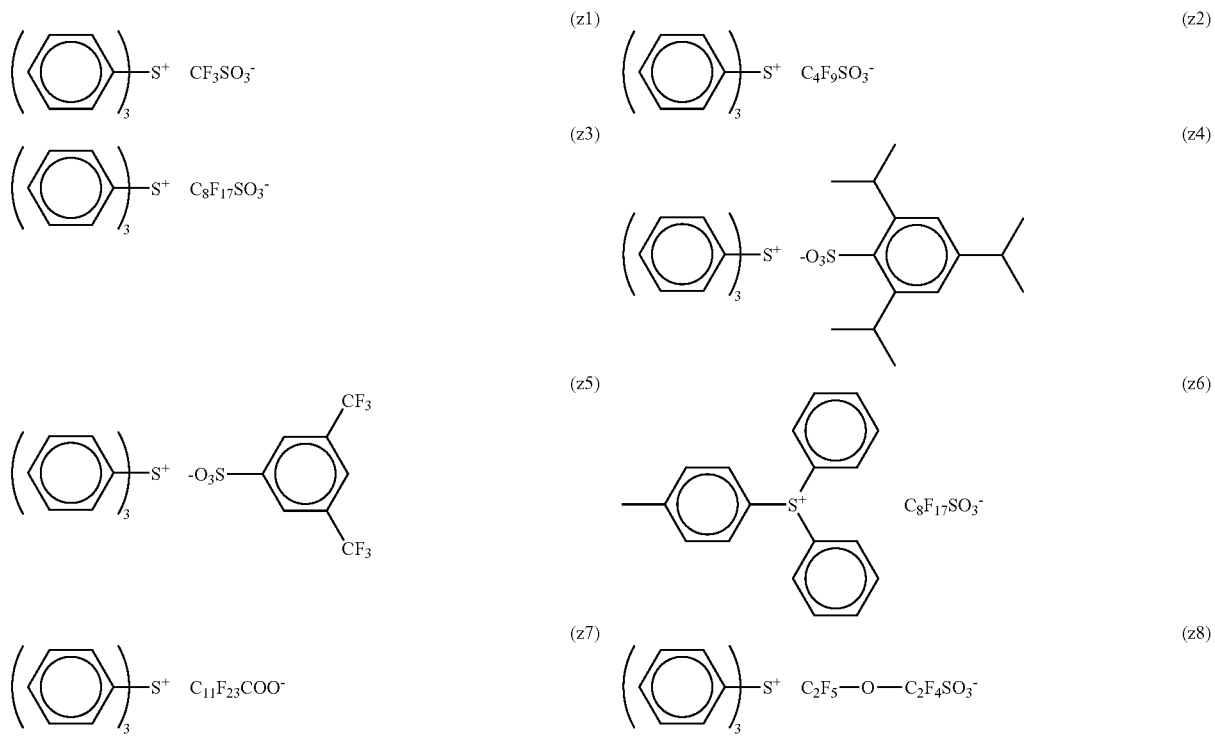

-continued
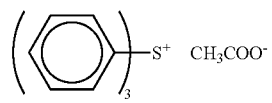 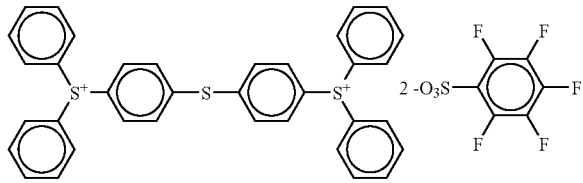
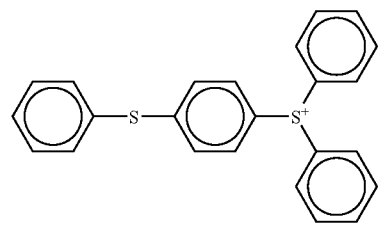 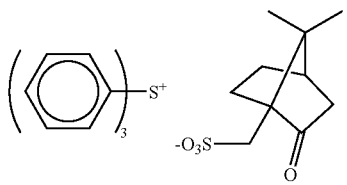
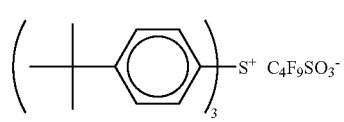 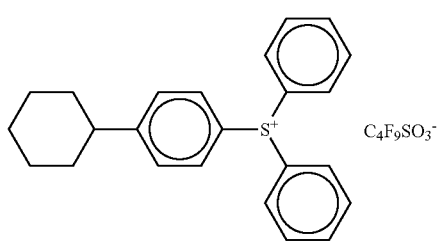
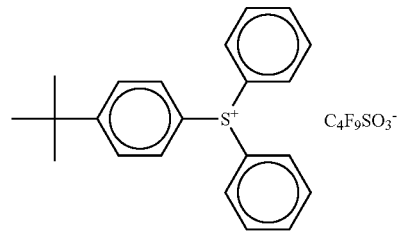 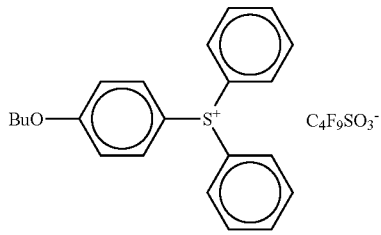
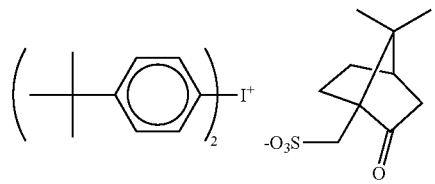 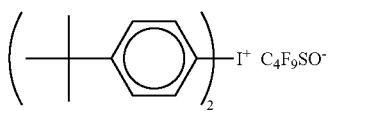
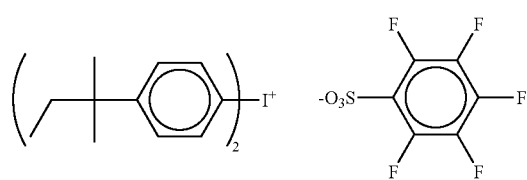 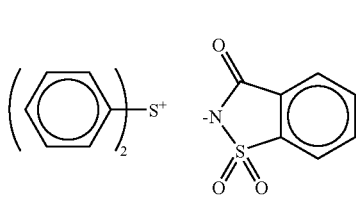
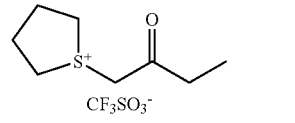 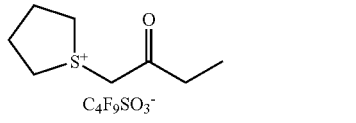
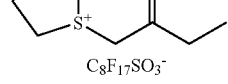 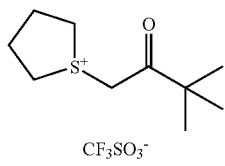

-continued
(z25) 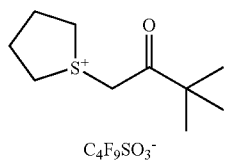
(z26) 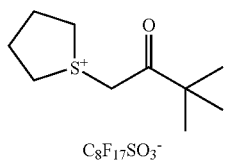
(z27) 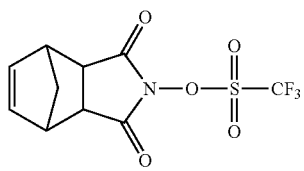
(z28) 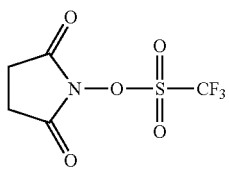
(z29) 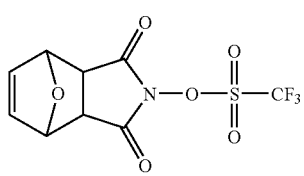
(z30) 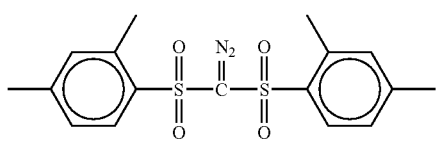
(z31) 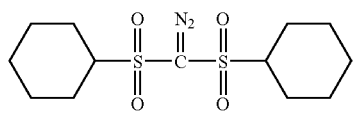
(z32) 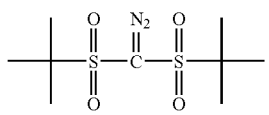
(z33) 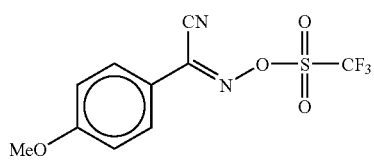
(z34) 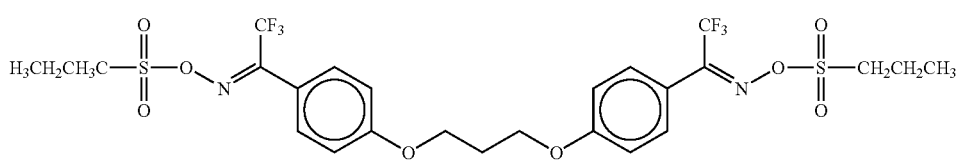
(z35) 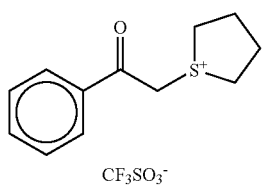
(z36) 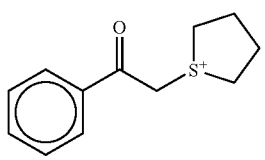
(z37) 
(z38) 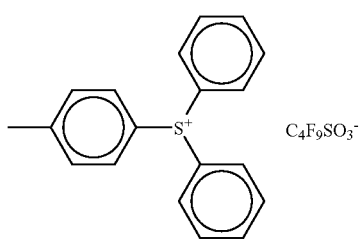

-continued
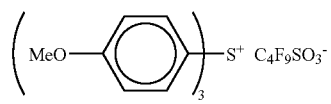 (z39)
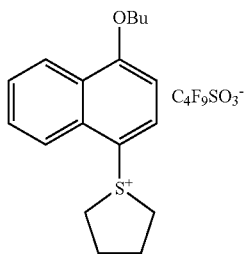 (z40)
 (z41)
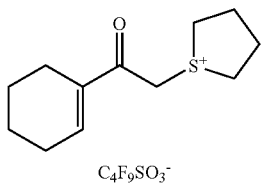 (z42)
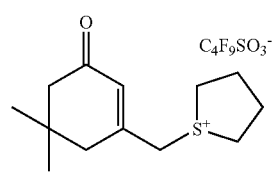 (z43)
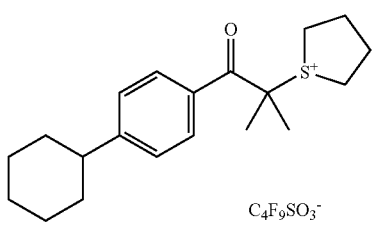 (z44)
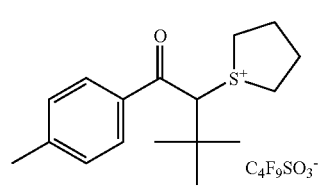 (z45)
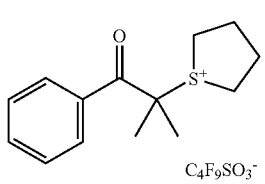 (z46)
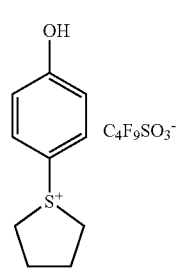 (z47)
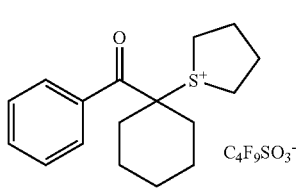 (z48)
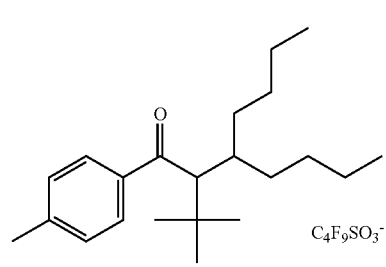 (z49)
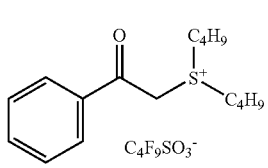 (z50)
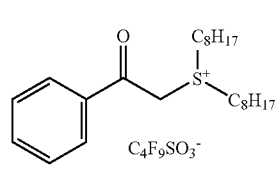 (z51)
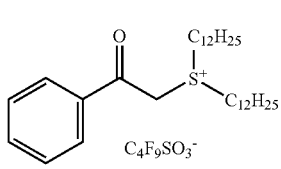 (z52)

-continued

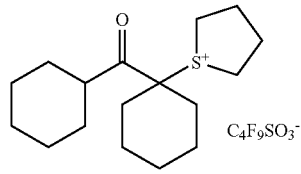 (z53)

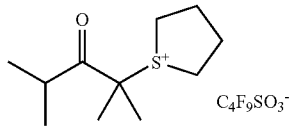 (z54)

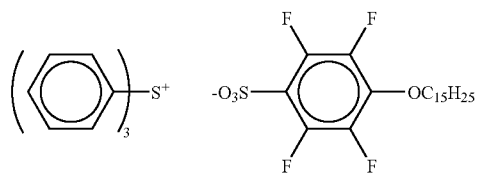 (z55)

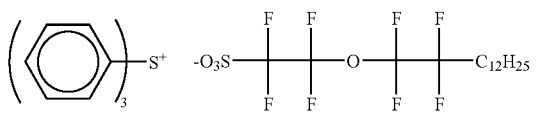 (z56)

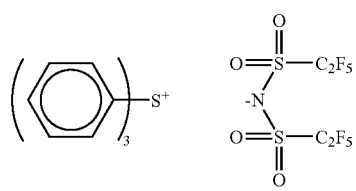 (z57)

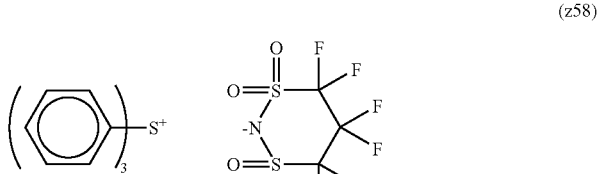 (z58)

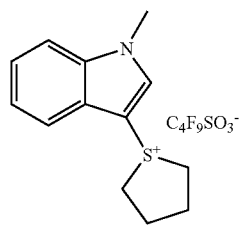 (z59)

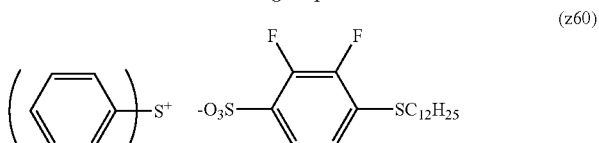 (z60)

(z61)

[2] (B) A Resin Decomposable by the Action of an Acid and Increasing the Solubility in an Alkali Developer (Hereinafter also Referred to as Component (B)):

A resin capable of decomposing by the action of an acid and increasing the solubility in an alkali developer for use in the positive photosensitive composition in the invention is a resin having a group decomposable by the action of an acid (hereinafter referred to as "an acid-decomposable group") on the main chain or side chain of the resin, or on both the main chain and side chain. A resin having a group decomposable by the action of an acid on the side chain is more preferred.

A preferred acid-decomposable group is a group obtained by substituting the hydrogen atom of a —COOH group or an —OH group with a group capable of being desorbed by an acid.

A particularly preferred acid-decomposable group in the invention is an acetal group or a tertiary ester group.

The parent resins in the case where the acid-decomposable group is bonded as the side chain are alkali-soluble resins having an —OH group or a —COOH group on the side chain. For example, the later-described alkali-soluble resins can be exemplified.

The alkali dissolution rate of these alkali-soluble resins is preferably 170 Å/sec or more when measured using 0.261N tetramethylammonium hydroxide (TMAH) at 23° C., particularly preferably 330 Å/sec or more.

From this point of view, particularly preferred alkali-soluble resins are alkali-soluble resins having a hydroxystyrene structural unit such as o-, m-, p-poly(hydroxystyrene) and copolymers thereof, hydrogenated poly(hydroxystyrene), halogen- or alkyl-substituted poly(hydroxystyrene), a partially O-alkylated or O-acylated product of poly-(hydroxystyrene), styrene-hydroxystyrene copolymers, α-methylstyrene-hydroxystyrene copolymers, and hydrogenated novolak resins.

As repeating units having a preferred acid-decomposable group, e.g., t-butoxycarbonyloxystyrene, 1-alkoxyethoxystyrene, and (meth)acrylic acid tertiary alkyl ester are exemplified, and 2-alkyl-2-adamantyl(meth)acrylate and dialkyl (1-adamantyl)methyl(meth)acrylate are more preferred.

Components (B) for use in the invention can be obtained, as disclosed in EP-254853, JP-A-2-25850, JP-A-3-223860 and JP-A-4-251259, by reacting an alkali-soluble resin with the precursor of an acid-decomposable group, or polymerizing an alkali-soluble resin monomer bonded with an acid-decomposable group with various monomers.

The specific examples of components (B) for use in the invention are shown below, but the invention is not limited thereto.

p-t-Butoxystyrene/p-hydroxystyrene copolymer,
p-(t-Butoxycarbonyloxy)styrene/p-hydroxystyrene copolymer,
p-(t-Butoxycarbonylmethyloxy)styrene/p-hydroxystyrene copolymer,
4-(t-Butoxycarbonylmethyloxy)-3-methylstyrene/4-hydroxy-3-methylstyrene copolymer,
p-(t-Butoxycarbonylmethyloxy)styrene/p-hydroxystyrene (10% hydrogenated product) copolymer,
m-(t-Butoxycarbonylmethyloxy)styrene/m-hydroxystyrene copolymer,
o-(t-Butoxycarbonylmethyloxy)styrene/o-hydroxystyrene copolymer,
p-(Cumyloxycarbonylmethyloxy)styrene/p-hydroxystyrene copolymer,
Cumyl methacrylate/methyl methacrylate copolymer,
4-t-Butoxycarbonylstyrene/dimethyl maleate copolymer,
Benzyl methacrylate/tetrahydropyranyl methacrylate copolymer,
p-(t-Butoxycarbonylmethyloxy)styrene/p-hydroxystyrene/styrene copolymer,
p-t-Butoxystyrene/p-hydroxystyrene/fumaronitrile copolymer,
t-Butoxystyrene/hydroxyethyl methacrylate copolymer,
Styrene/N-(4-hydroxyphenyl)maleimide/N-(4-t-butoxy-carbonyloxyphenyl)maleimide copolymer,
p-Hydroxystyrene/t-butyl methacrylate copolymer,
Styrene/p-hydroxystyrene/t-butyl methacrylate copolymer,
p-Hydroxystyrene/t-butyl acrylate copolymer,
Styrene/p-hydroxystyrene/t-butyl acrylate copolymer,
p-(t-Butoxycarbonylmethyloxy)styrene/p-hydroxystyrene/N-methylmaleimide copolymer,
t-Butyl methacrylate/1-adamantyl methyl methacrylate copolymer,
p-Hydroxystyrene/t-butyl acrylate/p-acetoxystyrene copolymer,
p-Hydroxystyrene/t-butyl acrylate/p-(t-butoxycarbonyl-oxy)styrene copolymer,
p-Hydroxystyrene/t-butyl acrylate/p-(t-butoxycarbonyl-methyloxy)styrene copolymer.

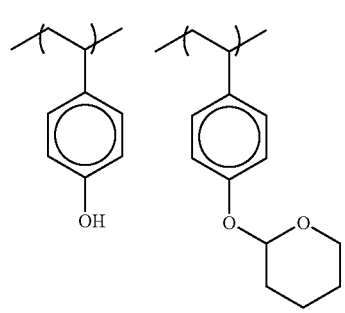

(R-1)

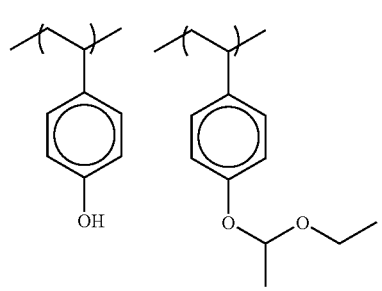

(R-2)

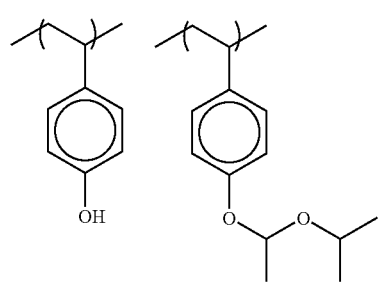

(R-3)

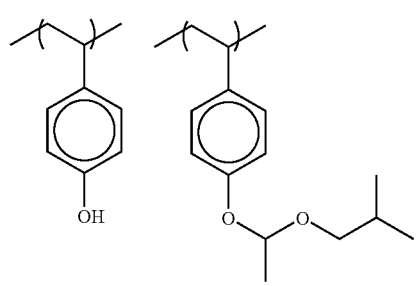

(R-4)

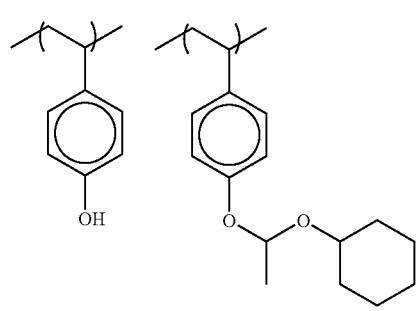

(R-5)

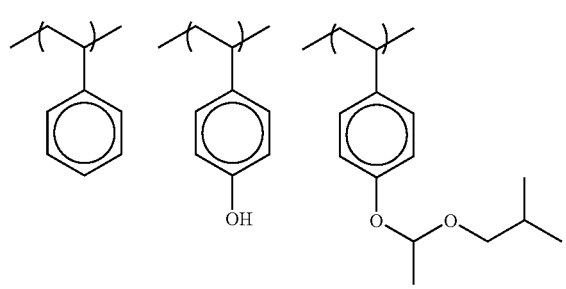

(R-6)

-continued
(R-7) 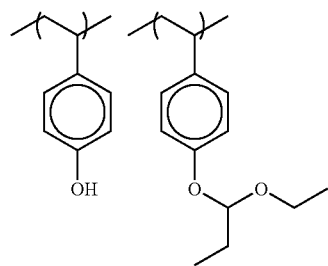
(R-8) 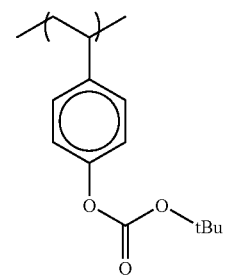
(R-9) 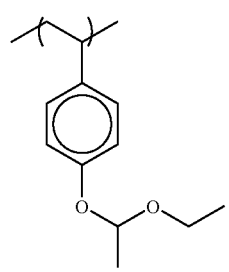 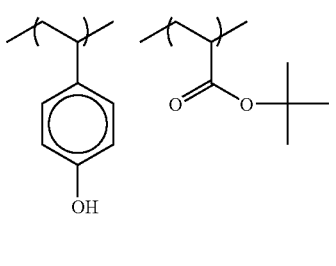
(R-10) 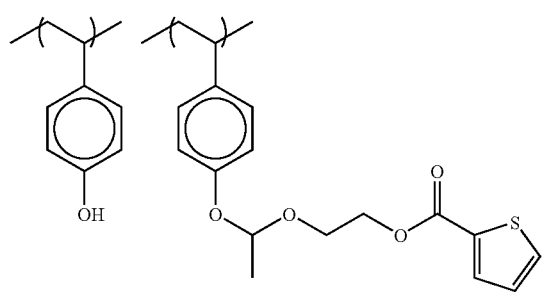
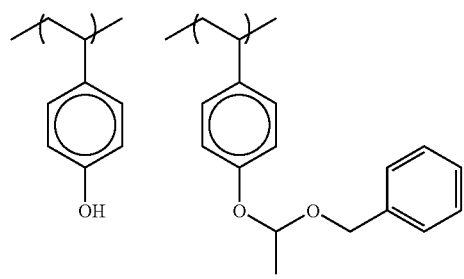
(R11) 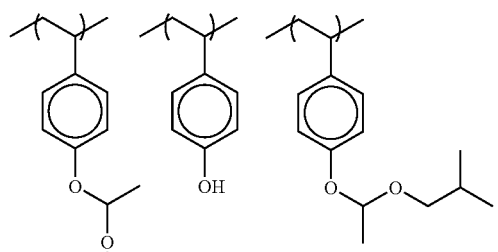
(R12) 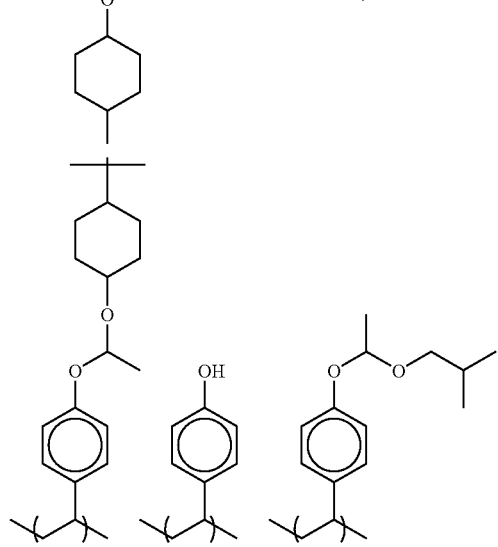

-continued
(R13)
(R14)
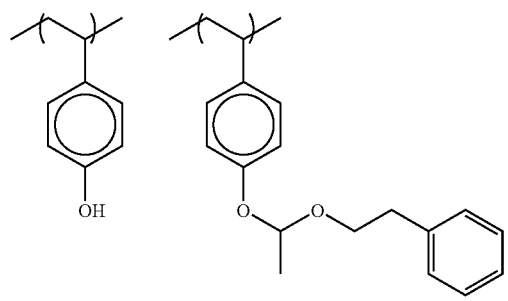
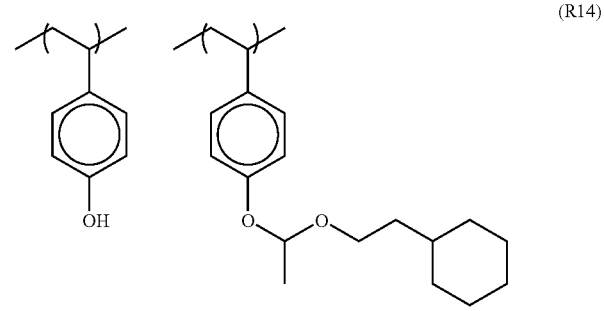
(R-15)
(R-16)
(R-17)
(R-18)
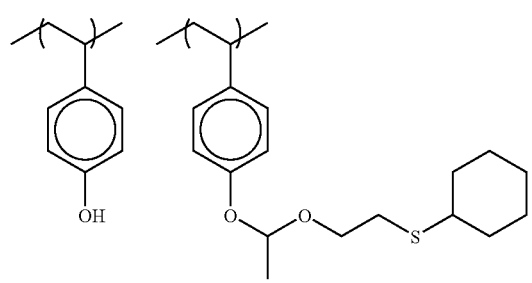
(4-19)
(R-20)
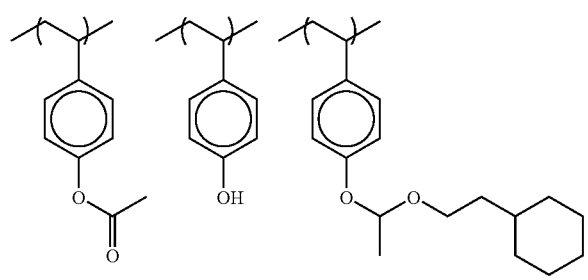
(R-21)
(R-22)
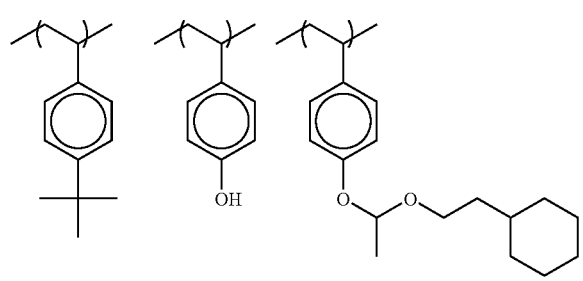
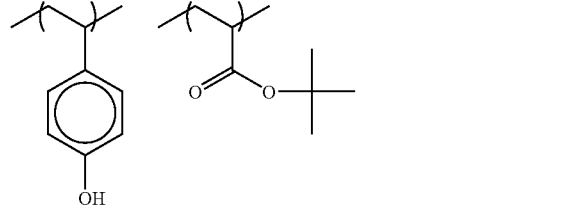

-continued
(R-23) (R-24)
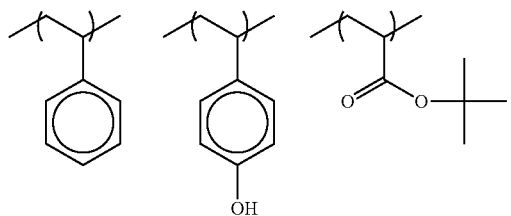 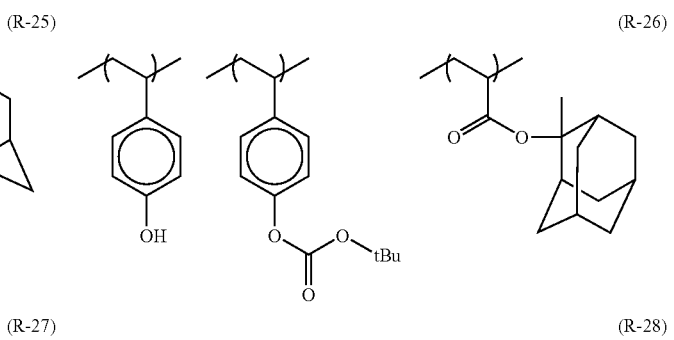
(R-25) (R-26)
(R-27) (R-28)
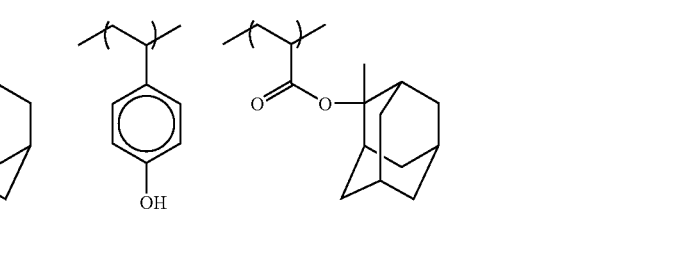
(R-29)
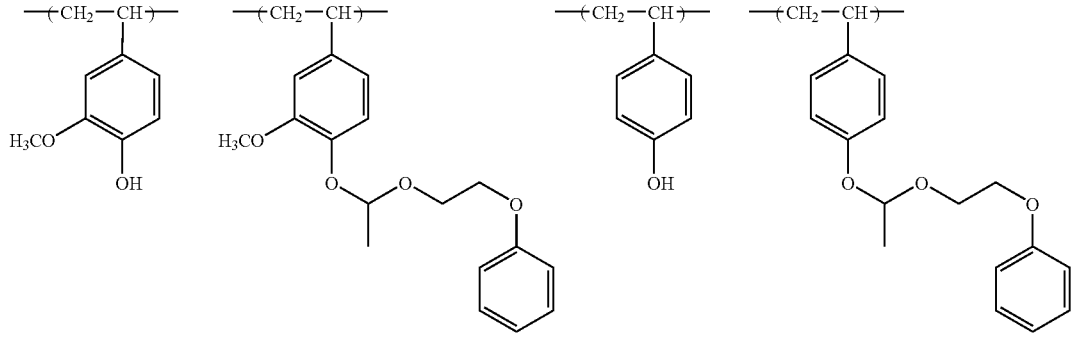
(R-30)
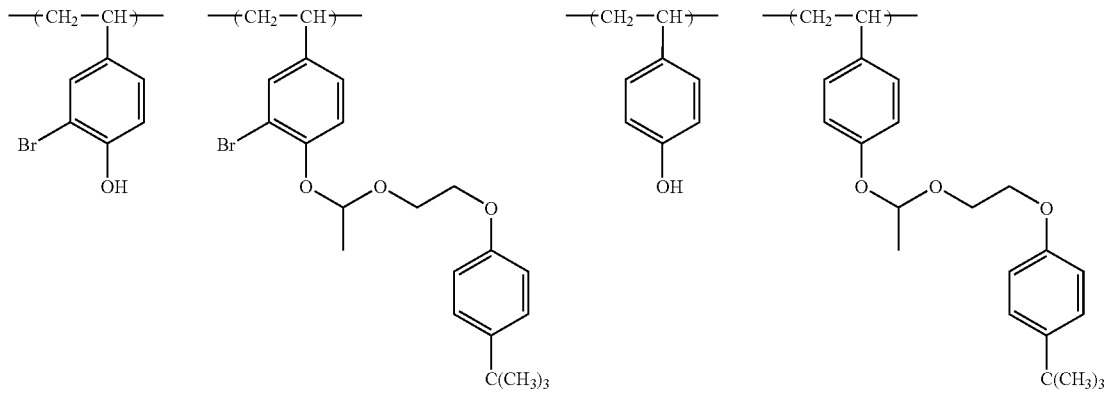

-continued
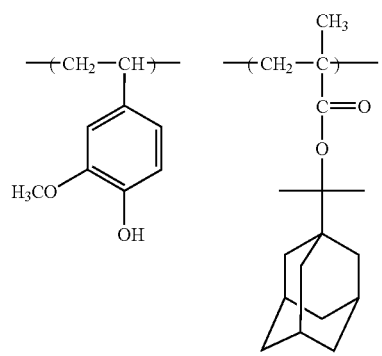 (R-31)
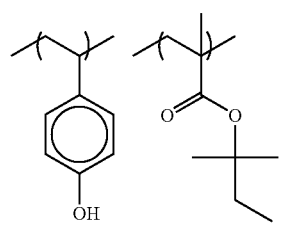 (R-32)
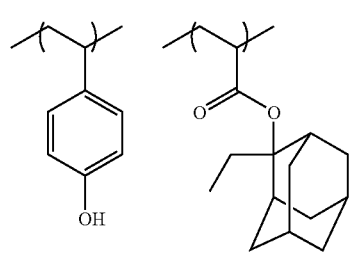 (R-33)
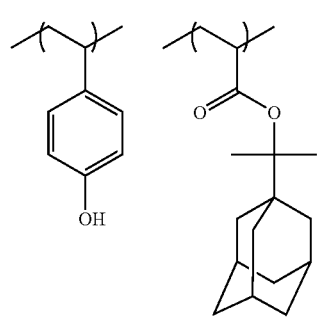 (R-34)
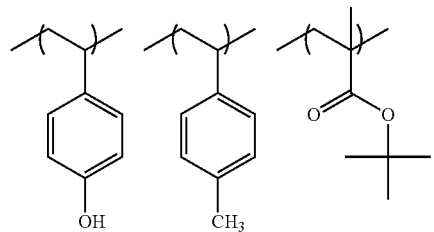 (R-35)
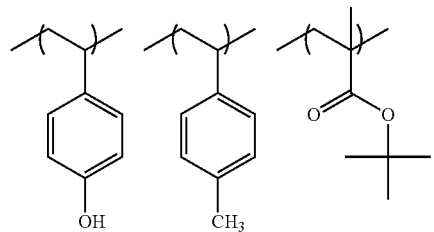 (R-36)
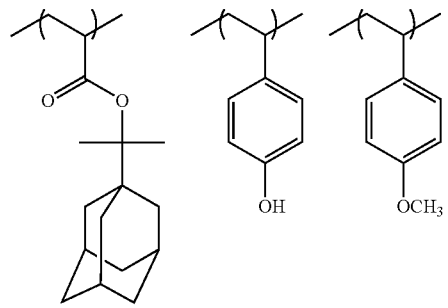 (R-37)
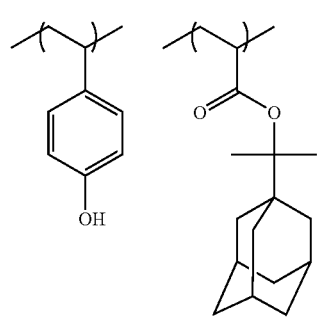 (R-38)
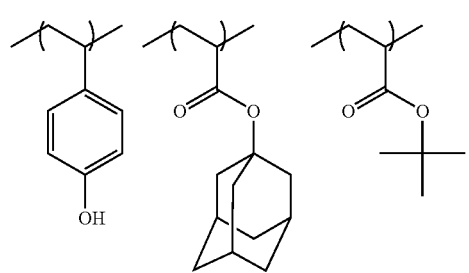 (R-39)
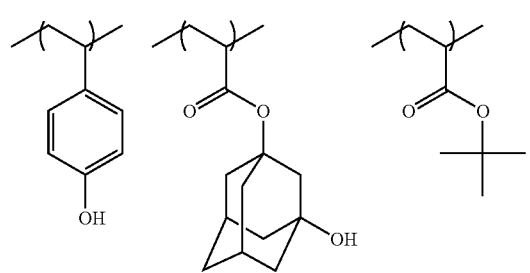 (R-40)

-continued
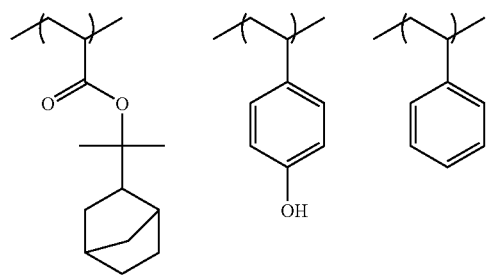 (R-41)
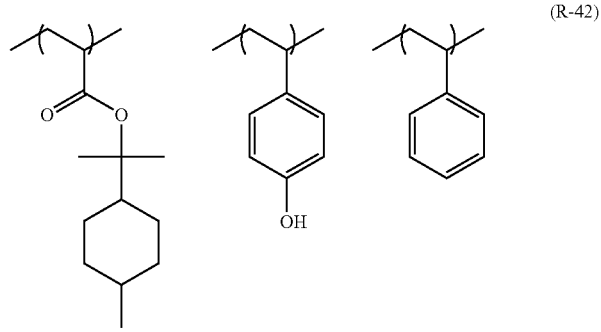 (R-42)
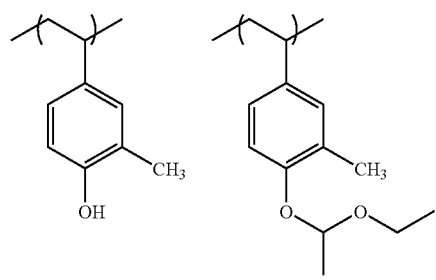 (R-43)
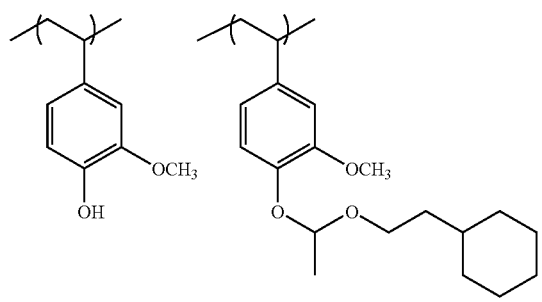 (R-44)
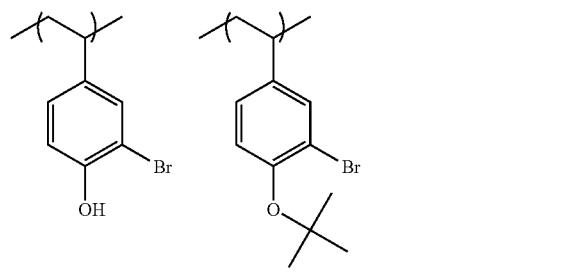 (R-45) (R-47)
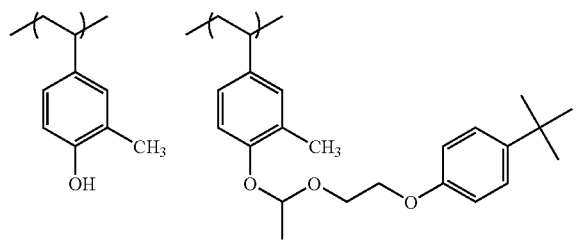 (R-46) (R-48)
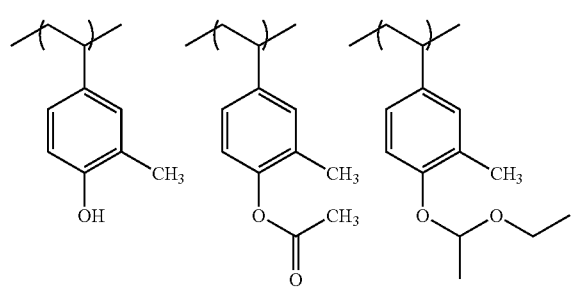 (R-49)

(R-50)
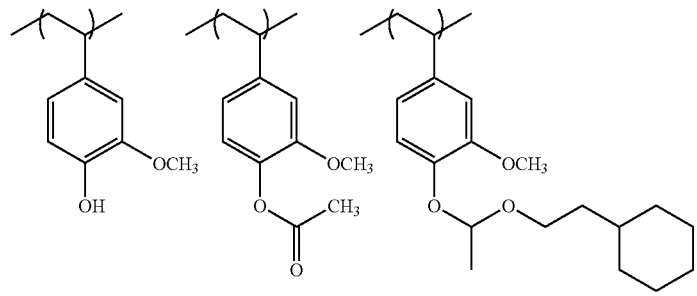
(4-51)
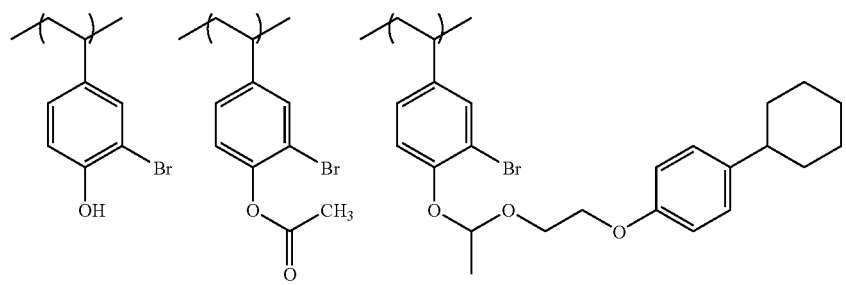
(R-52)
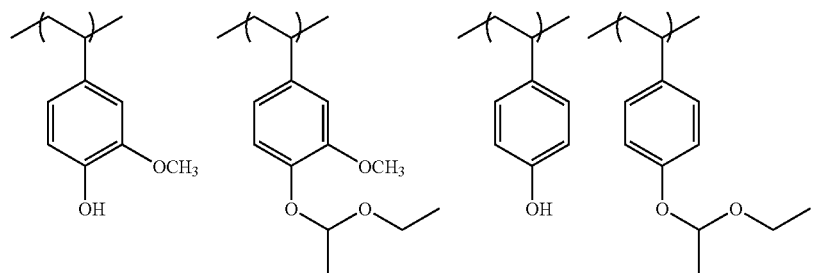
(R-53)
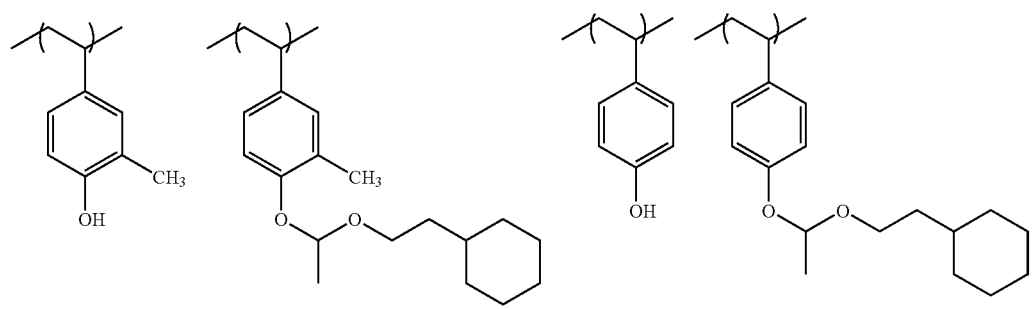
(R-54)
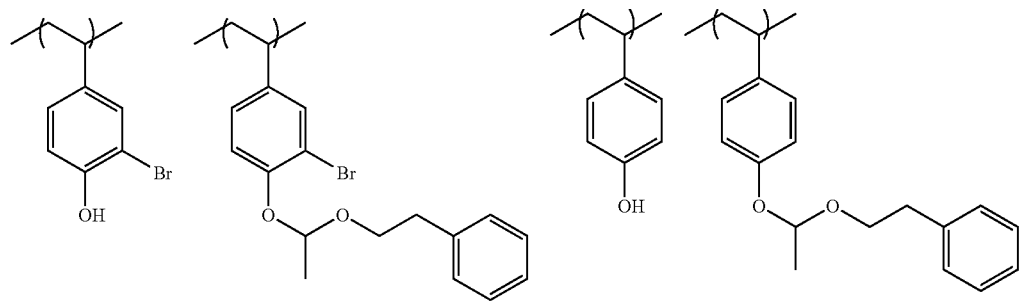

-continued
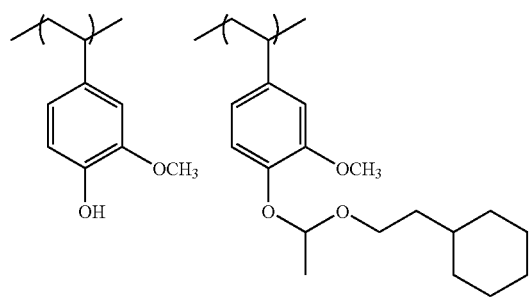
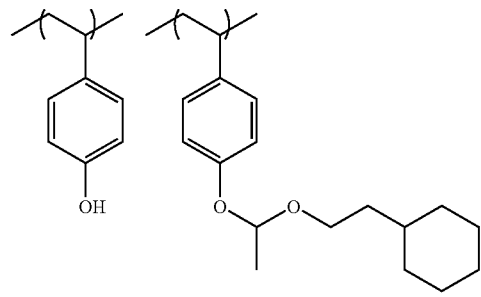
(R-55)
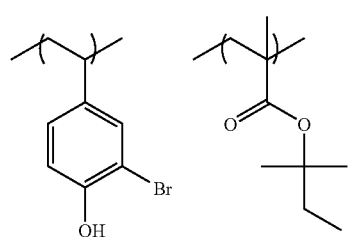
(R-56)
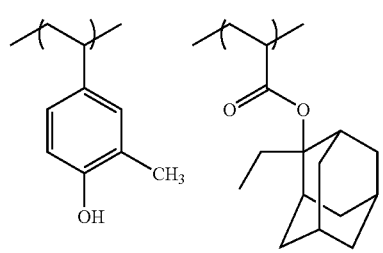
(R-57)
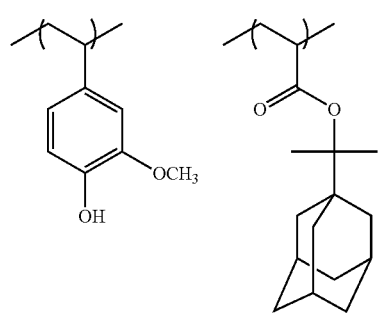
(R-R8)
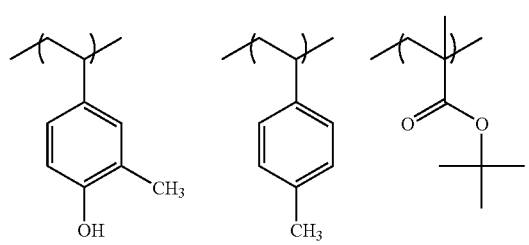
(R-59)
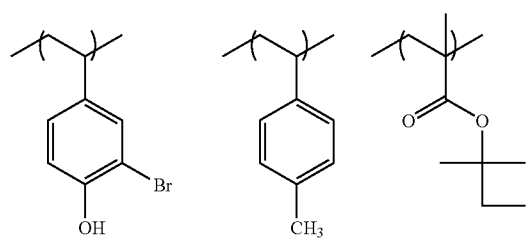
(R-60)
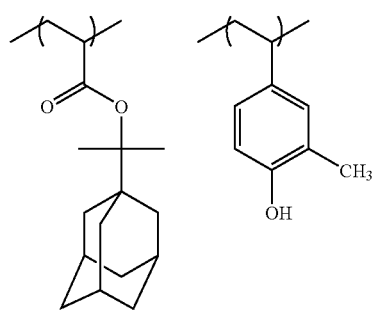
(R-61)
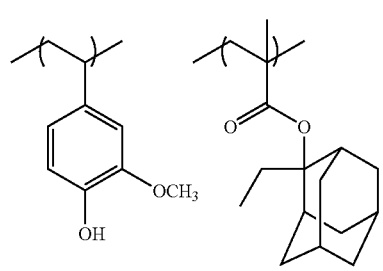
(R-62)
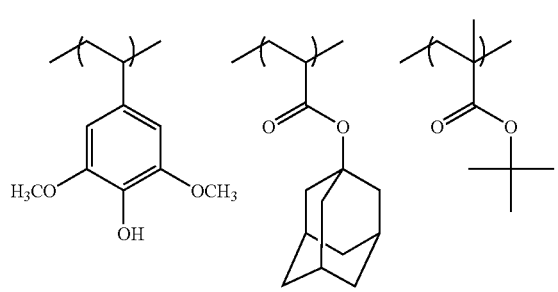
(R-63)

-continued
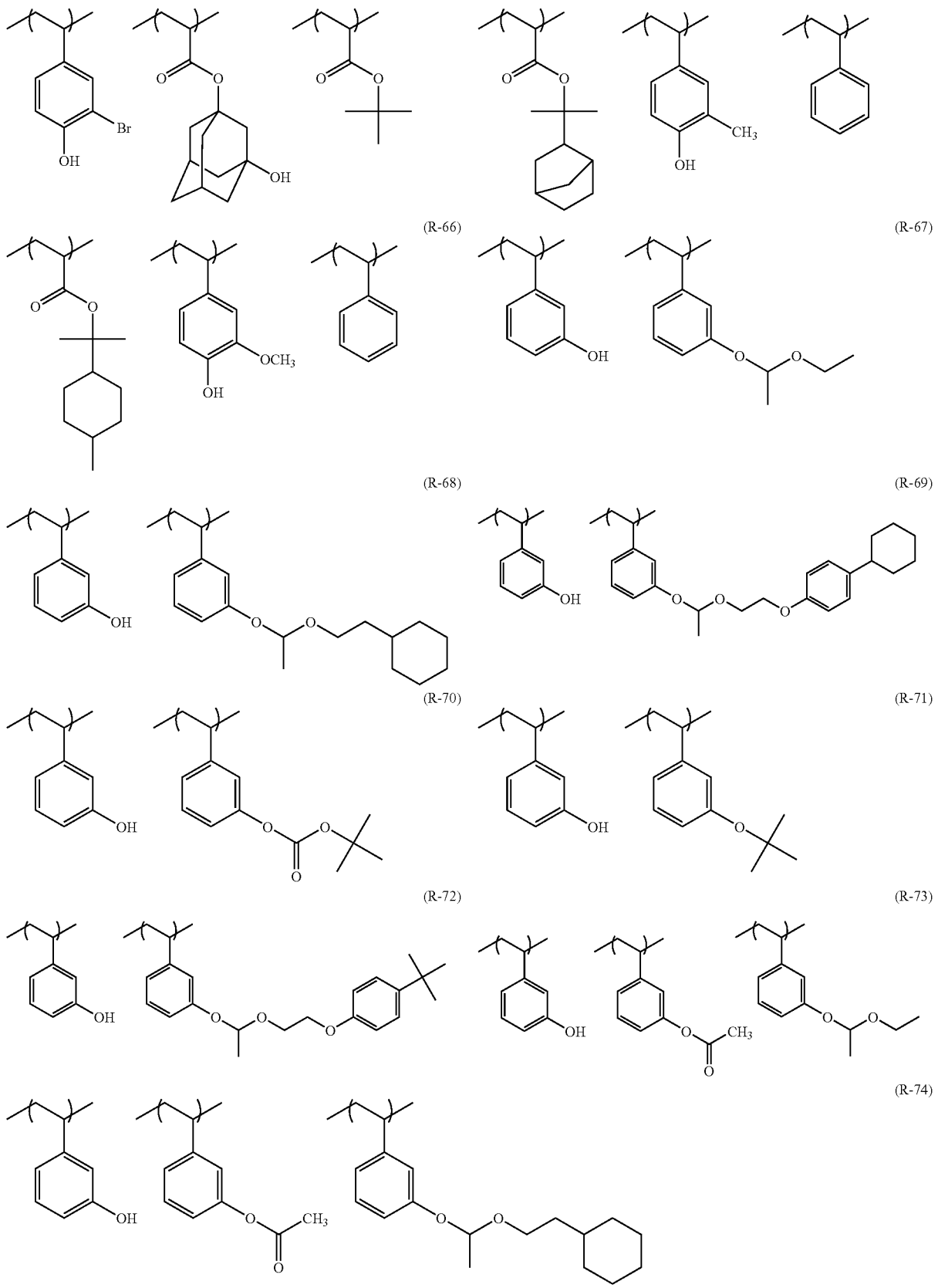

-continued
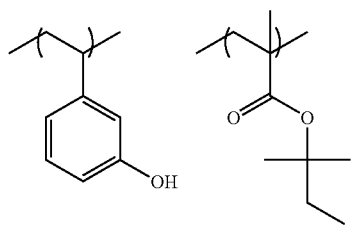
(R-75) (R-76)
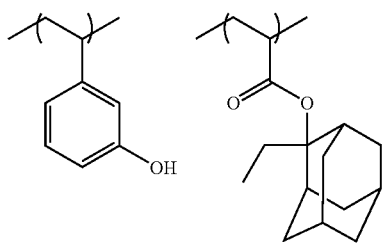
(R-77) (R-78)
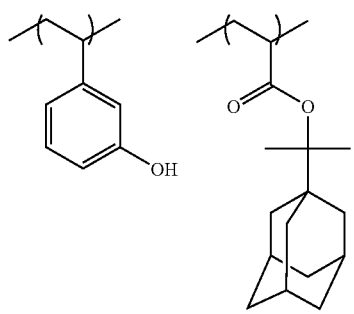
(R-79) (R-80)
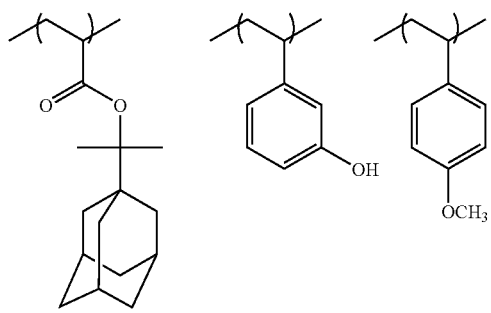
(R-81) (R-82)
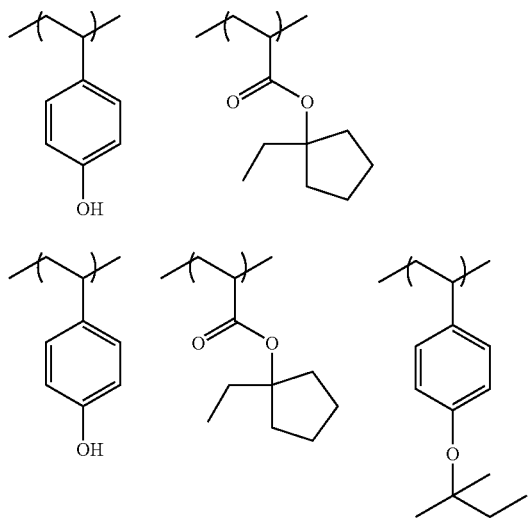
(R-83) (R-84)

-continued

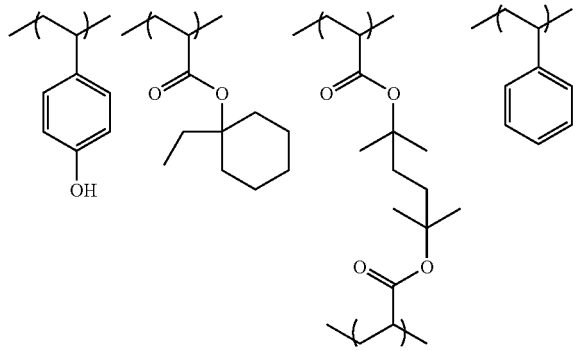
(R-85)

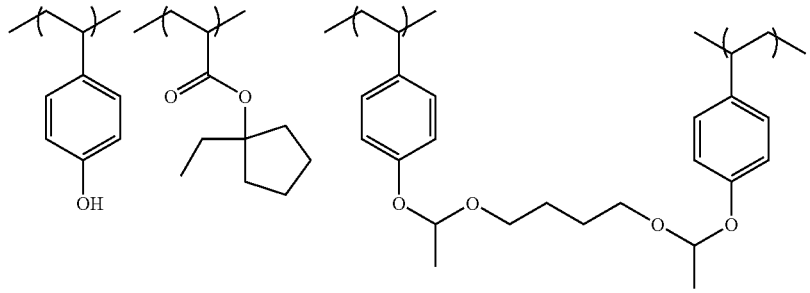
(R-86)

In the above specific examples, tBu means a t-butyl group.

The content of an acid-decomposable group is expressed by the equation of B/(B+S), taking the number of the acid-decomposable groups in a resin as (B), and the number of the alkali-soluble groups not protected with acid-eliminable groups as (S). The content is preferably from 0.01 to 0.7, more preferably from 0.05 to 0.50, and still more preferably from 0.05 to 0.40.

When the positive photosensitive composition in the invention is irradiated with ArF excimer laser beams, it is preferred that the resin of component (B) is a resin having a monocyclic or polycyclic alicyclic hydrocarbon structure and capable of decomposing by the action of an acid to thereby increase the solubility in an alkali developer.

As a resin having a monocyclic or polycyclic alicyclic hydrocarbon structure and capable of decomposing by the action of an acid to thereby increase the solubility in an alkali developer (hereinafter also referred to as "an alicyclic hydrocarbon-based acid-decomposable resin"), a resin containing at least one repeating unit selected from the group consisting of a repeating unit having a partial structure containing alicyclic hydrocarbon represented by any of the following formulae (pI) to (pVI), and a repeating unit represented by the following formula (II-AB) is preferred.

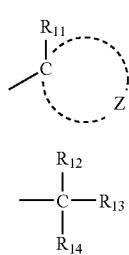

(pI)

(pII)

-continued

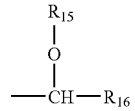
(pIII)

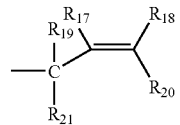
(pIV)

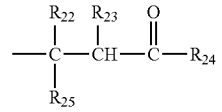
(pV)

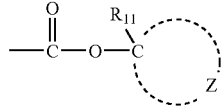
(pVI)

In formulae (pI) to (pVI), $R_{11}$ represents a methyl group, an ethyl group, an n-propyl group, an isopropyl group, an n-butyl group, an isobutyl group, or a sec-butyl group, and Z represents an atomic group necessary to form a cycloalkyl group together with carbon atoms.

$R_{12}$, $R_{13}$, $R_{14}$, $R_{15}$ and $R_{16}$ each represents a straight chain or branched alkyl group having from 1 to 4 carbon atoms, or a cycloalkyl group, provided that at least one of $R_{12}$ to $R_{14}$, or either $R_{14}$ or $R_{15}$ represents a cycloalkyl group.

$R_{17}$, $R_{18}$, $R_{19}$, $R_{20}$ and $R_{21}$ each represents a hydrogen atom, a straight chain or branched alkyl group having from 1 to 4 carbon atoms or a cycloalkyl group, provided that at least one of $R_{17}$ to $R_{21}$ represents a cycloalkyl group, and either $R_{19}$ or $R_{21}$ represents a straight chain or branched alkyl group having from 1 to 4 carbon atoms or a cycloalkyl group.

$R_{22}$, $R_{23}$, $R_{24}$ and $R_{25}$ each represents a hydrogen atom, a straight chain or branched alkyl group having from 1 to 4 carbon atoms or a cycloalkyl group, provided that at least one of $R_{22}$ to $R_{25}$ represents a cycloalkyl group, and $R_{23}$ and $R_{24}$ may be bonded to each other to form a ring.

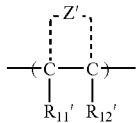

(II-AB)

In formula (II-AB), $R_{11}'$ and $R_{12}'$ each represents a hydrogen atom, a cyano group, a halogen atom or an alkyl group.

$Z'$ contains bonded two carbon atoms (C—C) and represents an atomic group to form an alicyclic structure.

Formula (II-AB) is more preferably represented by the following formula (II-A) or (II-B).

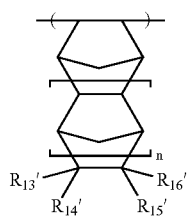

(II-A)

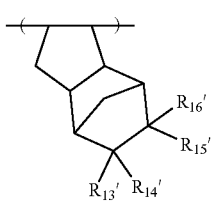

(II-B)

In formulae (II-A) and (II-B), $R_{13}'$, $R_{14}'$, $R_{15}'$ and $R_{16}'$ each represents a hydrogen atom, a halogen atom, a cyano group, —COOH, —COOR$_5$, a group decomposing by the action of an acid, —C(=O)—X-A'-$R_{17}'$, an alkyl group, or a cycloalkyl group.

$R_5$ represents an alkyl group, a cycloalkyl group, or —Y group shown below.

X represents an oxygen atom, a sulfur atom, —NH—, —NHSO$_2$— or —NHSO$_2$NH—.

A' represents a single bond or a divalent linking group.

$R_{17}'$ represents —COOH, —COOR$_5$, —CN, a hydroxyl group, an alkoxyl group, —CO—NH—R$_6$, —CO—NH—SO$_2$—R$_6$, or —Y group shown below.

$R_6$ represents an alkyl group or a cycloalkyl group.

At least two of $R_{13}'$ to $R_{16}'$ may be bonded to form a ring; and n represents 0 or 1.

—Y group

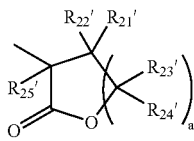 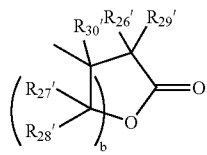

In —Y group, $R_{21}'$ to $R_{30}'$ each represents a hydrogen atom or an alkyl group; and a and b each represents 1 or 2.

In formulae (pI) to (pVI), the alkyl group represented by $R_{12}$ to $R_{25}$ is a straight chain or branched alkyl group having from 1 to 4 carbon atoms, e.g., a methyl group, an ethyl group, an n-propyl group, an isopropyl group, an n-butyl group, an isobutyl group, a sec-butyl group and a t-butyl group are exemplified.

As the examples of the substituents that the alkyl group may have, an alkoxyl group having from 1 to 4 carbon atoms, a halogen atom (a fluorine atom, a chlorine ion, a bromine ion, an iodine ion), an acyl group, an acyloxy group, a cyano group, a hydroxyl group, a carboxyl group, an alkoxycarbonyl group, and a nitro group can be exemplified.

The cycloalkyl groups represented by $R_{11}$ to $R_{25}$ or the cycloalkyl group formed by Z and carbon atoms may be monocyclic or polycyclic. Specifically, groups having a monocyclic, bicyclic, tricyclic or tetracyclic structure having 5 or more carbon atoms can be exemplified. The number of carbon atoms is preferably from 6 to 30, and particularly preferably from 7 to 25. These cycloalkyl groups may have a substituent.

As preferred cycloalkyl groups, an adamantyl group, a noradamantyl group, a decalin residue, a tricyclodecanyl group, a tetracyclododecanyl group, a norbornyl group, a cedrol group, a cyclohexyl group, a cycloheptyl group, a cyclooctyl group, a cyclodecanyl group, and a cyclododecanyl group can be exemplified. More preferred cycloalkyl groups are an adamantyl group, a decalin residue, a norbornyl group, a cedrol group, a cyclohexyl group, a cycloheptyl group, a cyclooctyl group, a cyclodecanyl group and a cyclododecanyl group.

As the substituents of these cycloalkyl groups, an alkyl group, a halogen atom, a hydroxyl group, an alkoxyl group, a carboxyl group and an alkoxycarbonyl group can be exemplified. As the alkyl group, lower alkyl groups, e.g., a methyl group, an ethyl group, a propyl group, an isopropyl group and a butyl group are preferred, and more preferably a methyl group, an ethyl group, a propyl group and an isopropyl group. As the alkoxyl group, alkoxyl groups having from 1 to 4 carbon atoms, e.g., a methoxy group, an ethoxy group, a propoxy group and a butoxy group can be exemplified. As the substituents that these alkyl group, alkoxyl group and alkoxycarbonyl group may further have, a hydroxyl group, a halogen atom and an alkoxyl group can be exemplified.

The structures represented by formulae (pI) to (pVI) in the resin can be used for the protection of alkali-soluble groups. As the alkali-soluble groups, various groups well known in this technical field can be exemplified.

Specifically, as the alkali-soluble groups, a carboxylic acid group, a sulfonic acid group, a phenol group and a thiol group are exemplified, preferably a carboxylic acid group and a sulfonic acid group.

As the alkali-soluble groups protected with the structures represented by the above formulae (pI) to (pVI) in the above resins, the structures wherein the hydrogen atom of the carboxyl group is substituted with the structures represented by formulae (pI) to (pVI) are preferably exemplified.

As the repeating unit having the alkali-soluble group protected with the structure represented by any of the above formulae (pI) to (pVI), a repeating unit represented by the following formula (pA) is preferred.

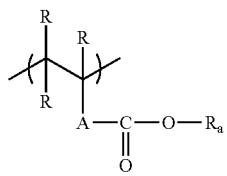

(pA)

In formula (pA), R represents a hydrogen atom, a halogen atom or a straight chain or branched alkyl group having from 1 to 4 carbon atoms, and a plurality of R's may be the same or different.

A represents a single group or the combination of two or more groups selected from the group consisting of a single bond, an alkylene group, an ether group, a thioether group, a carbonyl group, an ester group, an amido group, a sulfonamido group, a urethane group and a urea group.

Ra represents a group represented by any of formulae (pI) to (pVI).

The repeating unit represented by (pA) is most preferably a repeating unit by 2-alkyl-2-adamantyl(meth)acrylate and dialkyl(1-adamantyl)methyl(meth)acrylate.

The specific examples of the repeating units represented by formula (pA) are shown below.

(In the formulae, Rx represents H, $CH_3$ or $CF_3$.)

1

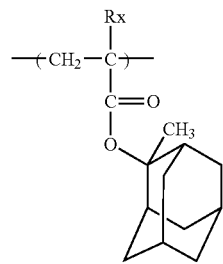

2

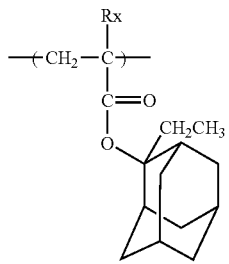

3

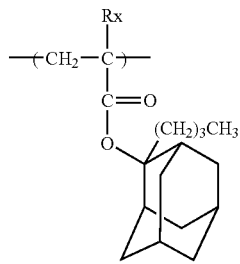

-continued

4

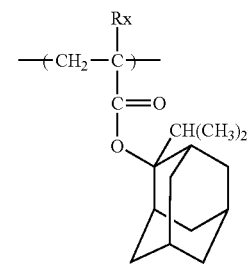

5

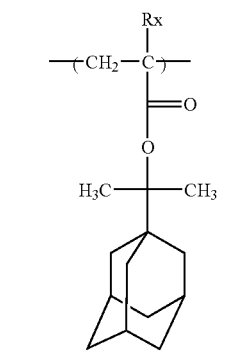

6

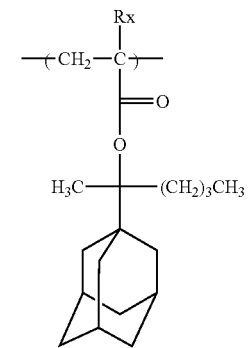

7

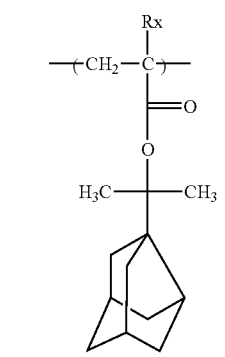

8

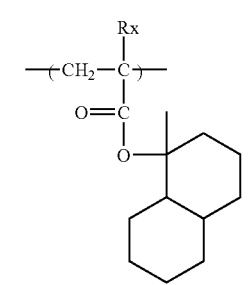

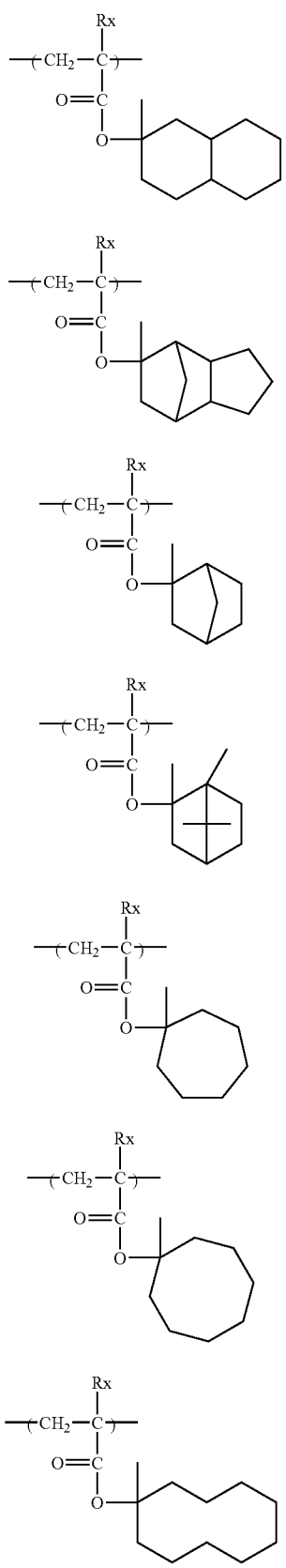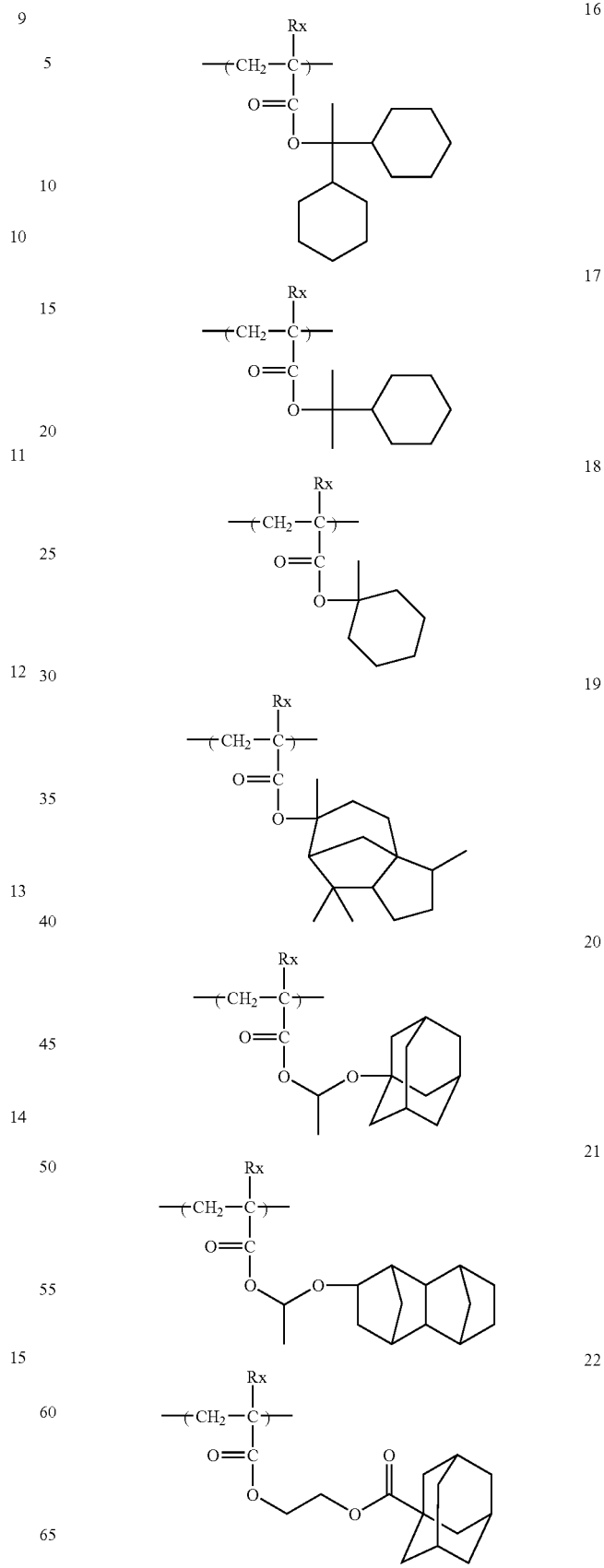

-continued

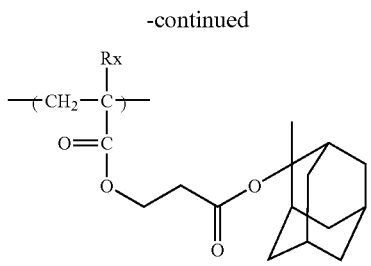

(23)

In formula (II-AB), $R_{11}'$ and $R_{12}'$ each represents a hydrogen atom, a cyano group, a halogen atom or an alkyl group.

Z' contains bonded two carbon atoms (C—C) and represents an atomic group to form an alicyclic structure.

As the halogen atoms represented by $R_{11}'$ and $R_{12}'$, a chlorine atom, a bromine atom, a fluorine atom and an iodine atom are exemplified.

As the alkyl groups represented by $R_{11}'$, $R_{12}'$ and $R_{21}'$ to $R_{30}'$, straight chain or branched alkyl groups having from 1 to 10 carbon atoms are preferred, straight chain or branched alkyl groups having from 1 to 6 carbon atoms are more preferred, and a methyl group, an ethyl group, a propyl group, an isopropyl group, an n-butyl group, an isobutyl group, a sec-butyl group and a t-butyl group are still more preferred.

As further substituents of the alkoxyl group, a hydroxyl group, a halogen atom, a carboxyl group, an alkoxyl group, an acyl group, a cyano group and an acyloxy group can be exemplified. As the halogen atom, a chlorine atom, a bromine atom, a fluorine atom, an iodine atom can be exemplified, as the alkoxyl group, an alkoxyl group having from 1 to 4 carbon atoms, e.g., a methoxy group, an ethoxy group, a propoxy group and a butoxy group can be exemplified, as the acyl group, e.g., a formyl group and an acetyl group can be exemplified, and as the acyloxy group, an acetoxy group can be exemplified.

The atomic group represented by Z' to form an alicyclic structure is an atomic group for forming a repeating unit of alicyclic hydrocarbon, which may have a substituent, in a resin, and an atomic group to form a crosslinking alicyclic structure to form a repeating unit having crosslinking alicyclic hydrocarbon is preferred above all.

As the skeleton of alicyclic hydrocarbon formed, the same alicyclic hydrocarbon groups as represented by $R_{11}$ to $R_{25}$ in formulae (pI) to (pVI) are exemplified.

The skeleton of the alicyclic hydrocarbon may have a substituent, and as the substituents, the groups represented by $R_{13}'$ to $R_{16}'$ in formula (II-A) or (II-B) can be exemplified.

Of the repeating units having crosslinking alicyclic hydrocarbon, the repeating units represented by formula (II-A) or (II-B) are more preferred.

In the alicyclic hydrocarbon-based acid-decomposable resin in the invention, the acid-decomposable group may be contained in —C(=O)—X-A'-$R_{17}'$, or may be contained as the substituent of Z' in formula (II-AB).

The structure of the acid-decomposable group is represented by formula —C(=O)—$X_1$—$R_0$.

In the formula, $R_0$ represents a tertiary alkyl group, e.g., a t-butyl group or a t-amyl group, an isoboronyl group, a 1-alkoxyethyl group, e.g., a 1-ethoxyethyl group, a 1-butoxyethyl group, a 1-isobutoxyethyl group, or a 1-cyclohexyloxyethyl group, an alkoxymethyl group, e.g., a 1-methoxymethyl group or a 1-ethoxymethyl group, a 3-oxoalkyl group, a tetrahydropyranyl group, a tetrahydrofuranyl group, a trialkyl-silyl ester group, a 3-oxocyclohexyl ester group, a 2-methyl-2-adamantyl group, or a mevalonic lactone residue. $X_1$ has the same meaning as X above.

As the halogen atoms represented by $R_{13}'$, $R_{14}'$, $R_{15}'$ and $R_{16}'$ in formulae (II-A) and (II-B), a chlorine atom, a bromine atom, a fluorine atom and an iodine atom can be exemplified.

The alkyl groups represented by $R_5$, $R_6$, $R_{13}'$ to $R_{16}'$, $R_{21}'$ to $R_{30}'$ are preferably straight chain or branched alkyl groups having from 1 to 10 carbon atoms, more preferably straight chain or branched alkyl groups having from 1 to 6 carbon atoms, and still more preferably a methyl group, an ethyl group, a propyl group, an isopropyl group, an n-butyl group, an isobutyl group, a sec-butyl group and t-butyl.

The cycloalkyl groups represented by $R_5$, $R_6$, $R_{13}'$ to $R_{16}'$ are, e.g., monocyclic cycloalkyl groups and crosslinked hydrocarbons, and, e.g., a cyclopropyl group, a cyclopentyl group, a cyclohexyl group, an adamantyl group, a 2-methyl-2-adamantyl group, a norbornyl group, a boronyl group, an isoboronyl group, a tricyclodecanyl group, a dicyclopentenyl group, a norbornanepoxy group, a menthyl group, an isomenthyl group, a neomenthyl group, and a tetracyclododecanyl group can be exemplified.

As the rings formed by the bonding of at least two of $R_{13}'$ and $R_{16}'$, rings having from 5 to 12 carbon atoms, e.g., cyclopentene, cyclohexene, cycloheptane and cyclooctane can be exemplified.

As the alkoxyl group represented by $R_{17}'$, an alkoxyl group having from 1 to 4 carbon atoms, e.g., a methoxy group, an ethoxy group, a propoxy group or a butoxy group can be exemplified.

As further substituents of the alkyl, cycloalkyl and alkoxyl groups, a hydroxyl group, a halogen atom, a carboxyl group, an alkoxyl group, an acyl group, a cyano group, an acyloxy group, an alkyl group, and a cycloalkyl group can be exemplified. As the halogen atom, a chlorine atom, a bromine atom, a fluorine atom and an iodine atom can be exemplified, as the alkoxyl group, an alkoxyl group having from 1 to 4 carbon atoms, e.g., a methoxy group, an ethoxy group, a propoxy group and a butoxy group can be exemplified, as the acyl group, e.g., a formyl group and an acetyl group can be exemplified, and as the acyloxy group, an acetoxy group can be exemplified.

The alkyl groups and cyclic hydrocarbon groups are the same as those described above.

As the divalent linking group represented by A', a single group or combinations comprising two or more groups selected from the group consisting of an alkylene group, an ether group, a thioether group, a carbonyl group, an ester group, an amido group, a sulfonamido group, a urethane group and a urea group.

In the alicyclic hydrocarbon-based acid-decomposable resin in the invention, a group capable of decomposing by the action of an acid can be contained in at least one repeating unit of a repeating unit having a partial structure containing alicyclic hydrocarbon represented by formula (pI), (pII), (pIII) or (pIV), a repeating unit represented by formula (II-AB), and a repeating unit of the later-described copolymer component.

Various substituents of $R_{13}'$ to $R_{16}'$ in formula (II-A) or (II-B) can also be used as the substituents of the atomic group to form an alicyclic structure in formula (II-AB), or atomic group Z to form a crosslinking alicyclic structure.

The specific examples of the repeating units represented by formula (II-A) or (II-B) are shown below, but the invention is not limited thereto.

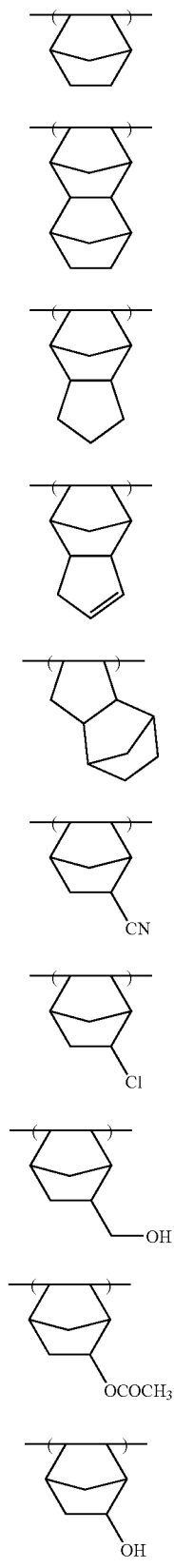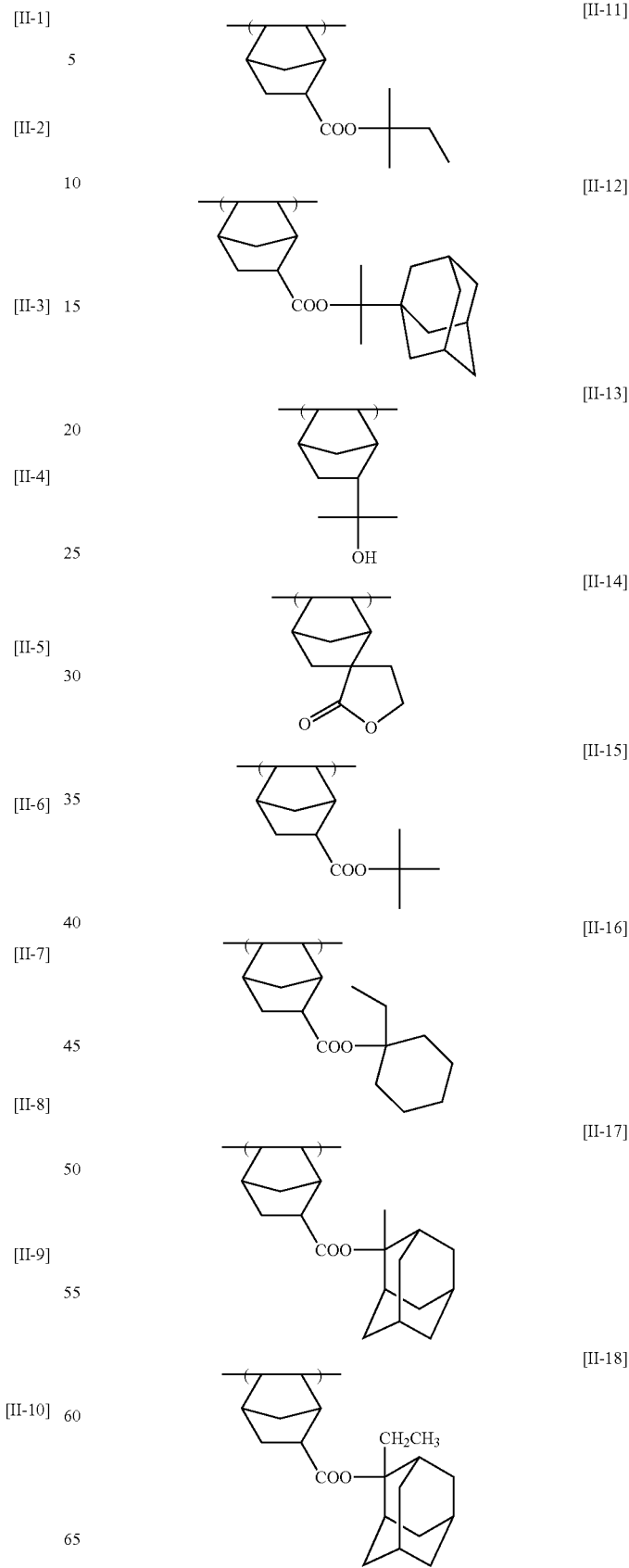

[II-19] 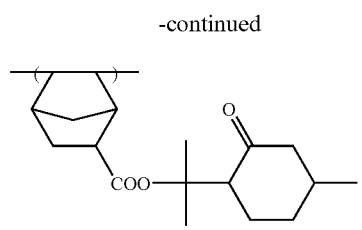
[II-20] 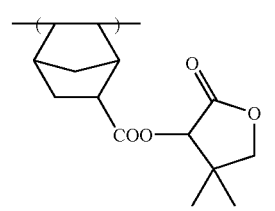
[II-21] 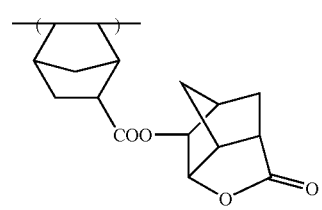
[II-22] 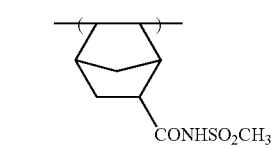
[II-23] 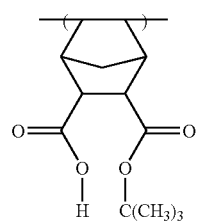
[II-24] 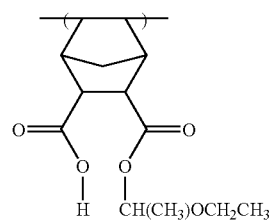
[II-25] 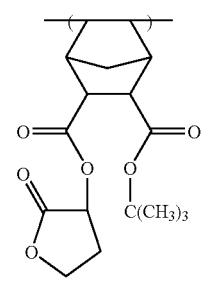
[II-26] 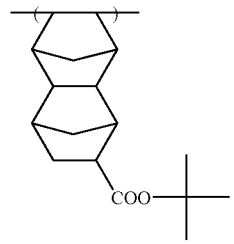
[II-27] 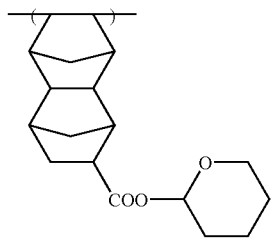
[II-28] 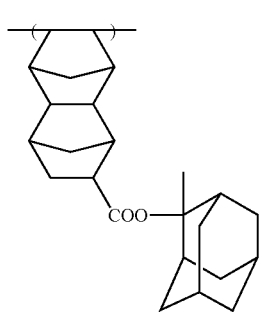
[II-29] 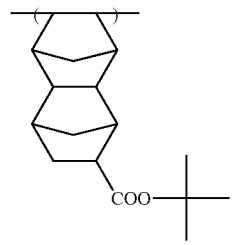
[II-30] 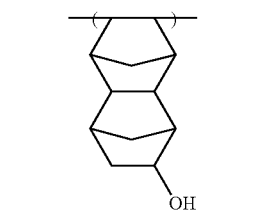
[II-31] 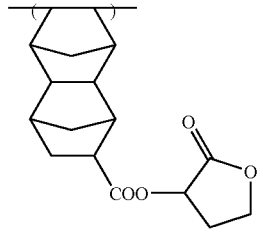

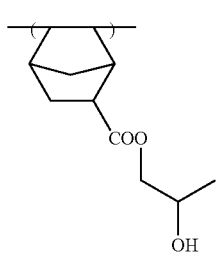
[II-32]

The alicyclic hydrocarbon-based acid-decomposable resin in the invention preferably has a lactone group, more preferably has a repeating unit having a group having a lactone structure represented by the following formula (Lc) or any of formulae (V-1) to (V-5). Further, a group having a lactone structure may be directly bonded to the main chain.

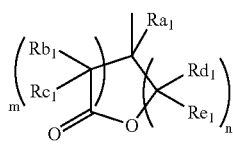
(Lc)

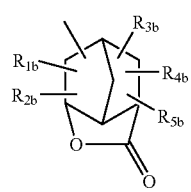
(V-1)

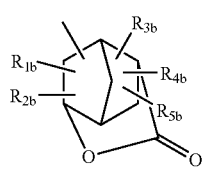
(V-2)

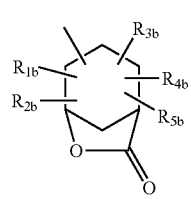
(V-3)

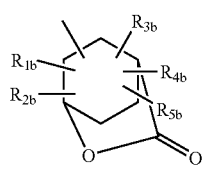
(V-4)

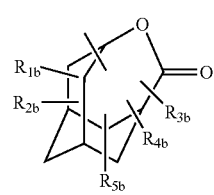
(V-5)

In formula (Lc), $Ra_1$, $Rb_1$, $Rc_1$, $Rd_1$, and $Re_1$, each represents a hydrogen atom or an alkyl group; m and n each represents an integer of from 0 to 3, and m+n is from 2 to 6.

In formulae (V-1) to (V-5), $R_{1b}$, $R_{2b}$, $R_{3b}$, $R_{4b}$ and $R_{5b}$ each represents a hydrogen atom, an alkyl group, a cycloalkyl group, an alkoxyl group, an alkoxycarbonyl group, an alkylsulfonyl-imino group or an alkenyl group. Two of $R_{1b}$ to $R_{5b}$ may be bonded to form a ring.

As the alkyl groups represented by $Ra_1$ to $Re_1$, in formula (Lc), and the alkyl groups in the alkyl groups, alkoxyl groups, alkoxycarbonyl groups and alkylsulfonylimino groups represented by $R_{1b}$ to $R_{5b}$ in formulae (V-1) to (V-5), straight chain or branched alkyl groups are exemplified, and these alkyl groups may have a substituent. As the preferred substituents, a hydroxyl group, a halogen atom, a carboxyl group, an alkoxyl group, an acyl group, a cyano group, an acyloxy group and a cycloalkyl group can be exemplified.

As the repeating units having a group having a lactone structure represented by formula (Lc) or any of formulae (V-1) to (V-5), a repeating unit in which at least one of $R_{13}{'}$ to $R_{16}{'}$ in formula (II-A) or (II-B) has a group represented by formula (Lc) or any of formulae (V-1) to (V-5) (for example, $R_5$ in $COOR_5$ represents a group represented by formula (Lc) or any of formulae (V-1) to (V-5)), or a repeating unit represented by the following formula (AI) can be exemplified.

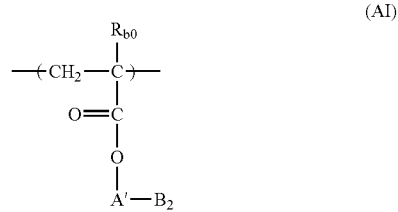
(AI)

In formula (AI), $R_{b0}$ represents a hydrogen atom, a halogen atom, or an alkyl group having from 1 to 4 carbon atoms. As the preferred substituents that the alkyl group represented by $R_{b0}$ may have, those described above as the preferred substituents that the alkyl group represented by $R_{1b}$ in formulae (V-1) to (V-5) may have can be exemplified.

As the halogen atom represented by $R_{b0}$, a fluorine atom, a chlorine atom, a bromine atom and an iodine atom can be exemplified. $R_{b0}$ preferably represents a hydrogen atom.

$A_b$ represents a single bond, an ether group, an ester group, a carbonyl group, an alkylene group, or a divalent linking group combining these groups.

V represents a group represented by formula (Lc) or any of formulae (V-1) to (V-5).

The specific examples of repeating units having a group having a lactone structure are shown below, but the invention is not limited thereto.

(In the formulae, Rx represents H, $CH_3$ or $CF_3$.)

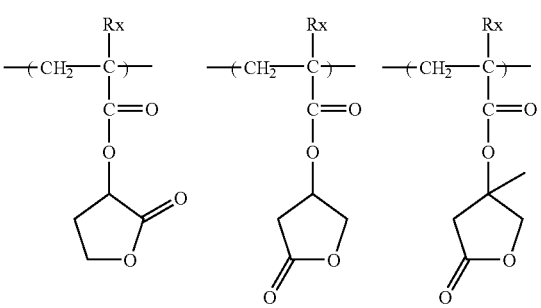

-continued
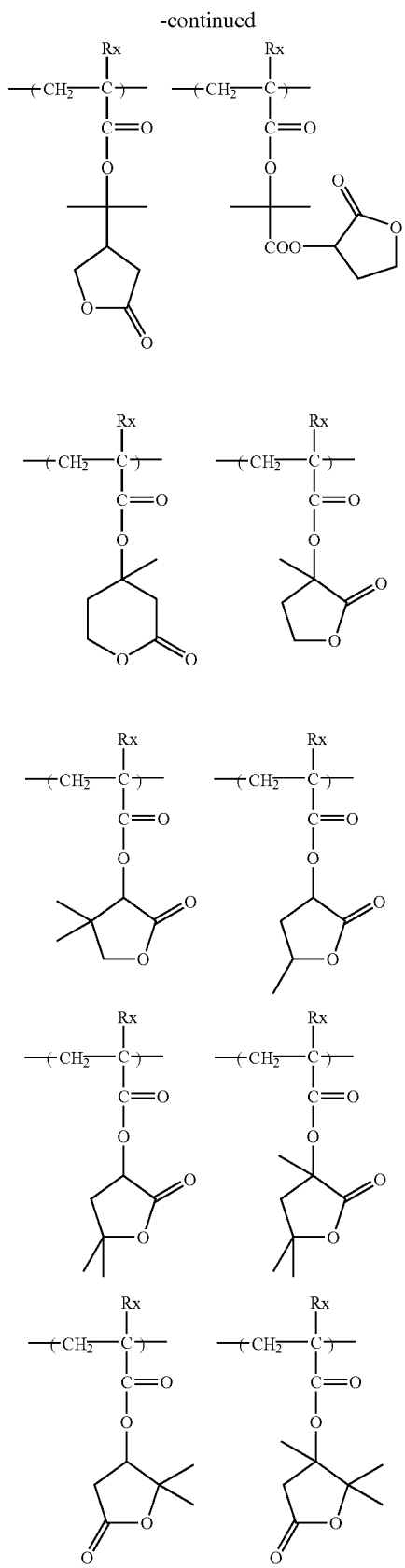
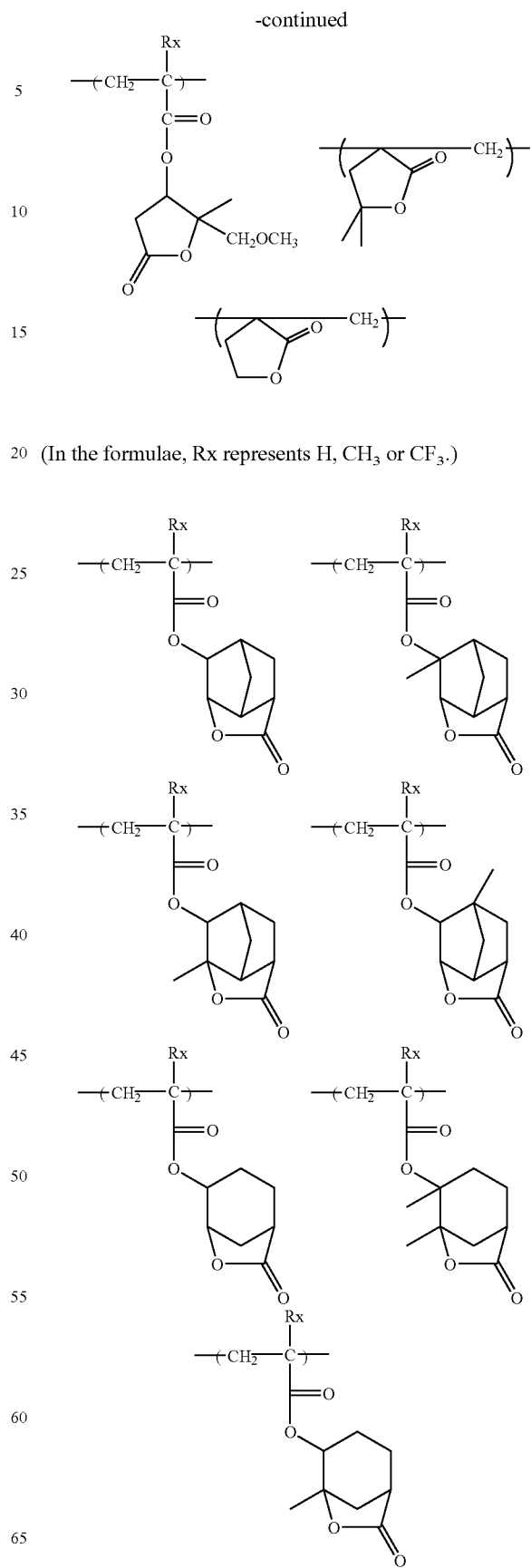
(In the formulae, Rx represents H, CH$_3$ or CF$_3$.)

-continued
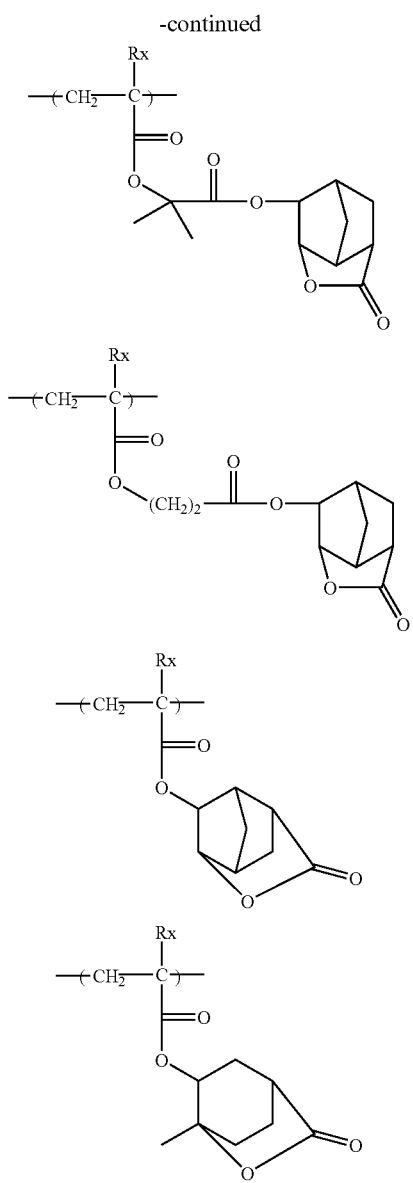
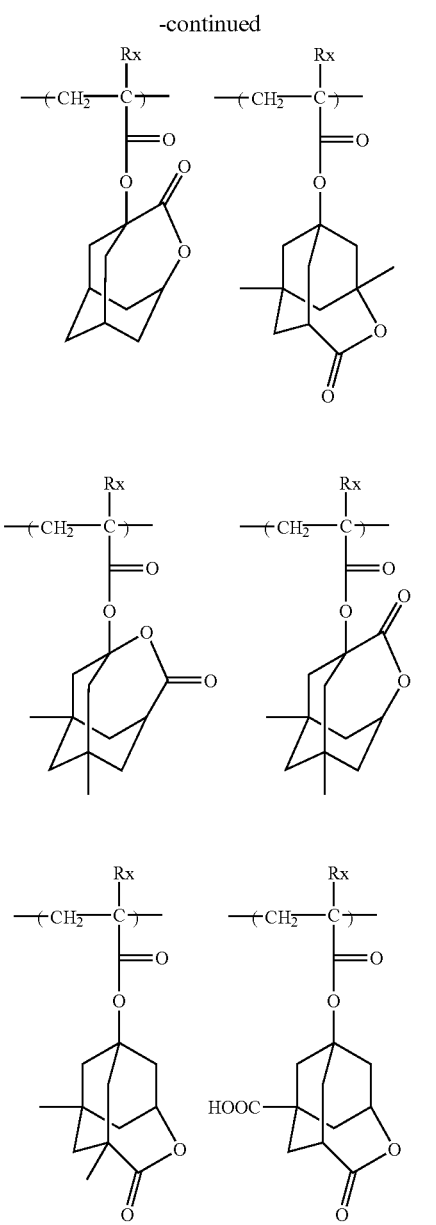
(In the formulae, Rx represents H, CH₃ or CF₃.)

-continued

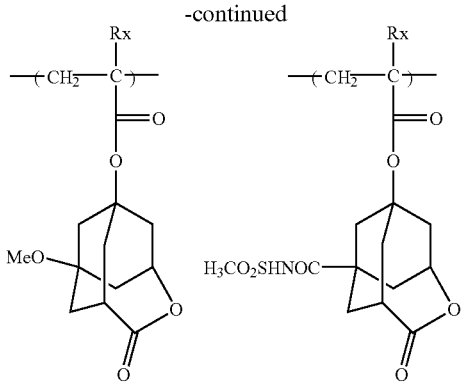

The alicyclic hydrocarbon-based acid-decomposable resin in the invention may contain a repeating unit having an adamantane skeleton having a group represented by the following formula (VII).

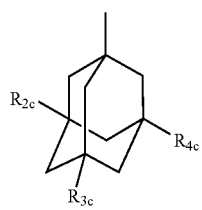
(VII)

In formula (VII), $R_{2c}$, $R_{3c}$ and $R_{4c}$ each represents a hydrogen atom or a hydroxyl group, provided that at least one of $R_{2c}$, $R_{3c}$ and $R_{4c}$ represents a hydroxyl group.

The group represented by formula (VII) is preferably a dihydroxy body or a monohydroxy body, more preferably a dihydroxy body.

As the repeating unit having a group represented by formula (VII), a repeating unit in which at least one of $R_{13}'$ to $R_{16}'$ in formula (II-A) or (II-B) has a group represented by formula (VII) (for example, $R_5$ in —COOR$_5$ represents a group represented by formula (VII)), or a repeating unit represented by the following formula (AII) can be exemplified.

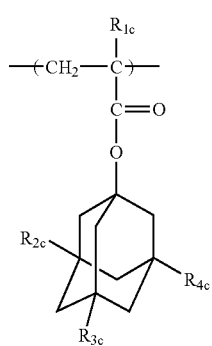
(AII)

In formula (AII), $R_{1c}$ represents a hydrogen atom or a methyl group.

$R_{2c}$, $R_{3c}$ and $R_{4c}$ each represents a hydrogen atom or a hydroxyl group, provided that at least one of $R_{2c}$, $R_{3c}$ and $R_{4c}$ represents a hydroxyl group. It is preferred that two of $R_{2c}$, $R_{3c}$ and $R_{4c}$ represent a hydroxyl group.

The specific examples of the repeating units having a structure represented by formula (AII) are shown below, but the invention is not limited thereto.

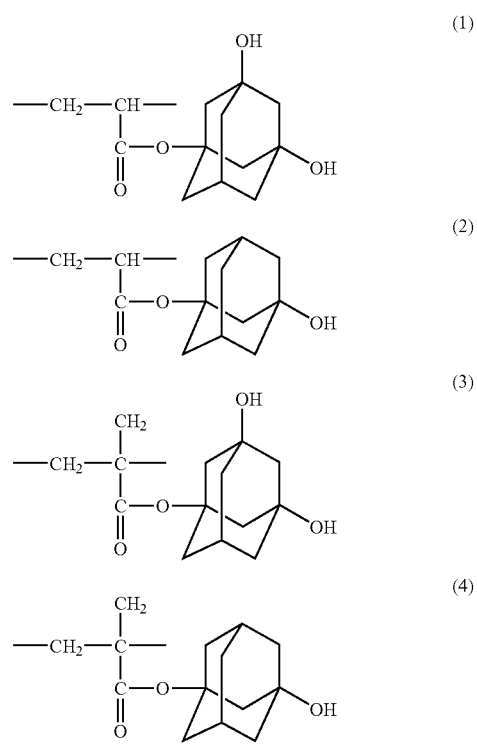

The alicyclic hydrocarbon-based acid-decomposable resin in the invention may contain a repeating unit represented by the following formula (VIII).

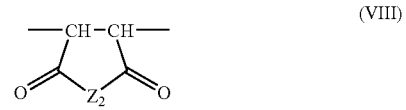
(VIII)

In formula (VIII), $Z_2$ represents —O— or —N(R$_{41}$)—; $R_{41}$ represents a hydrogen atom, a hydroxyl group, an alkyl group or —OSO$_2$—R$_{42}$; and R$_{42}$ represents an alkyl group, a cycloalkyl group, or a camphor residue. The alkyl group represented by R$_{41}$ and R$_{42}$ may be substituted with a halogen atom (preferably a fluorine atom), etc.

The specific examples of the repeating units represented by formula (VIII) are shown below, but the invention is not limited thereto.

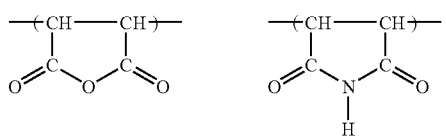

-continued

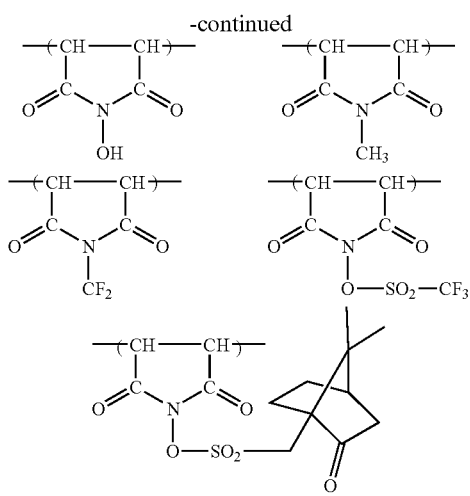

It is preferred for the alicyclic hydrocarbon-based acid-decomposable resin in the invention to have a repeating unit having an alkali-soluble group, and more preferred to have a repeating unit having a carboxyl group. By containing this repeating unit, the resolution in contact hole use increases. A repeating unit in which a carboxyl group is directly bonded to the main chain of a resin, such as a repeating unit by an acrylic acid or a methacrylic acid, and a repeating unit in which a carboxyl group is bonded to the main chain of a resin via a linking group are preferred as repeating units having a carboxyl group, and the linking group may have either a monocyclic or polycyclic hydrocarbon structure. A repeating unit by acrylic acid or methacrylic acid is most preferred.

The alicyclic hydrocarbon-based acid-decomposable resin in the invention may have various repeating structural units besides the above repeating units for the purpose of adjusting dry etching resistance, an aptitude for standard developers, adhesion to substrates, resist profile, and in addition to these, general requisite characteristics of resists, e.g., resolution, heat resistance and sensitivity.

As these repeating structural units, the repeating structural units corresponding to monomers shown below can be exemplified, but the invention is not limited thereto.

By containing various kinds of repeating structural units, fine adjustment of performances required of the alicyclic hydrocarbon-based acid-decomposable resins, in particular fine adjustment of the following performances becomes possible, that is,
(1) Solubility in a coating solvent,
(2) A film-forming property (a glass transition point),
(3) Alkali developability,
(4) Decrease of layer thickness (hydrophobic-hydrophilic property, selection of an alkali-soluble group),
(5) Adhesion of an unexposed area to a substrate, and
(6) Dry etching resistance.

The examples of such monomers include compounds having one addition polymerizable unsaturated bond selected from acrylic esters, methacrylic esters, acrylamides, methacrylamides, allyl compounds, vinyl ethers and vinyl esters.

In addition to the aforementioned compounds, addition polymerizable unsaturated compounds copolymerizable with the monomers corresponding to the above various repeating structural units may be used for copolymerization.

In the alicyclic hydrocarbon-based acid-decomposable resins, the molar ratio of the content of each repeating structural unit is arbitrarily selected to adjust dry etching resistance, an aptitude for a standard developer, adhesion to a substrate, and resist profile, in addition to these, to adjust general requisite characteristics of resists, e.g., resolution, heat resistance and sensitivity.

The preferred embodiments of the alicyclic hydrocarbon-based acid-decomposable resins in the invention include the following.
(1) Resins containing a repeating unit having a partial structure containing the alicyclic hydrocarbon represented by any of formulae (pI) to (pVI) (a side chain type).
(2) Resins containing a repeating unit represented by formula (II-AB) (a main chain type), and the following embodiment is further exemplified in (2).
(3) Resins containing a repeating unit represented by formula (II-AB), a maleic anhydride derivative and a (meth)acrylate structure (a hybrid type).

In the alicyclic hydrocarbon-based acid-decomposable resins, the content of a repeating unit having an acid decomposable group is preferably from 10 to 60 mol % in all the repeating structural units, more preferably from 20 to 50 mol %, and still more preferably from 25 to 40 mol %.

In the present invention, at least one methacrylic acid ester repeating unit and at least one acrylic acid ester repeating unit are preferably contained as the repeating unit having an acid-decomposable group. The molar ratio of the acrylic acid ester to the methacrylic acid ester is generally from 10/90 to 90/10, preferably from 20/80 to 80/20, more preferably from 30/70 to 70/30, and most preferably from 40/60 to 60/40.

In the alicyclic hydrocarbon-based acid-decomposable resins, the content of a repeating unit having a partial structure containing alicyclic hydrocarbon represented by any of formulae (pI) to (pVI) is preferably from 30 to 70 mol % in all the repeating structural units, more preferably from 35 to 65 mol %, and still more preferably from 40 to 60 mol %.

In the alicyclic hydrocarbon-based acid-decomposable resins, the content of a repeating unit represented by formula (II-AB) is preferably from 10 to 60 mol % in all the repeating structural units, more preferably from 15 to 55 mol %, and still more preferably from 20 to 50 mol %.

The content of repeating structural units on the basis of the monomers of the further copolymer components in the resin can also be optionally set according to the desired resist performances, and the content is generally preferably 99 mol % or less based on the total mol number of a repeating structural unit having a partial structure containing alicyclic hydrocarbon represented by any of formulae (pI) to (pVI) and a repeating unit represented by formula (II-AB), more preferably 90 mol % or less, and still more preferably 80 mol % or less.

When the photosensitive composition according to the invention is a composition for ArF exposure, it is preferred that the resin should not contain an aromatic group from the point of the transparency to ArF light.

The alicyclic hydrocarbon-based acid-decomposable resins for use in the invention can be synthesized according to ordinary methods (e.g., radical polymerization). For example, as ordinary methods, a monomer seed is put in a reaction vessel at a time or in parts during the course of the reaction, and according to necessity the monomer is dissolved in a reaction solvent such as ethers, e.g., tetrahydrofuran, 1,4-dioxane or diisopropyl ether, ketones, e.g., methyl ethyl ketone or methyl isobutyl ketone, an ester solvent, e.g., ethyl acetate, or the later-described solvents capable of dissolving the composition of the invention, e.g., propyelne glycol monomethyl ether acetate, to make the monomer homogeneous. The solution is then heated, if necessary, under the inert gas atmosphere such as nitrogen or argon, and polymerization is initiated with commercially available radical polymerization initiator (e.g., azo initiators, peroxide and the like). If necessary, the initiator is further added at a time or in parts, and after completion of the reaction, the reaction product is put in a solvent, and the desired polymer is recovered as powder or solid. The reaction concentration is 20 mass % or more, preferably 30 mass % or more, and more preferably 40 mass % or more. The reaction temperature is from 10 to 150° C., preferably from 30 to 120° C., and more preferably from 50 to 100° C.

When the photosensitive composition according to the invention is used in the upper layer resist of a multilayer resist, it is preferred that the resin of component (B) should have a silicon atom.

As resins having a silicon atom and capable of decomposing by the action of an acid to thereby increase the solubility in an alkali developer, resins having a silicon atom at least on one side of the main chain and the side chain can be used. As resins having a siloxane structure on the side chain of resins, the copolymer of, e.g., an olefin monomer having a silicon atom on the side chain, and a (meth)acrylic acid monomer having maleic anhydride and an acid decomposable group on the side chain.

As resins having a silicon atom, resins having a trialkylsilyl structure and a monocyclic or polycyclic siloxane structure are preferred, resins having repeating units having the structures represented by the following formulae (SS-1) to (SS-4) are more preferred, and (meth)acrylic ester series repeating units having the structures represented by formulae (SS-1) to (SS-4), vinyl series repeating units and allyl series repeating units are still more preferred.

In formulae (SS-1) to (SS-4), Rs represents an alkyl group having from 1 to 5 carbon atoms, preferably a methyl group or an ethyl group.

It is preferred that resins having silicon atoms have two or more kinds of different repeating units having silicon atoms, resins having both (Sa) repeating unit having from 1 to 4 silicon atoms and (Sb) repeating unit having from 5 to 10 silicon atoms are more preferred, and resins having at least one repeating unit having a structure represented by any of formulae (SS-1) to (SS-3) and a repeating unit having a structure represented by formula (SS-4) are still more preferred.

When the positive photosensitive composition of the invention is irradiated with $F_2$ excimer laser rays, the resin of component (B) is preferably a resin having a structure wherein fluorine atoms are substituted on the main chain and/or the side chain of the polymer skeleton and capable of decomposing by the action of an acid to thereby increase the solubility in an alkali developer (hereinafter also referred to as "a fluorine group-containing resin), the resin is more preferably a resin containing a hydroxyl group the 1-position of which is substituted with a fluorine atom or a fluoroalkyl group, or containing a hydroxyl group the 1-position of which is substituted with a fluorine atom or a fluoroalkyl group that is protected with an acid-decomposable group. The most preferred resin is a resin having a hexafluoro-2-propanol structure, or a resin having a structure that the hydroxyl group of hexafluoro-2-propanol is protected with an acid-decomposable group. By the incorporation of fluorine atoms, the transparency to the far ultraviolet rays, in particular to $F_2$ ray (157 nm) can be improved.

As the fluorine group-containing resins in acid-decomposable resin (B), resins containing at least one repeating unit represented by any of the following formulae (FA) to (FG) are preferably exemplified.

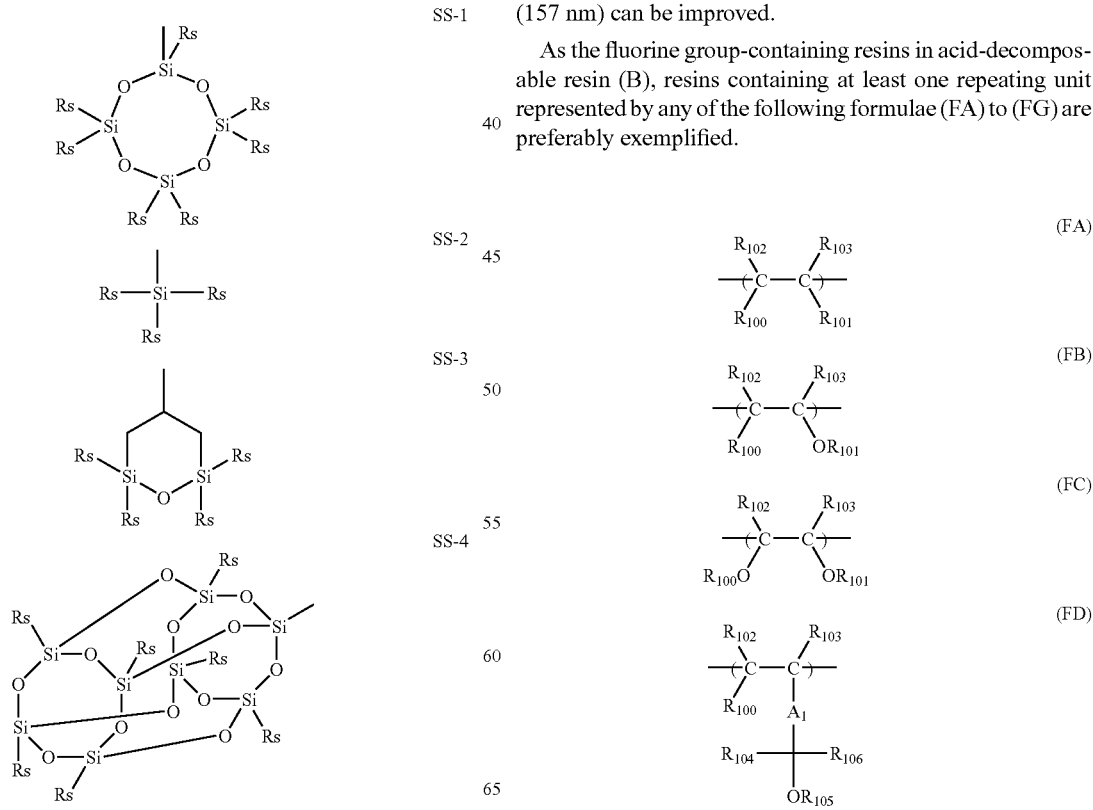

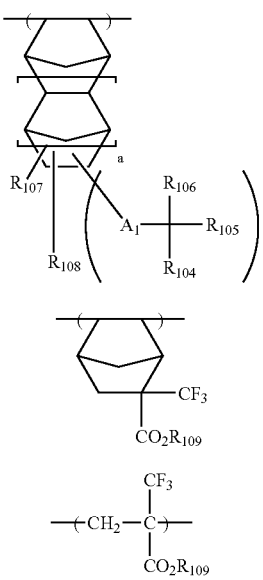

(FE)

(FF)

(FG)

In the above formulae, $R_{100}$, $R_{101}$, $R_{102}$ and $R_{103}$ each represents a hydrogen atom, a fluorine atom, an alkyl group or an aryl group.

$R_{104}$ and $R_{106}$ each represents a hydrogen atom, a fluorine atom or an alkyl group, and at least one of $R_{104}$ and $R_{106}$ represents a fluorine atom or a fluoroalkyl group. Preferably both $R_{104}$ and $R_{106}$ represent a trifluoromethyl group.

$R_{105}$ represents a hydrogen atom, an alkyl group, a cycloalkyl group, an acyl group, an alkoxycarbonyl group, or a group decomposable by the action of an acid.

$A_1$ represents a single bond, a divalent linking group, e.g., a straight chain or branch alkylene group, a cycloalkylene group, an alkenylene group, an arylene group, —OCO—, —COO—, —CON($R_{24}$)—, or a linking group containing a plurality of these groups. $R_{24}$ represents a hydrogen atom or an alkyl group.

$R_{107}$ and $R_{108}$ each represents a hydrogen atom, a halogen atom, an alkyl group, an alkoxyl group, an alkoxycarbonyl group, or a group decomposable by the action of an acid.

$R_{109}$ represents a hydrogen atom, an alkyl group, a cycloalkyl group, or a group decomposable by the action of an acid.

a represents 0 or 1.

b represents 0, 1 or 2.

Further, $R_{100}$ and $R_{101}$ in formulae (FA) and (FC) may form a ring through an alkylene group (having from 1 to 5 carbon atoms) which may be substituted with a fluorine atom.

The repeating units represented by formulae (FA) to (FG) contain at least 1, preferably 3 or more, fluorine atoms per one repeating unit.

In formulae (FA) to (FG), the alkyl group is an alkyl group having from 1 to 8 carbon atoms, specifically, a methyl group, an ethyl group, a propyl group, an n-butyl group, a sec-butyl group, a hexyl group, a 2-ethylhexyl group, and an octyl group are preferably exemplified.

The cycloalkyl group may be monocyclic or polycyclic. As the monocyclic groups, preferably those having from 3 to 8 carbon atoms, e.g., a cyclopropyl group, a cyclopentyl group, a cyclohexyl group, a cycloheptyl group and a cyclooctyl group can be exemplified. As the polycyclic groups, preferably those having from 6 to 20 carbon atoms, e.g., an ada- mantyl group, a norbornyl group, an isoboronyl group, a camphanyl group, a dicyclopentyl group, an α-pinel group, a tricyclodecanyl group, a tetracyclododecyl group and an androstanyl group can be exemplified. However, the carbon atoms in the monocyclic or polycyclic cycloalkyl groups may be substituted with hetero atoms such as an oxygen atom, etc.

The fluoroalkyl group is preferably, e.g., a fluoroalkyl group having from 1 to 12 carbon atoms, specifically a trifluoromethyl group, a perfluoroethyl group, a perfluoro-propyl group, a perfluorobutyl group, a perfluorohexyl group, a perfluorooctyl group, a perfluorooctylethyl group, and a perfluorododecyl group can be preferably exemplified.

As the aryl group, an aryl group having from 6 to 15 carbon atoms, specifically a phenyl group, a tolyl group, a dimethylphenyl group, a 2,4,6-trimethylphenyl group, a naphthyl group, an anthryl group and a 9,10-dimethoxyanthryl group can be preferably exemplified.

As the alkoxyl group, e.g., an alkoxyl group having from 1 to 8 carbon atoms, specifically a methoxy group, an ethoxy group, an n-propoxy group, an isopropoxy group, a butoxy group, a pentoxy group, an allyloxy group and an octoxy group can be preferably exemplified.

As the acyl group, e.g., an acyl group having from 1 to 10 carbon atoms, specifically a formyl group, an acetyl group, a propanoyl group, a butanoyl group, a pivaloyl group, an octanoyl group and a benzoyl group can be preferably exemplified.

As the alkoxycarbonyl group, an i-propoxycarbonyl group, a t-butoxycarbonyl group, a t-amyloxycarbonyl group and a 1-methyl-1-cyclohexyloxycarbonyl group, preferably a secondary, and more preferably a tertiary, alkoxycarbonyl group can be exemplified.

As the halogen atom, e.g., a fluorine atom, a chlorine atom, a bromine atom and an iodine atom can be exemplified.

As the alkylene group, preferably an alkylene group having from 1 to 8 carbon atoms, e.g., a methylene group, an ethylene group, a propylene group, a butylene group, a hexylene group and an octylene group can be exemplified.

As the alkenylene group, preferably an alkenylene group having from 2 to 6 carbon atoms, e.g., an ethenylene group, a propenylene group and a butenylene group can be exemplified.

As the cycloalkylene group, preferably a cycloalkylene group having from 5 to 8 carbon atoms, e.g., a cyclopentylene group and a cyclohexylene group can be exemplified.

As the arylene group, an arylene group having from 6 to 15 carbon atoms, e.g., a phenylene group, a tolylene group and a naphthylene group can be exemplified.

These groups may have a substituent, and the examples of the substituents include groups having active hydrogen, e.g., an alkyl group, a cycloalkyl group, an aryl group, an amino group, an amido group, a ureido group, a urethane group, a hydroxyl group and a carboxyl group, a halogen atom (e.g., a fluorine atom, a chlorine atom, a bromine atom and an iodine atom), an alkoxyl group (e.g., a methoxy group, an ethoxy group, a propoxy group, a butoxy group), a thioether group, an acyl group (e.g., an acetyl group, a propanoyl group, a benzoyl group), an acyloxy group (e.g., an acetoxy group, a propanoyloxy group, a benzoyloxy group), an alkoxycarbonyl group (e.g., a methoxycarbonyl group, an ethoxycarbonyl group, a propoxycarbonyl group), a cyano group, and a nitro group can be exemplified.

Here, as the alkyl, cycloalkyl and aryl groups, those described above are exemplified, but the alkyl group may further be substituted with a fluorine atom or a cycloalkyl group.

As the groups contained in the fluorine group-containing resins in the invention and capable of decomposing by the action of an acid to thereby increase the solubility in an alkali developer, —O—C($R_{36}$)($R_{37}$)($R_{38}$), —O—C($R_{36}$)($R_{37}$)(O$R_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($R_{38}$), and —COO—C($R_{36}$)($R_{37}$)(O$R_{39}$) can be exemplified.

$R_{36}$, $R_{37}$, $R_{38}$ and $R_{39}$ each represents an alkyl group, a cycloalkyl group, an aryl group, an aralkyl group or an alkenyl group; $R_{01}$ and $R_{02}$ each represents a hydrogen atom, an alkyl group, a cycloalkyl group, an alkenyl group (e.g., a vinyl group, an allyl group, a butenyl group, a cyclohexenyl group), an aralkyl group (e.g., a benzyl group, a phenethyl group, a naphthylmethyl group), or an aryl group.

The preferred specific examples of the groups include the ether groups or the ester groups of tertiary alkyl groups such as a t-butyl group, a t-amyl group, a 1-alkyl-1-cyclohexyl group, a 2-alkyl-2-adamantyl group, a 2-adamantyl-2-propyl group, and a 2-(4-methylcyclohexyl)-2-propyl group, acetal groups or acetal ester groups such as a 1-alkoxy-1-ethoxy group and a tetrahydropyranyl group, a t-alkylcarbonate group and a t-alkylcarbonylmethoxy group.

The specific examples of the repeating units represented by formulae (FA) to (FG) are shown below, but the invention is not limited thereto.

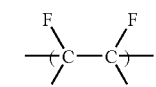  (F-1)

  (F-2)

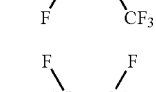  (F-3)

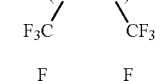  (F-4)

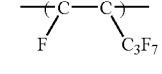  (F-5)

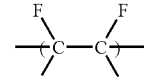  (F-6)

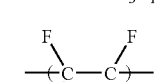  (F-7)

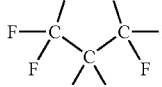  (F-8)

-continued

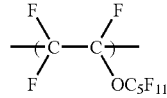  (F-9)

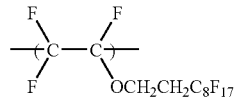  (F-10)

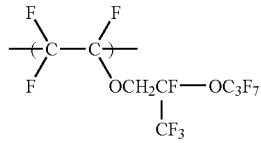  (F-11)

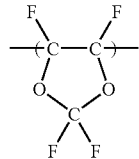  (F-12)

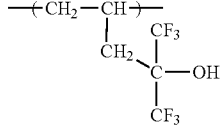  (F-13)

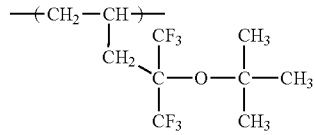  (F-14)

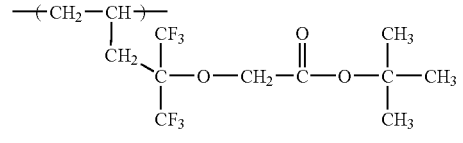  (F-15)

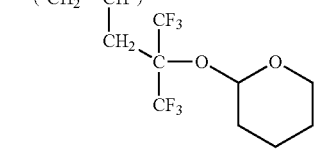  (F-16)

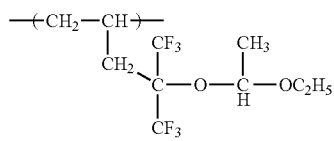  (F-17)

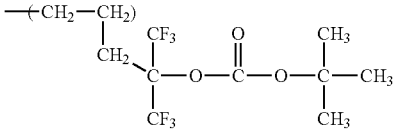  (F-18)

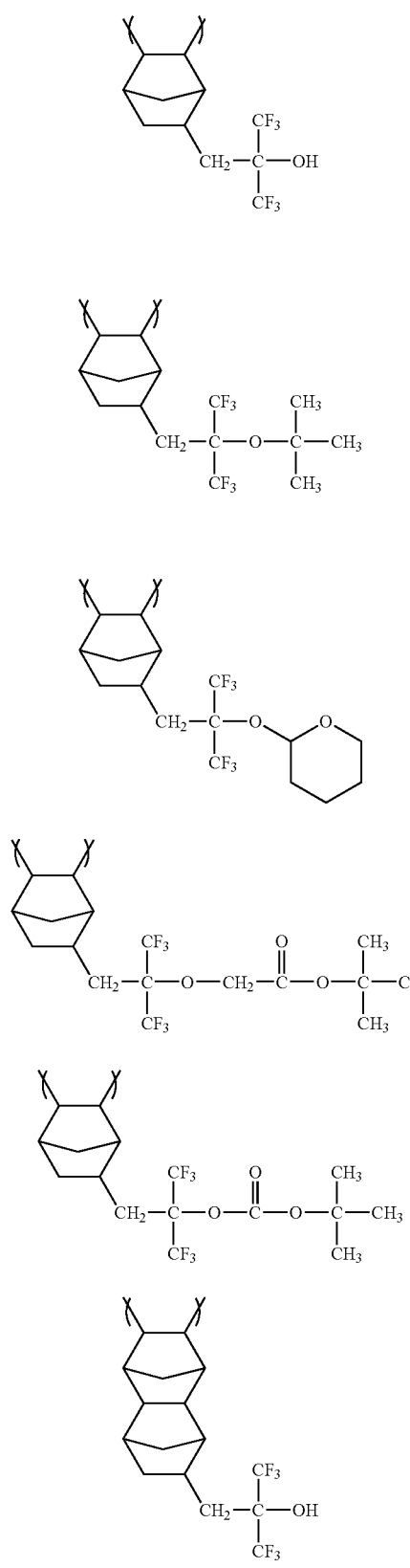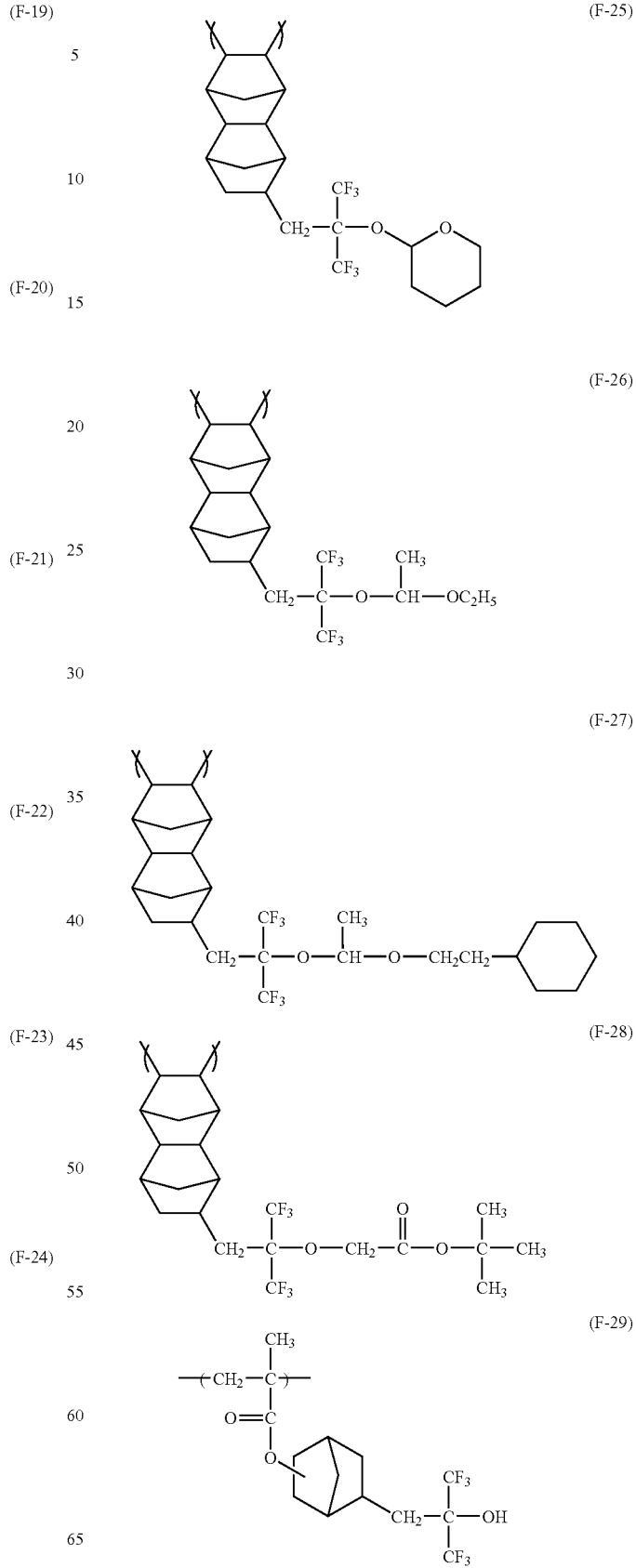

115
-continued
(F-30)
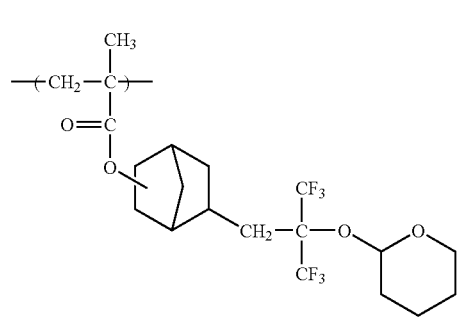
(F-31)
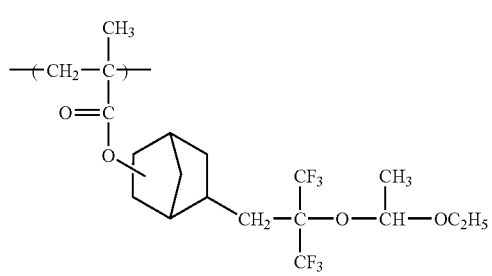
(F-32)
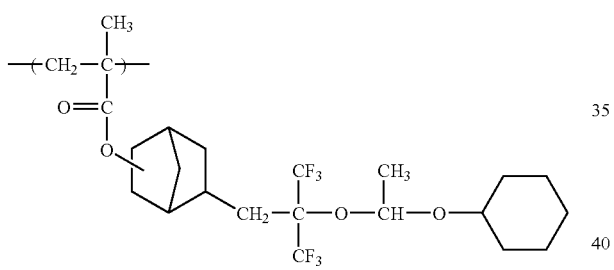
(F-33)
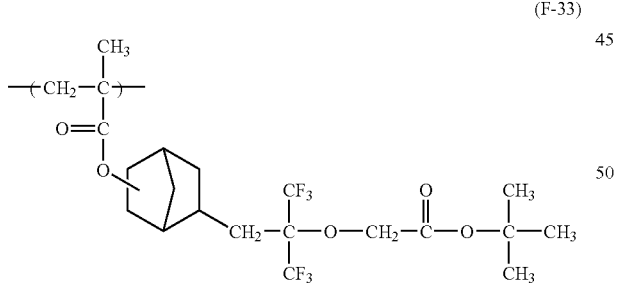
(F-34)
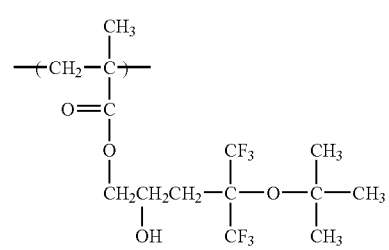
116
-continued
(F-35)
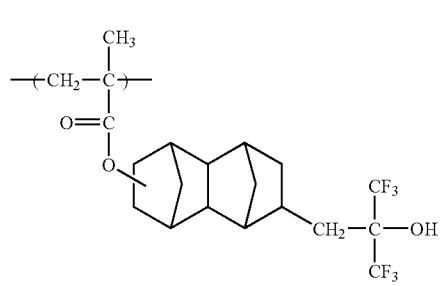
(F-36)
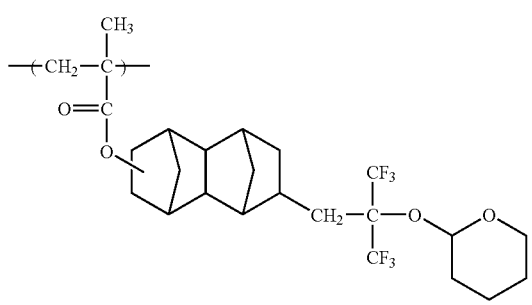
(F37)
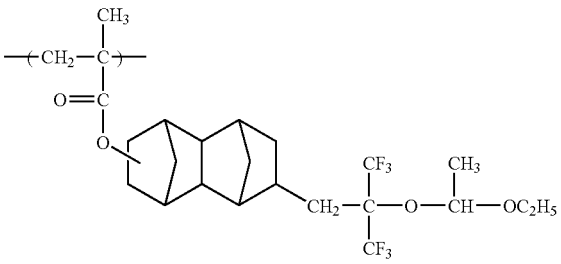
(F-38)
(F-39)
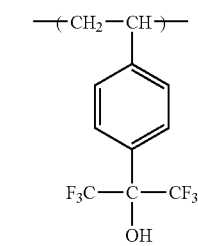

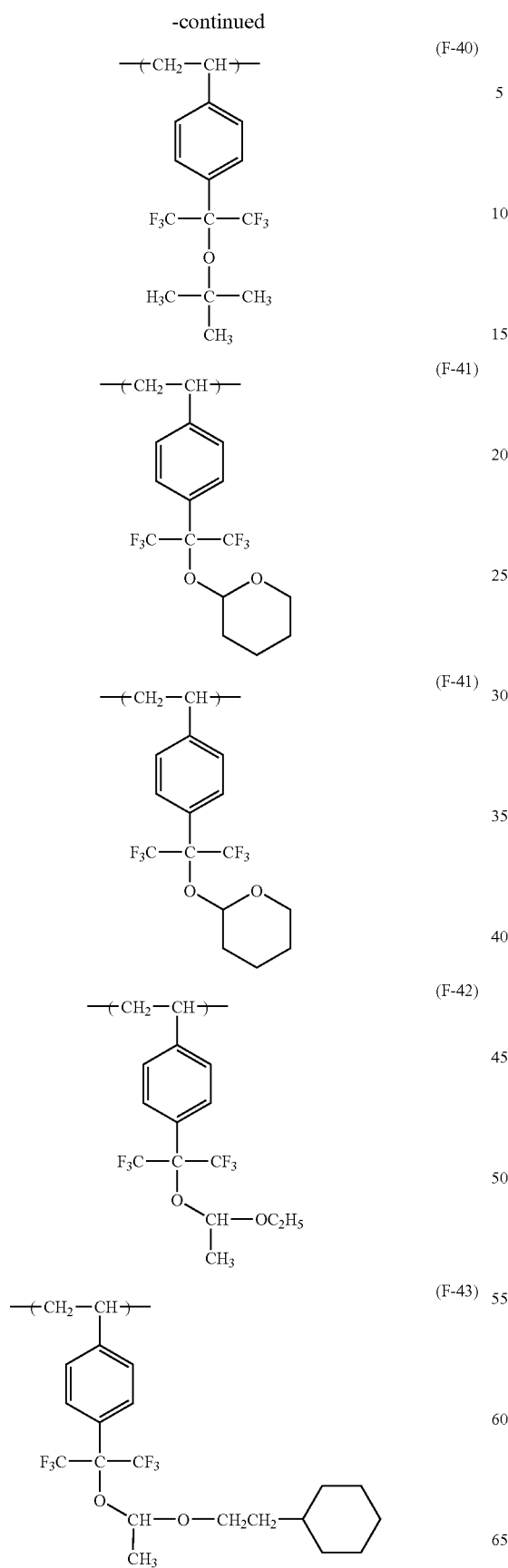
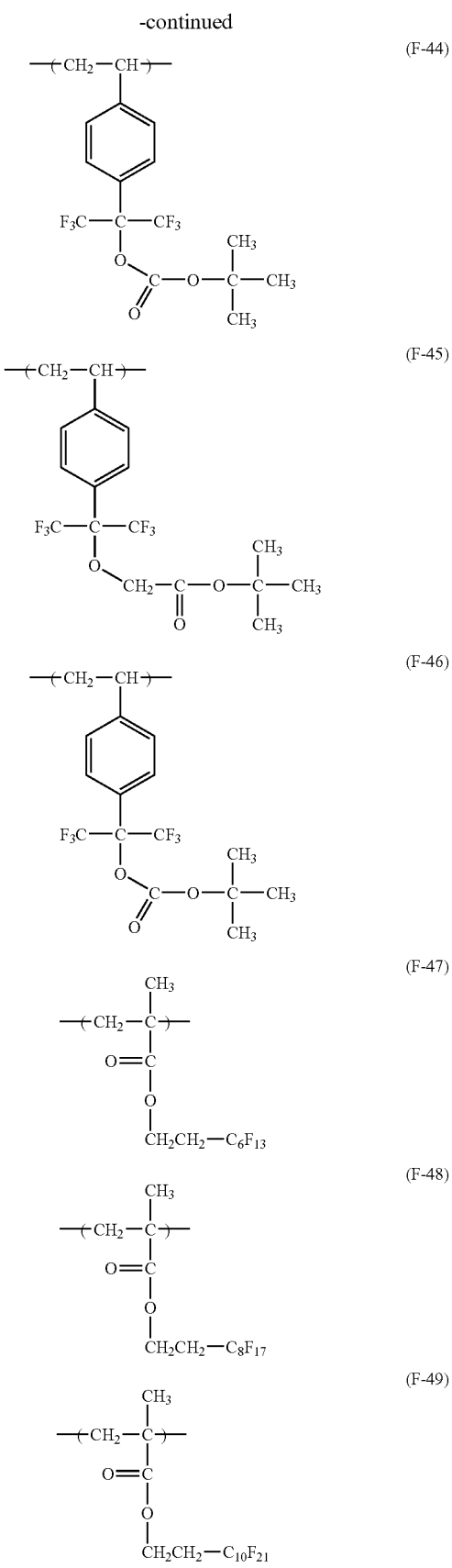

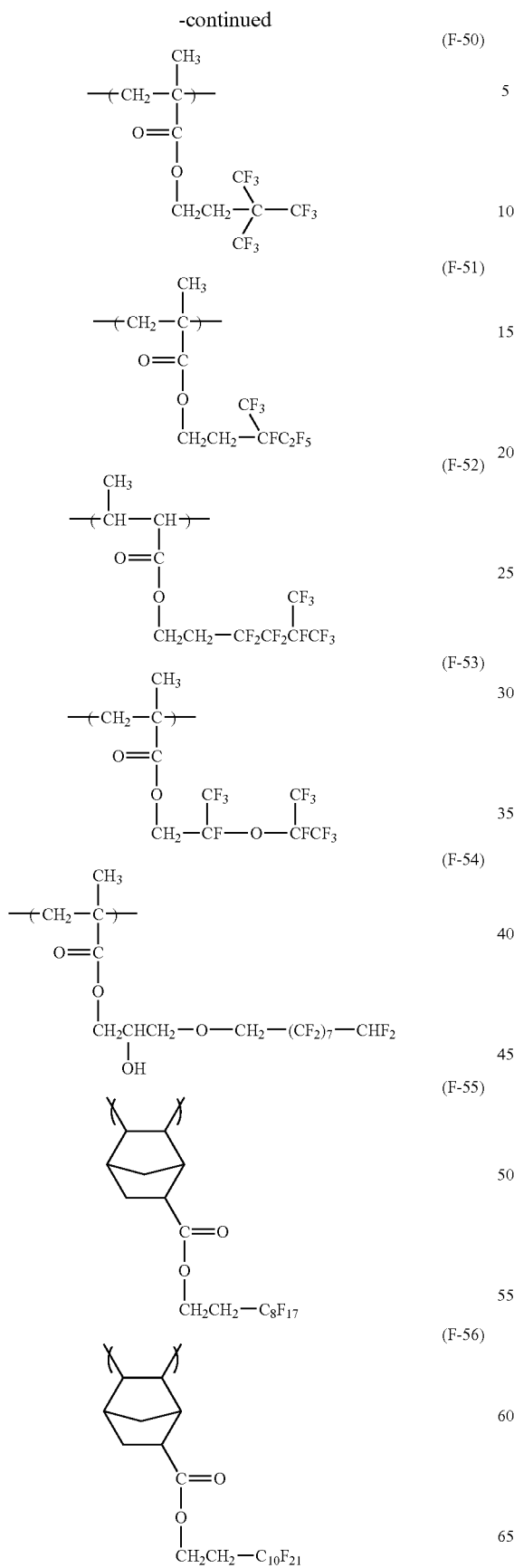
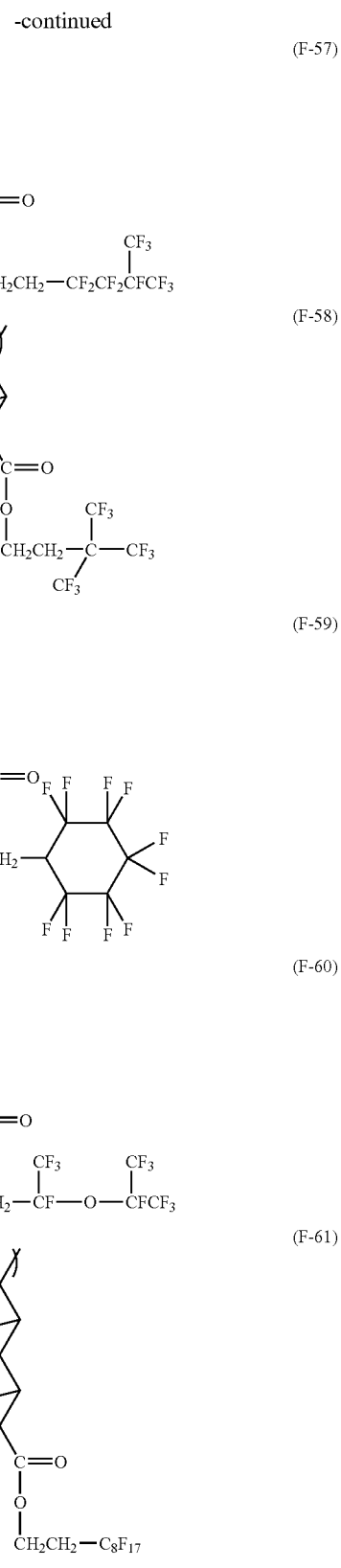

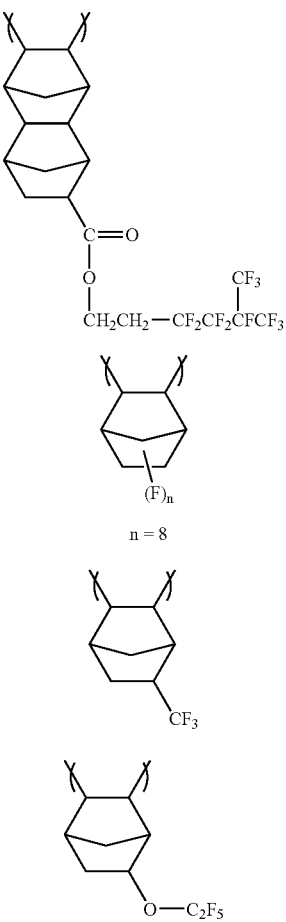

(F-62)

(F-63)

(F-64)

n = 8

(F-65)

The total content of the repeating units represented by formulae (FA) to (FG) is generally from 10 to 80 mol % to all the repeating units constituting the resin, preferably from 30 to 70 mol %, and more preferably from 35 to 65 mol %.

For the purpose of further improving the performances of the resist of the invention, the above resins may further be copolymerized with other polymerizable monomers in addition to the above repeating structural units.

As the usable copolymerizable monomers, compounds having one addition polymerizable unsaturated bond selected from acrylic esters, acrylamides, methacrylic esters, methacryl-amides, allyl compounds, vinyl ethers, vinyl esters, styrens, and crotonic esters other than described above are exemplified.

It is preferred that these fluorine-containing resins contain other repeating units as the copolymerization components besides the above repeating units containing fluorine atoms from the points of improving dry etching resistance, adjusting alkali solubility, and improving adhesion with substrates. Preferred other repeating units are as follows.

1) The repeating units having an alicyclic hydrocarbon structure represented by formula (II-AB) and any of formulae (pI) to (pVI). Specifically repeating units 1 to 23 and repeating units [II-1] to [II-32] shown above. Preferably repeating units 1 to 23, wherein Rx represents $CF_3$.

2) The repeating units having a lactone structure represented by formula (Lc) and any of formulae (V-1) to (V-5). Specifically the above-exemplified repeating units, in particular, the above-exemplified repeating units represented by formula (Lc) and formulae (V-1) to (V-4).

3) The repeating units derived from the vinyl compounds having maleic anhydride, vinyl ether or a cyano group represented by the following formula (XV), (XVI) or (XVII). Specifically repeating units (C-1) to (C-15) shown below. These repeating units may or may not contain a fluorine atom.

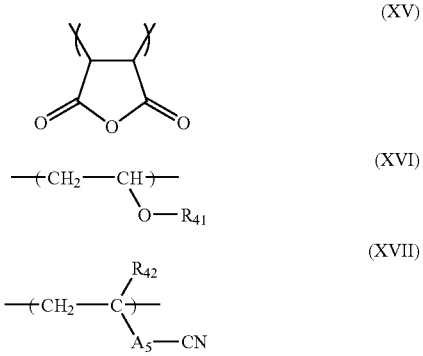

In each of the above formulae, $R_{41}$ represents an alkyl group, a cycloalkyl group, an aralkyl group or an aryl group, and the alkyl group represented by $R_{41}$ may be substituted with an aryl group.

$R_{42}$ represents a hydrogen atom, a halogen atom, a cyano group or an alkyl group.

$A_5$ represents a single bond, a divalent alkylene group, alkenylene group, cycloalkylene group or arylene group, or —O—CO—$R_{22}$—, —CO—O—$R_{23}$— or —CO—N($R_{24}$)—$R_{25}$—.

$R_{22}$, $R_{23}$ and $R_{25}$, which may be the same or different, each represents a single bond, or a divalent alkylene group, alkenylene group, cycloalkylene group or arylene group which may have an ether group, an ester group, an amido group, a urethane group or a ureido group.

$R_{24}$ represents a hydrogen atom, an alkyl group, a cycloalkyl group, an aralkyl group or an aryl group.

Here, the examples of the substituents are the same as the substituents in formulae (FA) to (FG).

The specific examples of the repeating structural units represented by formulae (XV) to (XVII) are shown below, but the invention is not limited thereto.

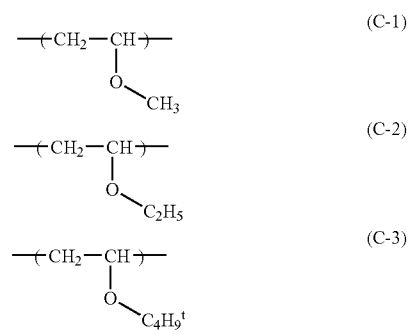

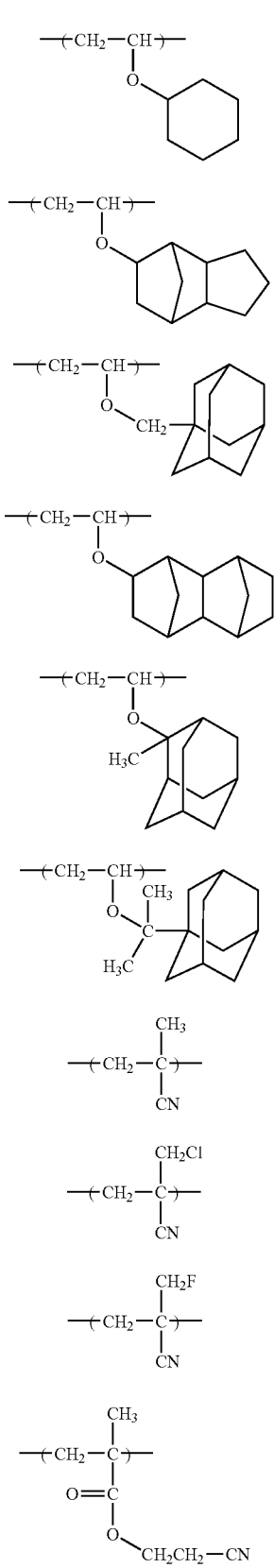

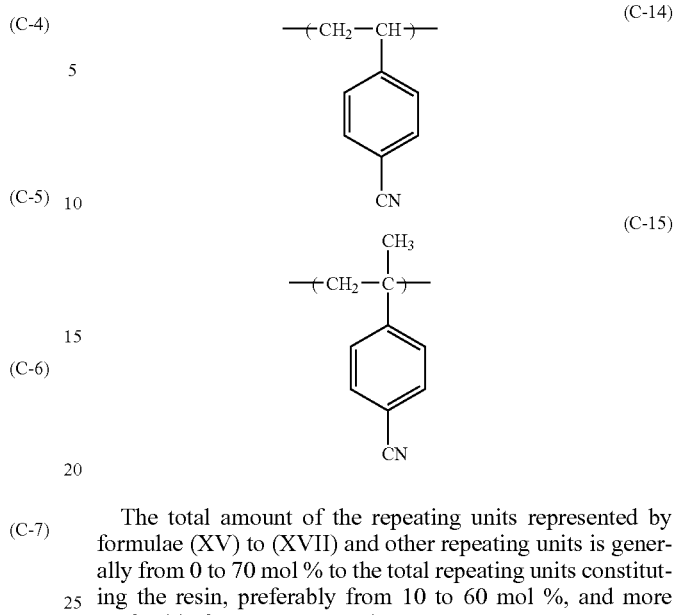

The total amount of the repeating units represented by formulae (XV) to (XVII) and other repeating units is generally from 0 to 70 mol % to the total repeating units constituting the resin, preferably from 10 to 60 mol %, and more preferably from 20 to 50 mol %.

A fluorine group-containing resin as the acid-decomposable resin may contain the acid-decomposable group in any repeating unit.

The proportion of a repeating unit having an acid decomposable group is preferably from 10 to 70 mol % to the total repeating units, more preferably from 20 to 60 mol %, and still more preferably from 30 to 60 mol %.

A fluorine group-containing resin can be synthesized by radical polymerization almost similar to the synthesis of alicyclic hydrocarbon-based acid-decomposable resin.

The weight average molecular weight of the fluorine-containing resin is preferably from 1,000 to 200,000 as the polystyrene equivalent by the GPC method. By making the weight average molecular weight 1,000 or more, heat resistance and dry etching resistance can be improved, and by making the weight average molecular weight 200,000 or less, developability can be improved, and film-forming property can be heightened, since the viscosity becomes extremely low.

In the positive photosensitive composition in the invention, the proportion of the resin of component (B) in all the composition is preferably from 40 to 99.99 mass % in the total solids content, more preferably from 50 to 99.97 mass %.

[3] (C) A Dissolution-inhibiting Compound Having a Molecular Weight of 3,000 or Less and Capable of Decomposing by the Action of an Acid to thereby Increase the Solubility in an Alkali Developer (Hereinafter also Referred to as "a Dissolution-inhibiting Compound):

As (C) the dissolution inhibiting compound having a molecular weight of 3,000 or less capable of decomposing by the action of an acid to thereby increase the solubility in an alkali developer, alicyclic or aliphatic compounds containing acid-decomposable groups, such as cholic acid derivatives containing acid-decomposable groups described in *Processing of SPIE*, 2724, 355 (1996) are preferred so as not to reduce the permeability of lights of 220 nm or less. As acid-decomposable groups and alicyclic structures, the same as those described above in the alicyclic hydrocarbon-based acid-decomposable resin are exemplified.

When the photosensitive composition according to the invention is exposed with a KrF excimer laser or irradiated with electron beams, it is preferred for the photosensitive composition to have a structure that the phenolic hydroxyl group of the phenolic compound is substituted with an acid-decomposable group. As the phenolic compounds, compounds having from 1 to 9 phenolic skeletons are preferred, and those having from 2 to 6 are more preferred.

The molecular weight of the dissolution-inhibiting compound in the invention is 3,000 or less, preferably from 300 to 3,000, and more preferably from 500 to 2,500.

The addition amount of the dissolution-inhibiting compound is preferably from 3 to 50 mass % based on the solids content of the photosensitive composition, and more preferably from 5 to 40 mass %.

The specific examples of the dissolution-inhibiting compounds are shown below, but the invention is not limited thereto.

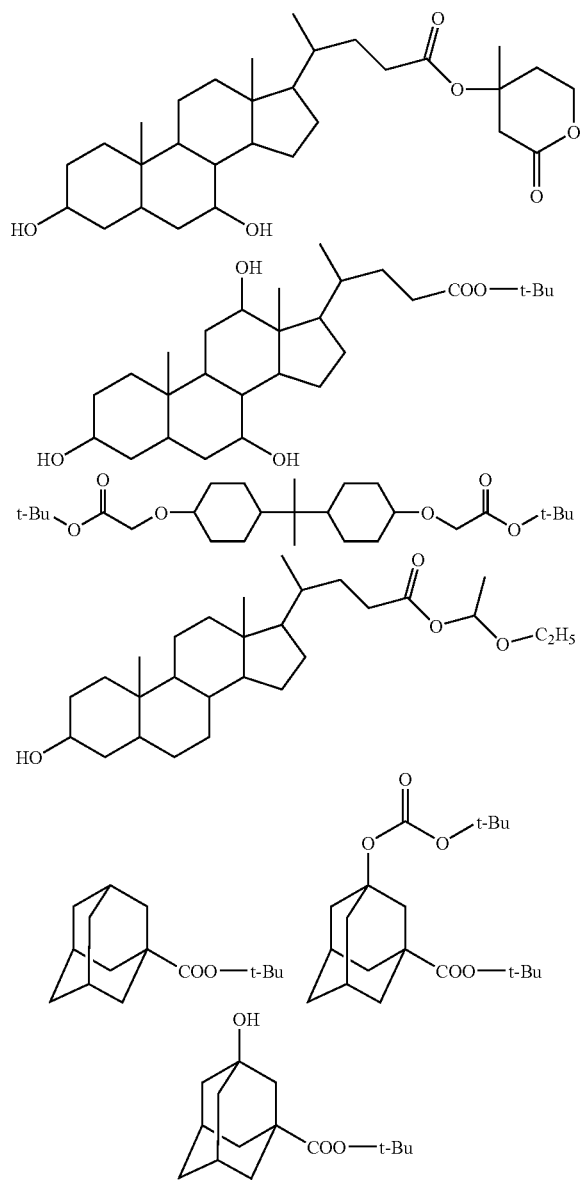

[4] (D) A Resin Soluble in an Alkali Developer (Hereinafter also Referred to as "Component (D)" or "Alkali-soluble Resin"):

The alkali dissolution rate of alkali-soluble resins is preferably 20 Å/sec or more when measured using 0.261 N tetramethylammonium hydroxide (TMAH) at 23° C., particularly preferably 200 Å/sec or more.

As alkali-soluble resins for use in the invention, e.g., novolak resins, hydrogenated novolak resins, acetone-pyrogallol resins, o-polyhydroxystyrene, m-polyhydroxy-styrene, p-polyhydroxystyrene, hydrogenated polyhydroxy-styrene, halogen- or alkyl-substituted polyhydroxystyrene, hydroxystyrene-N-substituted maleimide copolymers, o/p- and m/p-hydroxystyrene copolymers, partially O-alkylated products of the hydroxyl group of polyhydroxystyrene (e.g., from 5 to 30 mol % O-methylated, O-(1-methoxy)ethylated, O-(1-ethoxy)ethylated, O-2-tetrahydropyranylated, and O-(t-butoxycarbonyl)methylated products), or partially O-acylated products (e.g., from 5 to 30 mol % O-acetylated and O-(t-butoxy)carbonylated products), styrene-maleic anhydride copolymers, styrene-hydroxystyrene copolymers, α-methylstyrene-hydroxystyrene copolymers, carboxyl group-containing methacrylic resins and derivatives thereof, and polyvinyl alcohol derivatives can be exemplified, but the invention is not limited to these resins.

Particularly preferred alkali-soluble resins are novolak resins, o-polyhydroxystyrene, m-polyhydroxystyrene p-polyhydroxystyrene, copolymers of them, alkyl-substituted polyhydroxystyrene, partially O-alkylated or O-acylated products of polyhydroxystyrene, styrene-hydroxystyrene copolymers, and α-methylstyrene-hydroxystyrene copolymers.

The novolak resins can be obtained by addition condensation to aldehydes with the prescribed monomers as main components in the presence of acid catalysts.

The weight average molecular weight of alkali-soluble resins is 2,000 or more, preferably from 5,000 to 200,000, and more preferably from 5,000 to 100,000.

Here, the weight average molecular weight is defined as the polystyrene equivalent by gel permeation chromatography method.

Alkali-soluble resins (D) may be used in combination of two kinds or more in the invention.

The addition amount of alkali-soluble resins is from 40 to 97 mass %, preferably from 60 to 90 mass %, based on the total solids content of the photosensitive composition.

[5] (E) An Acid Crosslinking Agent Capable of Crosslinking with the Alkali-Soluble Resin by the Action of an Acid (Hereinafter also Referred to as "Component (E)" or "Crosslinking Agent"):

Crosslinking agents are used in the negative photosensitive composition of the invention.

Any compound capable of crosslinking the resins soluble in an alkali developer by the action of an acid can be used as crosslinking agents, but the following (1) to (3) are preferably used.

(1) Hydroxymethyl body, alkoxymethyl body and acyloxymethyl body of phenol derivatives
(2) Compounds having an N-hydroxymethyl group, an N-alkoxy-methyl group or an N-acyloxymethyl group
(3) Compounds having an epoxy group As the alkoxymethyl groups, those having 6 or less carbon atoms, and as the acyloxymethyl groups, those having 6 or less carbon atoms are preferred.

Of these crosslinking agents, particularly preferred compounds are shown below.

127
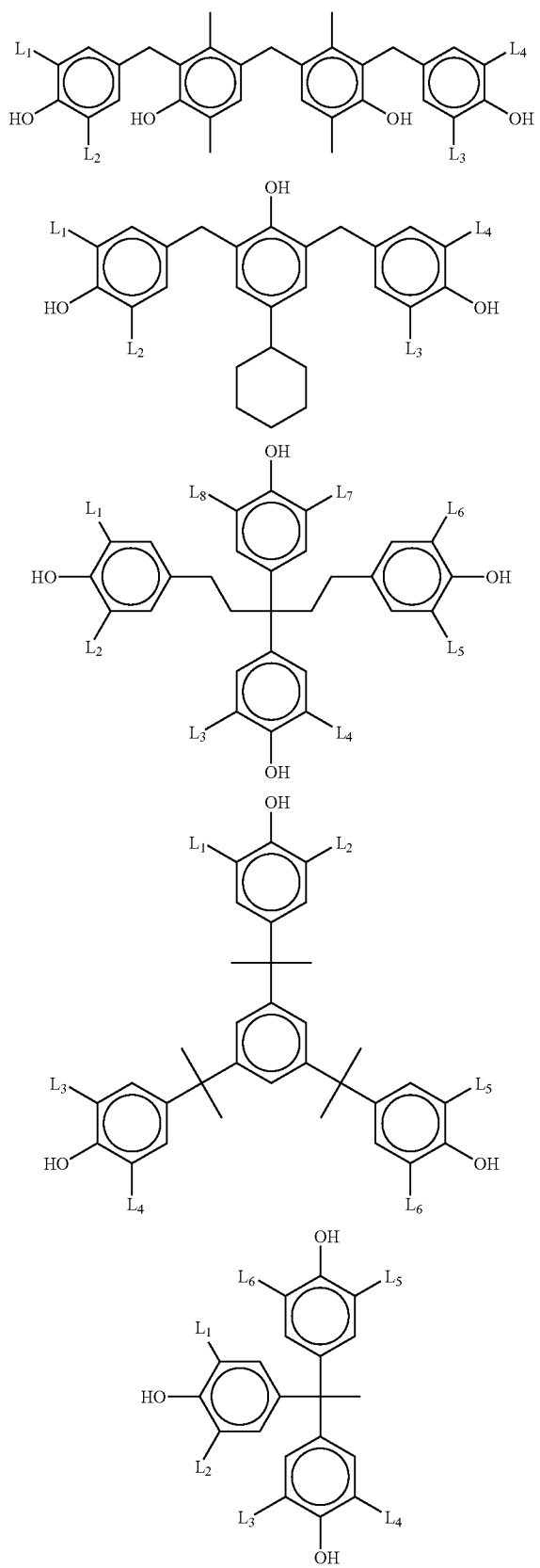
128
-continued
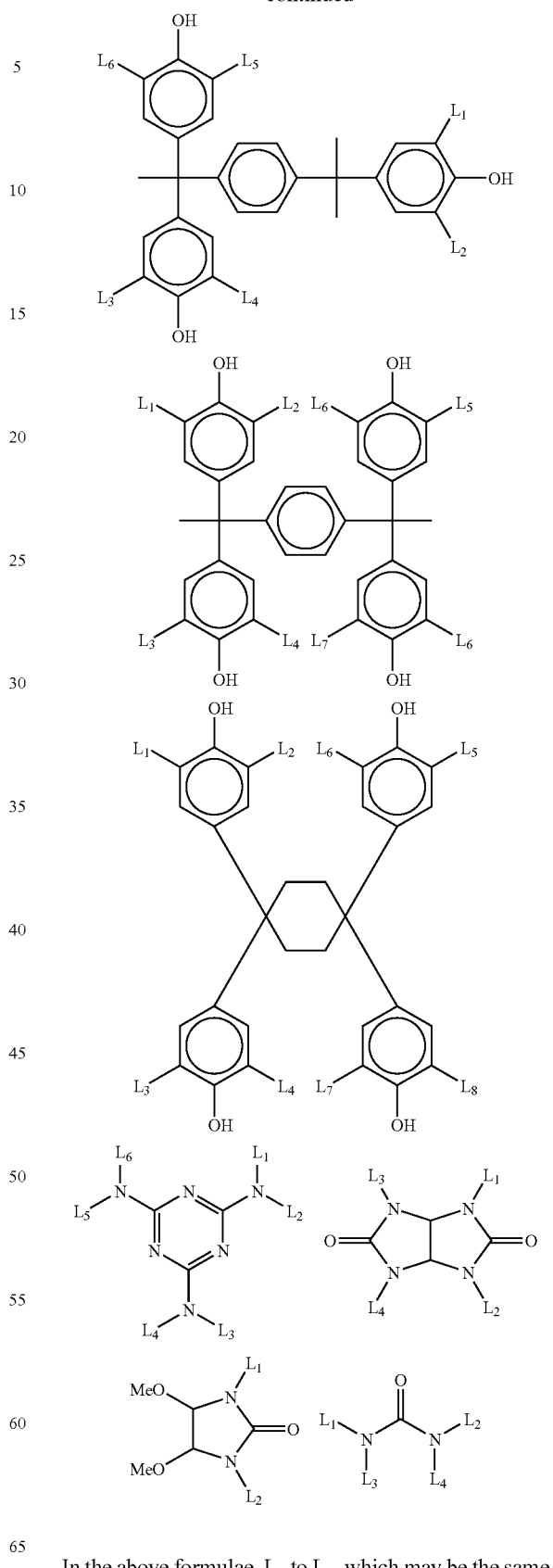
In the above formulae, $L_1$ to $L_8$, which may be the same or different, each represents a hydrogen atom, a hydroxymethyl group, a methoxymethyl group, an ethoxymethyl group, or an alkyl group having from 1 to 6 carbon atoms.

Crosslinking agents are used generally in proportion of from 3 to 70 mass % in the solids content of the photosensitive composition, preferably from 5 to 50 mass %.

Other Components:

[6] (F) Basic Compounds:

For decreasing the fluctuation of performances during the period of time from exposure to baking, it is preferred for the photosensitive composition of the invention to contain (F) basic compounds.

As the preferred structures of basic compounds, the structures represented by the following formulae (A) to (E) can be exemplified.

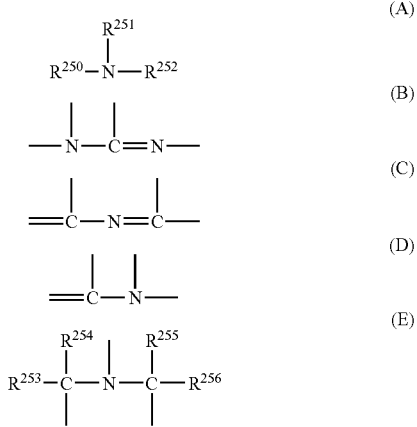

In formula (A), $R_{250}$, $R_{251}$ and $R_{252}$ each represents a hydrogen atom, an alkyl group having from 1 to 20 carbon atoms, a cycloalkyl group having from 3 to 20 carbon atoms, or an aryl group having from 6 to 20 carbon atoms, and $R_{250}$ and $R_{251}$ may be bonded to each other to form a ring. These groups may have a substituent, and as the alkyl group and the cycloalkyl group having a substituent, an aminoalkyl group having from 1 to 20 carbon atoms or an aminocycloalkyl group having from 3 to 20 carbon atoms, a hydroxyalkyl group having from 1 to 20 carbon atoms or a hydroxycycloalkyl group having from 3 to 20 carbon atoms are preferred.

These groups may contain an oxygen atom, a sulfur atom or a nitrogen atom in the alkyl chain.

In formula (E), $R_{253}$, $R_{254}$, $R_{255}$ and $R_{256}$ each represents an alkyl group having from 1 to 6 carbon atoms, or a cycloalkyl group having from 3 to 6 carbon atoms.

As preferred examples of basic compounds, guanidine, aminopyrrolidine, pyrazole, pyrazoline, piperazine, aminomorpholine, aminoalkylmorpholine, and piperidine can be exemplified, and these compounds may have a substituent. As further preferred compounds, compounds having an imidazole structure, a diazabicyclo structure, an onium hydroxide structure, an onium carboxylate structure, a trialkylamine structure, an aniline structure and a pyridine structure, alkylamine derivatives having a hydroxyl group and/or an ether bond, and aniline derivatives having a hydroxyl group and/or an ether bond can be exemplified.

As compounds having an imidazole structure, imidazole, 2,4,5-triphenylimidazole and benzimidazole can be exemplified. As compounds having a diazabicyclo structure, 1,4-diazabicyclo[2,2,2]octane, 1,5-diazabicyclo[4,3,0]non-5-ene, and 1,8-diazabicyclo[5,4,0]undeca-7-ene can be exemplified. As compounds having an onium hydroxide structure, triarylsulfonium hydroxide, phenacylsulfonium hydroxide, sulfonium hydroxide having a 2-oxoalkyl group, specifically triphenyl-sulfonium hydroxide, tris(t-butylphenyl)sulfonium hydroxide, bis(t-butylphenyl)iodonium hydroxide, phenacylthiophenium hydroxide, and 2-oxopropylthiophenium hydroxide can be exemplified. Compounds having an onium carboxylate structure are compounds having an onium hydroxide structure in which the anionic part is carboxylated, e.g., acetate, adamantane-1-carboxylate and perfluoroalkyl carboxylate are exemplified. As compounds having a trialkylamine structure, tri(n-butyl)-amine and tri(n-octyl)amine can be exemplified. As aniline compounds, 2,6-diisopropylaniline and N,N-dimethylaniline can be exemplified. As alkylamine derivatives having a hydroxyl group and/or an ether bond, ethanolamine, diethanol-amine, triethanolamine and tris(methoxyethoxyethyl)amine can be exemplified. As aniline derivatives having a hydroxyl group and/or an ether bond, N,N-bis(hydroxyethyl)aniline can be exemplified.

These basic compounds are used alone or in combination of two or more. The use amount of basic compounds is generally from 0.001 to 10 mass % based on the solids content of the photosensitive composition, and preferably from 0.01 to 5 mass %. For obtaining a sufficient addition effect, the addition amount is preferably 0.001 mass % or more, and in view of sensitivity and the developability of a non-exposed area, the addition amount is preferably 10 mass % or less.

[7] (G) Fluorine and/or Silicon Surfactants:

It is preferred for the photosensitive composition in the invention to further contain either one or two or more of fluorine and/or silicon surfactants (a fluorine surfactant and a silicon surfactant, a surfactant containing both a fluorine atom and a silicon atom).

By containing fluorine and/or silicon surfactants, it becomes possible for the photosensitive in the invention to provide a resist pattern excellent in sensitivity and resolution, and low in adhesion defect and development defect in using an exposure light source of 250 nm or lower, in particular, 220 nm or lower.

These fluorine and/or silicon surfactants are disclosed, e.g., in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862, U.S. Pat. Nos. 5,405,720, 5,360,692, 5,529,881, 5,296,330, 5,436,098, 5,576,143, 5,294,511 and 5,824,451. The following commercially available surfactants can also be used as they are.

As commercially available fluorine and silicon surfactants usable in the invention, Eftop EF301 and EF303 (manufactured by Shin-Akita Kasei Co., Ltd.), Fluorad FC 430 and 431 (manufactured by Sumitomo 3M Limited), Megafac F171, F173, F176, F189 and R08 (manufactured by Dainippon Ink and Chemicals Inc.), Sarfron S-382, SC101, 102, 103, 104, 105 and 106 (manufactured by ASAHI GLASS CO., LTD.), and Troy Sol S-366 (manufactured by Troy Chemical Co., Ltd.) are exemplified. In addition, polysiloxane polymer KP-341 (manufactured by Shin-Etsu Chemical Co., Ltd.) can also be used as a silicon surfactant.

As surfactants, in addition to the above-shown well known surfactants, surfactants using polymers having fluoro-aliphatic groups derived from fluoro-aliphatic compounds manufactured by a telomerization method (also called a telomer method) or an oligomerization method (also called an oligomer method) can be used. Fluoro-aliphatic compounds can be synthesized according to the method disclosed in JP-A-2002-90991.

As polymers having fluoro-aliphatic groups, copolymers of monomers having fluoro-aliphatic groups and (poly(oxyalkylene))acrylate and/or (poly(oxyalkylene))methacrylate are preferred, and these copolymers may be irregularly distributed or may be block copolymerized. As the poly-(oxyalkylene) groups, a poly(oxyethylene) group, a poly-(oxypropylene) group and poly(oxybutylene) group are exemplified. Further, the polymers may be units having alkylene different in a chain length in the same chain length, such as a block combination of poly(oxyethylene and oxypropylene and oxyethylene), and a block combination of poly(oxyethylene and oxypropylene). In addition, copolymers of monomers having fluoro-aliphatic groups and poly-(oxyalkylene)acrylate (or methacrylate) may be not only bipolymers but also terpolymers or higher polymers obtained by copolymerization of monomers having different two or more kinds of fluoro-aliphatic groups and different two or more kinds of poly (oxyalkylene)acrylates (or methacrylates) at the same time.

For example, as commercially available surfactants, Megafac F178, F470, F473, F475, F476 and F472 (manufactured by Dainippon Ink and Chemicals Inc.) can be exemplified. Further, copolymers of acrylate (or methacrylate) having a $C_6F_{13}$ group and (poly(oxyalkylene))acrylate (or methacrylate), copolymers of acrylate (or methacrylate) having a $C_6F_{13}$ group, (poly(oxyethylene))acrylate (or methacrylate), and (poly-(oxypropylene))acrylate (or methacrylate), copolymers of acrylate (or methacrylate) having a $C_8F_{17}$ group and (poly-(oxyalkylene))acrylate (or methacrylate), and copolymers of acrylate (or methacrylate) having a $C_8F_{17}$ group, (poly(oxy-ethylene))acrylate (or methacrylate), and poly(oxypropylene)acrylate (or methacrylate) are exemplified.

The amount of fluorine and/or silicon surfactants is preferably from 0.0001 to 2 mass % to the total amount of the photosensitive composition (excluding solvents), more preferably from 0.001 to 1 mass %.

[8] (H) Organic Solvent:

The above components of the photosensitive composition of the invention are dissolved in a prescribed organic solvent.

As the organic solvents usable in the invention, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methylmethoxy propionate, ethylethoxy propionate, methyl pyruvate, ethyl pyruvate, propyl pyruvate, N,N-dimethylformamide, dimethyl sulfoxide, N-methylpyrrolidone, and tetrahydrofuran are exemplified.

Organic solvents may be used alone or as mixed solvents, but it is preferred in the invention to use a mixed solvent of a solvent containing a hydroxyl group in the structure and a solvent not containing a hydroxyl group, by which the generation of particles during the preservation of a resist solution can be reduced.

As solvents containing a hydroxyl group, e.g., ethylene glycol, ethylene glycol monomethyl ether, ethylene glycol monoethyl ether, propylene glycol, propylene glycol monomethyl ether, propylene glycol monoethyl ether and ethyl lactate are exemplified. Of these solvents, propylene glycol monomethyl ether and ethyl lactate are particularly preferred.

As solvents not containing a hydroxyl group, e.g., propylene glycol monomethyl ether acetate, ethylethoxy propionate, 2-heptanone, γ-butyrolactone, cyclohexanone, butyl acetate, N-methylpyrrolidone, N,N-dimethylacetamide, and dimethyl sulfoxide are exemplified. Of these solvents, propylene glycol monomethyl ether acetate, ethylethoxy propionate, 2-heptanone, γ-butyrolactone, cyclohexanone and butyl acetate are particularly preferred, and propylene glycol monomethyl ether acetate, ethylethoxy propionate and 2-heptanone are most preferred.

The mixing ratio (by mass) of a solvent containing a hydroxyl group and a solvent not containing a hydroxyl group is from 1/99 to 99/1, preferably from 10/90 to 90/10, and more preferably from 20/80 to 60/40. A mixed solvent containing 50 mass % or more of a solvent not containing a hydroxyl group is particularly preferred in the point of coating uniformity.

Other Additives:

If necessary, dyes, plasticizers, surfactants other than the surfactants of component (G), photosensitizers, and compounds for expediting the dissolution of composition in a developer may be further added to the photosensitive composition in the present invention.

Compounds for expediting dissolution in a developer that can be used in the invention are low molecular weight compounds having a molecular weight of 1,000 or less and having two or more phenolic OH groups or one or more carboxyl groups. When carboxyl groups are contained, alicyclic or aliphatic compounds are preferred.

The preferred addition amount of these dissolution accelerating compounds is preferably from 2 to 50 mass % based on the addition amount of the resin of component (B) or the resin of component (D), more preferably from 5 to 30 mass %. The amount is preferably 50 mass % or less in the point of restraint of development residue and prevention of pattern deformation in development.

These phenolic compounds having a molecular weight of 1,000 or less can be easily synthesized with referring to the methods disclosed, e.g., in JP-A-4-122938, JP-A-2-28531, U.S. Pat. No. 4,916,210, and EP 219294.

As the specific examples of the alicyclic or aliphatic compounds having carboxyl groups, carboxylic acid derivatives having a steroid structure, e.g., cholic acid, deoxycholic acid, and lithocholic acid, adamantanecarboxylic acid derivatives, adamantanedicarboxylic acid, cyclohexanecarboxylic acid, and cyclohexanedicarboxylic acid are exemplified, but the invention is not limited to these compounds.

Surfactants other than fluorine and/or silicon surfactants of component (G) can be used in the invention. As the specific examples of other surfactants, nonionic surfactants, e.g., polyoxyethylene alkyl ethers, polyoxy-ethylene alkylaryl ethers, polyoxyethylene-polyoxypropylene block copolymers, sorbitan aliphatic acid esters, and polyoxyethylene sorbitan aliphatic acid esters can be exemplified.

These surfactants may be used alone or in combination of two or more.

Pattern Forming Method:

The photosensitive composition in the invention is used by dissolving each of the above components in a prescribed organic solvent, preferably dissolving in a mixed solvent as described above, and coating the solution on a prescribed support as follows.

For example, the photosensitive composition is coated on a substrate such as the one used in the manufacture of precision integrated circuit element (e.g., silicon/silicon dioxide coating) by an appropriate coating method with a spinner or a coater, and dried, to thereby form a resist film.

The resist film is then irradiated with an actinic ray or radiation through a prescribed mask, the exposed resist film is preferably subjected to baking (heating), development and rinse, whereby a good pattern can be obtained.

As actinic rays or radiation, infrared rays, visible rays, ultraviolet rays, far ultraviolet rays, X-rays and electron beams can be exemplified, preferably far ultraviolet rays of the wavelengths of 250 nm or less, and more preferably 220 nm or less. Specifically, a KrF excimer laser (248 nm), an ArF excimer laser (193 nm), an $F_2$ excimer laser (157 nm), X-rays and electron beams are exemplified, and ArF excimer lasers, $F_2$ excimer lasers, EUV (13 nm), and electron beams are preferably used.

In a development process, an alkali developer is used as follows. As the alkali developer of the resist composition, alkaline aqueous solutions of inorganic alkalis, e.g., sodium hydroxide, potassium hydroxide, sodium carbonate, sodium silicate, sodium metasilicate and aqueous ammonia, primary amines, e.g., ethylamine and n-propylamine, secondary amines, e.g., diethylamine and di-n-butylamine, tertiary amines, e.g., triethylamine and methyldiethylamine, alcohol amines, e.g., dimethylethanolamine and triethanol-amine, quaternary ammonium salts, e.g., tetramethylammonium hydroxide and tetraethylammonium hydroxide, and cyclic amines, e.g., pyrrole and piperidine, can be used.

An appropriate amount of alcohols and surfactants may be added to these alkali developers.

The alkali concentration of alkali developers is generally from 0.1 to 20 mass %.

The pH of alkali developers is generally from 10.0 to 15.0.

EXAMPLES

The present invention is described in greater detail below, but the present invention is not limited thereto.

Synthesis Example 1

Synthesis of 10-tolyl-9-oxothioxanthenium nonafluorobutanesulfonate (A1)

Thioxanthen-9-one (10 g) was stirred in 40 ml of trifluoroacetic acid, and a solution prepared by mixing 5.4 ml of aqueous 30% hydrogen peroxide and 10.8 ml of trifluoroacetic acid was gradually added thereto under ice cooling. The resulting solution was stirred for 30 minutes under ice cooling and then stirred at room temperature for 1 hour. The reaction solution obtained was poured in water, and the crystal precipitated was collected by filtration. The obtained crystal was recrystallized from acetonitrile to obtain 4.6 g of a sulfoxide form. Subsequently, 3 g of the sulfoxide form was stirred in 20 ml of toluene, and 3.7 ml of trifluoroacetic anhydride and 2.2 ml nonafluorobutanesulfonic acid were added thereto under ice cooling. The reaction solution obtained was gradually heated to room temperature and then stirred for 1 hour. The crystal was precipitated by adding diisopropyl ether to the reaction solution and then recrystallized from a mixed solvent of ethyl acetate and diisopropyl ether to obtain 3.9 g of 10-tolyl-9-oxothioxanthenium nonafluorobutanesulfonate. $^1$H-NMR (400 MHz, CDCl$_3$): δ 2.38 (s, 3H), 7.34 (d, 2H), 7.72 (m, 2H), 7.95 (m, 4H), 8.28 (m, 2H), 8.63 (d, 2H).

Synthesis Example 2

Synthesis of 10-tolyl-9-oxothioxanthenium 3,5-bistrifluoromethylbenzenesulfonate (A2)

Using 1.5 g of 10-tolyl-9-oxothioxanthenium nonafluorobutanesulfonate (A1) obtained in Synthesis Example 1, 1.5 g of 10-tolyl-9-oxothioxanthenium nonafluorobutanesulfonate was dissolved in a methanol/water (=1/1) solution, and the resulting solution was passed through an ion exchange resin (Amberlite IRA402C1 in which the anion is replaced by OH with use of aqueous NaOH). After adding 1 g of 3,5-bistrifluoromethylbenzenesulfonic acid thereto, the solution was extracted with chloroform to obtain 1.7 g of 10-tolyl-9-oxothioxanthenium 3,5-bistrifluoromethylbenzenesulfonate as a compound changed in the counter salt. $^1$H-NMR (400 MHz, CDCl$_3$): δ 2.37 (s, 3H), 7.34 (d, 2H), 7.79 (m, 3H), 7.93 (m, 4H), 8.34 (m, 4H), 8.62 (d, 2H).

Synthesis Example 3

Synthesis of 2-acetyl-10-tolyl-9-oxothioxanthenium nonafluorobutanesulfonate (A8)

Thiosalicylic acid (15 g) and 20 g of 4-bromoacetophenone were stirred in 200 ml of dimethylformamide in the presence of 12 g of sodium carbonate and 0.2 g of copper catalyst at 170° C. for 6 hours, and the reaction solution obtained was poured in an aqueous hydrochloric acid solution and filtered. The collected crystal was recrystallized from acetonitrile to obtain 16 g of sulfide. Subsequently, 10 g of the sulfide obtained was stirred in 100 g of polyphosphoric acid at 60° C. for 5 hours and then poured in ice water. The crystal was collected by filtration, washed with an aqueous sodium hydrogencarbonate solution and water, and then recrystallized from ethanol to obtain 5 g of 2-acetyl-9H-thioxan-9-one. Furthermore, 3 g of 2-acetyl-9H-thioxan-9-one obtained was stirred in 12 ml of trifluoroacetic acid under ice cooling, and a mixed solution containing 1.4 ml of aqueous 30% hydrogen peroxide and 2.7 ml of trifluoroacetic acid was gradually added thereto. After the addition, the solution was stirred for 30 minutes under ice cooling and then stirred at room temperature for 12 hours, thereby completing the reaction. The reaction solution obtained was poured in water and subjected to liquid separation with ethyl acetate and an aqueous sodium hydroxide solution, and the organic layer was removed by distillation under reduced pressure to obtain 3.6 g of a sulfoxide form. This sulfoxide form was stirred in 15 g of toluene, and 3.3 ml of trifluoroacetic anhydride and 1.9 ml of nonafluorobutanesulfonic acid were added thereto under ice cooling, followed by stirring for 30 minutes under ice cooling and then at room temperature for 1 hour. The reaction solution obtained was subjected to crystallization by adding diisopropyl ether, and the crystal obtained was recrystallized from a mixed solvent of ethyl acetate and diisopropyl ether to obtain 1 g of 2-acetyl-10-tolyl-9-oxothioxanthenium nonafluorobutanesulfonate (A8). $^1$H-NMR (400 MHz, CDCl$_3$): δ 2.39 (s, 3H), 2.74 (s, 3H), 7.37 (d, 2H), 7.72 (m, 2H), 7.97 (m, 2H), 8.19 (m, 1H), 8.39 (m, 2H), 8.67 (d, 1H), 9.09 (s, 1H).

Other sulfonium salts (A) were synthesized in the same manner.

Synthesis Example 4

Synthesis of (A40)

Thianthrene (20 g) was refluxed in 300 ml of acetic acid, and 36 ml of dilute nitric acid was gradually added dropwise thereto. After allowing the reaction to proceed for 5 hours, the reaction solution obtained was poured in 1.2 liter of water to precipitate a crystal. The crystal was collected by filtration and then recrystallized from acetonitrile to obtain 12 g of thianthrene-S-oxide. $^1$H-NMR (400 MHz, CDCl$_3$): δ 7.42 (t, 2H), 7.56 (t, 2H), 7.63 (d, 2H), 7.93 (d, 2H).

Subsequently, 2 g of thianthrene-S-oxide was dissolved in 10 ml of toluene and ice-cooled, and 2.8 ml of trifluoroacetic anhydride and 1.2 ml of nonafluorobutanesulfonic acid were added thereto, followed by stirring for 1 hour. Subsequently, diisopropyl ether was added thereto and after removing the supernatant, the residue was purified through a silica gel column (chloroform/methanol=19/1) to obtain 4.4 g of 5-(p-tolyl)thianthrenium nonafluorobutanesulfonate. $^1$H-NMR (400 MHz, CDCl$_3$): δ 2.34 (s, 3H), 7.08 (d, 2H), 7.22 (d, 2H), 7.78 (m, 6H), 8.65 (d, 2H).

Furthermore, 2 g of 5-(p-tolyl)thianthrenium nonafluorobutanesulfonate was suspended in 6 ml of trifluoroacetic acid, and 0.75 ml of aqueous 30% hydrogen peroxide was added dropwise thereto at room temperature. The resulting solution was stirred at 80° C. for 1 hour and then subjected to liquid separation by adding water and chloroform. The chloroform layer was removed by distillation under reduced pressure, and the residue was purified through a silica gel column (chloroform/methanol=19/1) to obtain 1.2 g of (A40). $^1$H-NMR (400 MHz, CDCl$_3$): δ 2.47 (s, 3H), 7.47 (d, 2H), 7.66 (d, 2H), 7.98 (t, 2H), 8.04 (t, 2H), 8.40 (d, 2H), 8.43 (d, 2H).

Synthesis Example 5

Synthesis of (A73)

Thianthrene-S-oxide (1 g) and 1.1 ml of ethoxybenzene were mixed and ice-cooled, and 1.2 ml of trifluoroacetic anhydride and 0.71 ml of nonafluorobutanesulfonic acid were added thereto, followed by stirring for 15 minutes. Subsequently, diisopropyl ether was added thereto and after removing the supernatant, the residue was subjected to liquid separation by adding chloroform and water. The chloroform layer was removed by distillation under reduced pressure to obtain 2.5 g of 5-(p-ethoxybenzene)thianthrenium nonafluorobutanesulfonate. $^1$H-NMR (400 MHz, CDCl$_3$): δ 1.38 (t, 3H), 4.00 (q, 2H), 6.92 (d, 2H), 7.29 (d, 2H), 7.75 (m, 6H), 8.56 (d, 2H).

Thereafter, 2.5 g of 5-(p-ethoxybenzene)thianthrenium nonafluorobutanesulfonate was suspended in 10 ml of trifluoroacetic acid and ice-cooled, and 0.89 ml of aqueous 30% hydrogen peroxide was added dropwise thereto, followed by stirring for 1 hour. After the reaction, the reaction solution obtained was poured in water and subjected to liquid separation by adding chloroform. The chloroform layer was removed by distillation under reduced pressure, and the residue was recrystallized from a mixed solvent of diisopropyl ether and ethyl acetate to obtain 1.3 g of (A73). $^1$H-NMR (400 MHz, CDCl$_3$): δ 1.47 (t, 3H), 4.20 (q, 2H), 7.26 (d, 2H), 7.91 (m, 6H), 7.98 (m, 2H), 8.39 (d, 2H).

<Resin (B)>

The structure and molecular weight of each resin (B) used in Examples are shown below.

| | Molecular Weight |
|---|---|
| (6) | 11300 |
| (7) | 8900 |
| (11) | 13400 |
| (15) | 9600 |
| (16) | 5800 |

-continued

| | | Molecular Weight |
|---|---|---|
| (17) | | 4700 |
| (20) | | 12100 |
| (24) | | 10800 |
| (25) | | 9300 |
| (28) | | 7300 |

-continued

| | | Molecular Weight |
|---|---|---|
| (29) 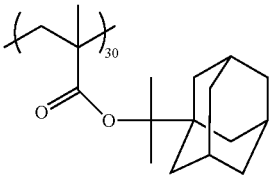 | | 7600 |
| (30) 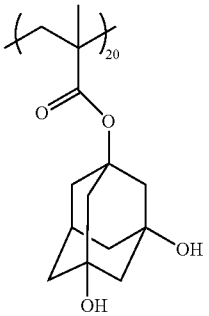 | | 8400 |
| (31) 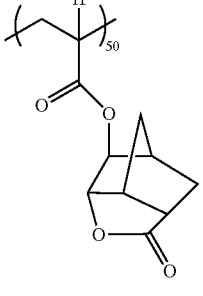 | | 6500 |

Examples Ar1 to Ar33 and Comparative Examples ar1 and ar2

<Preparation of Resist>

The components shown in Table 1 below were dissolved in a solvent to prepare a solution having a solid content concentration of 12 mass %, and this solution was filtered through a 0.1 μm polytetrafluoroethylene or polyethylene filter to prepare a positive resist solution. The prepared positive resist solutions were evaluated by the following method and the results are shown in Table 1.

<Evaluation of Resist>

On a silicon substrate treated with hexamethyldisilazane, an antireflection film, DUV-42, produced by Brewer Science, Inc. was uniformly coated to a thickness of 600 angstroms by a spin coater, then dried at 100° C. for 90 seconds on a hot plate and further dried under heating at 190° C. for 240 seconds. Thereafter, each of the positive resist compositions was coated thereon by a spin coater and dried at 120° C. for 90 seconds to form a resist film of 0.03 μm.

The resist film formed was exposed by an ArF excimer laser stepper (manufactured by ISI Co., Ltd.; NA=0.6) through a mask and immediately after the exposure, heated at 120° C. for 90 seconds on a hot plate. Furthermore, the resist film was developed with an aqueous 2.38 mass % tetramethylammonium hydroxide solution at 23° C. for 60 seconds, rinsed with pure water for 30 seconds and then dried to obtain a line pattern.

(Sensitivity)

The sensitivity was expressed by an exposure amount necessary for reproducing a line-and-space (1:1) pattern having a line width of 130 nm.

TABLE 1

| | (A) Acid Generator (g) | Acid Generator Used in Combination | (B) Resin (g) | Basic Compound (g) | Surfactant (g) | Solvent (mass ratio) | Sensitivity (mJ/cm$^2$) |
|---|---|---|---|---|---|---|---|
| Example | | | | | | | |
| Ar1 | A-8 (0.3) | | 1 (10) | DIA (0.03) | W-4 (0.01) | B1/C1 = 70/30 | 21.5 |
| Ar2 | A-1 (0.2) | z43 (0.1) | 4 (10) | TPA (0.03) | W-2 (0.02) | B1/B3 = 40/60 | 25.0 |
| Ar3 | A-4 (0.1) | z6 (0.2) | 6 (10) | HAP (0.02) | W-1 (0.01) | B1/C1 = 50/50 | 20.8 |
| Ar4 | A-8 (0.2) | z8 (0.1) | 6 (10) | TPSA (0.05) | W-4 (0.01) | B1/C1 = 60/40 | 18.8 |
| Ar5 | A-9 (0.25) | z12 (0.05) | 7 (10) | PEA (0.01) | W-4 (0.01) | B1/C1 = 60/40 | 21.3 |
| Ar6 | A-1 (0.1) A-22 (0.1) | z36 (0.1) | 7 (10) | DIA (0.02) PEA (0.02) | W-4 (0.01) | B1/B3 = 60/40 | 23.5 |
| Ar7 | A-28 (0.2) | z40 (0.1) | 15 (10) | TMEA (0.03) | W-3 (0.03) | B1/C2 = 80/20 | 26.1 |
| Ar8 | A-31 (0.15) | z41 (0.15) | 16 (10) | TBAH (0.04) | W-1 (0.005) | B2/C1 = 80/20 | 24.2 |
| Ar9 | A-34 (0.25) | z42 (0.05) | 17 (10) | HEP (0.03) | W-3 (0.02) | B3/C1 = 70/30 | 25.5 |
| Ar10 | A-40 (0.2) | z14 (0.1) | 24 (10) | TPSA (0.05) | W-3 (0.01) | B1/B3 = 60/40 | 24.6 |
| Ar11 | A-45 (0.1) | z25 (0.2) | 25 (10) | DCMA (0.03) | W-4 (0.01) | B1/B3 = 60/40 | 25.3 |
| Ar12 | A-16 (0.2) | z55 (0.1) | 28 (10) | DIA (0.03) | W-4 (0.01) | B1/C1 = 60/40 | 26.5 |
| Ar13 | A-45 (0.2) | z58 (0.1) | 29 (10) | PEA (0.04) | W-2 (0.02) | B1/B3 = 60/40 | 23.3 |
| Ar14 | A-39 (0.2) | z57 (0.1) | 30 (10) | PEA (0.04) | W-4 (0.01) | B1/B3 = 60/40 | 21.2 |
| Ar15 | A-52 (0.1) | z14 (0.2) | 31 (10) | DIA (0.03) | W-2 (0.02) | B1/B3 = 60/40 | 24.9 |
| Ar16 | A-12 (0.15) | z14 (0.15) | 6 (10) | DIA (0.03) | W-2 (0.01) | B1/B3 = 60/40 | 20.7 |
| Ar17 | A-26 (0.15) | z50 (0.15) | 7 (10) | DIA (0.02) | W-4 (0.01) | B1/B3 = 60/40 | 23.4 |
| Ar18 | A-1 (0.28) | z4 (0.02) | 28 (10) | PEA (0.02) | W-4 (0.01) | B1/C1 = 60/40 | 26.6 |
| Ar19 | A-25 (0.1) | z6 (0.1) z1 (0.1) | 28 (5) 20 (5) | DIA (0.02) DCMA (0.02) | W-4 (0.01) | B1/B3 = 60/40 | 27.1 |
| Ar20 | A-37 (0.2) A-51 (0.05) | z14 (0.05) | 4 (5) 7 (5) | TPA (0.02) PEA (0.02) | W-4 (0.01) | B1/C1 = 60/40 | 24.6 |
| Ar21 | A-8 (0.2) | z5 (0.05) z6 (0.05) | 28 (5) 11 (5) | DIA (0.02) TMEA (0.02) | W-4 (0.01) | B1/C1 = 60/40 | 22.6 |
| Ar22 | A-8 (0.1) | z38 (0.1) z44 (0.1) | 28 (5) 2 (5) | TPSA (0.02) PEA (0.02) | W-4 (0.01) | B1/B4 = 95/5 | 21.9 |
| Comparative Example | | | | | | | |
| Ar1 | PAG-A (0.3) | — | (1 (10) | DIA (0.03) | W-4 (0.01) | B1/C1 = 70/30 | 30.2 |
| Ar2 | PAG-B (0.3) | — | 1 (10) (ArF, positive) | DIA (0.03) | W-4 (0.01) | B1/C1 = 70/30 | 28.1 |
| Example | | | | | | | |
| Ar23 | A-69 (0.3) | | 1 (10) | TPA (0.03) | W-1 (0.01) | B1/C1 = 60/40 | 21.2 |
| Ar24 | A-78 (0.2) | z43 (0.1) | 4 (10) | TPA (0.03) | W-2 (0.02) | B1/C2 = 80/20 | 22.3 |
| Ar25 | A-84 (0.1) | z6 (0.2) | 6 (10) | HAP (0.02) | W-1 (0.01) | B2/C1 = 80/20 | 18.5 |
| Ar26 | A-103 (0.2) | z8 (0.1) | 6 (10) | TPSA (0.05) | W-4 (0.01) | B1/C1 = 70/30 | 19.6 |
| Ar27 | A'7 (0.25) | z12 (0.05) | 7 (10) | PEA (0.01) | W-4 (0.01) | B1/B3 = 40/60 | 19.9 |
| Ar28 | A'21 (0.2) | z40 (0.1) | 15 (10) | TMEA (0.03) | W-3 (0.03) | B1/C1 = 50/50 | 21.3 |
| Ar29 | A'28 (0.15) | z41 (0.15) | 16 (10) | TBAH (0.04) | W-1 (0.005) | B1/C1 = 60/40 | 19.6 |
| Ar30 | A-107 (0.3) | Z55 (0.1) | 1 (10) | TPSA (0.05) | W-1 (0.01) | B1/C1 = 60/40 | 19.5 |
| Ar31 | A-111 (0.2) | Z58 (0.1) | 4 (10) | DCMA (0.03) | W-2 (0.02) | B1/C2 = 80/20 | 19.8 |
| Ar32 | A-117 (0.1) | Z57 (0.1) | 6 (10) | DIA (0.03) | W-1 (0.01) | B2/C1 = 80/20 | 18.7 |
| Ar33 | A-119 (0.2) | z14 (0.2) | 6 (10) | PEA (0.04) | W-4 (0.01) | B1/C1 = 70/30 | 19.9 |

Abbreviations common in Tables 1, 2, 3, 5 and 6 are described together below.

[Acid Generator]

PAG-A: triphenylsulfonium nonafluorobutanesulfonate

PAG-B:

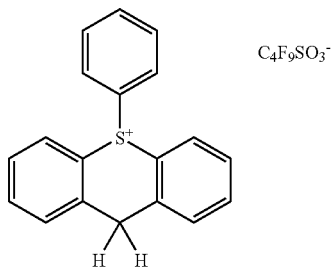

[Basic Compound]

TPI: 2,4,5-triphenylimidazole, TPSA: triphenylsulfonium acetate, HEP: N-hydroxyethylpiperidine, DIA: 2,6-diisopropylaniline, DCMA: dicyclohexylmethylamine, TPA: tripentylamine, HAP: hydroxyantipyrine, TBAH: tetrabutylammonium hydroxide, TMEA: tris(methoxyethoxyethyl)amine, PEN: N-phenyldiethanolamine.

[Surfactant]

W-1: Megafac F176 (produced by Dainippon Ink & Chemicals, Inc.) (fluorine-containing), W-2: Megafac R08 (produced by Dainippon Ink & Chemicals, Inc.) (fluorine- and silicon-containing), W-3: polysiloxane polymer KP-341 (produced by Shin-Etsu Chemical Co., Ltd.) (silicon-containing), W-4: Troysol S-366 (produced by Troy Chemical).

[Solvent]

B1: propylene glycol methyl ether acetate, B2: 2-heptanone, B3: cyclohexanone, B4: γ-butyrolactone, B5: methyl 2-methoxy propionate, C1: propylene glycol methyl ether, C2: ethyl lactate.

As apparent from the results in Tale 1, the photosensitive composition of the present invention exhibits excellent sensitivity at the ArF exposure.

Examples Si-1 to Si-9 and Comparative Examples si-1 and si-2

(1) Formation of Lower Resist Layer

FHi-028DD Resist (resist for i-line, produced by Fujifilm Olin Co., Ltd.) was coated on a 6-inch silicon wafer by using a spin coater, Mark 8, manufactured by Tokyo Electron Ltd. and then baked at 90° C. for 90 seconds to obtain a uniform film having a thickness of 0.55 μm.

This film was further heated at 200° C. for 3 minutes to form a lower resist layer having a thickness of 0.40 μm.

(2) Formation of Upper Resist Layer

The components shown in Table 2 below were dissolved in a solvent to prepare a solution having a solid content concentration of 11 mass %, and this solution was microfiltered through a membrane filter having a pore size of 0.1 μm to prepare an upper resist composition.

The upper resist composition prepared was coated on the lower resist layer in the same manner and heated at 130° C. for 90 seconds to form an upper resist layer having a thickness of 0.20 μm.

Resins (SI-1) to (SI-5) in Table 2 are shown below.

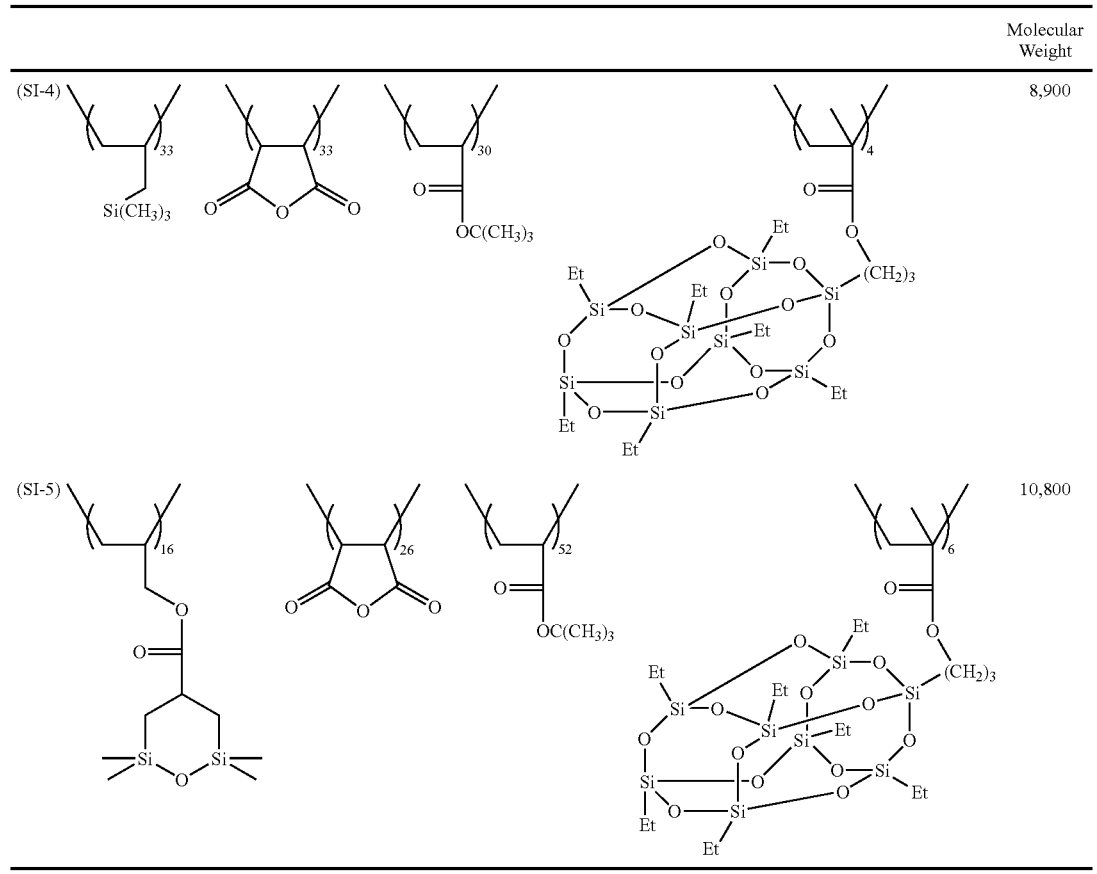

(3) Evaluation of Resist

The thus-obtained wafer was exposed by an ArF excimer stepper 9300 (manufactured by ISI) having mounted thereon a resolution mask, while changing the exposure amount.

Subsequently, the wafer was heated at 120° C. for 90 seconds, developed with a tetrahydroammonium hydroxide developer (2.38 mass %) for 60 seconds, rinsed with distilled water and dried to obtain an upper layer pattern.

(Sensitivity)

The sensitivity was expressed by an exposure amount necessary for reproducing a line-and-space (1:1) pattern having a line width of 130 nm.

The results obtained are shown in Table 2.

TABLE 2

|  | (A) Acid Generator (g) | Acid Generator Used in Combination | (B) Resin (g) | Basic Compound (g) | Surfactant (g) | Solvent (mass ratio) | Sensitivity (mJ/cm$^2$) |
|---|---|---|---|---|---|---|---|
| Example |  |  |  |  |  |  |  |
| Si-1 | A-8 (0.6) | — | SI-1 | DIA (0.03) | W-4 (0.01) | B1 = 100 | 22.6 |
| Si-2 | A-4 (0.4) | z14 (0.2) | SI-2 | TPA (0.03) | W-2 (0.02) | B1/B5 = 40/60 | 23.4 |
| Si-3 | A-37 (0.2) | z6 (0.4) | SI-3 | HAP (0.02) | W-1 (0.01) | B1/C1 = 60/40 | 25.5 |
| Si-4 | A-40 (0.5) | z8 (0.1) | SI-4 | DIA (0.03) | W-4 (0.01) | B1/C1 = 60/40 | 24.4 |
| Si-5 | A-41 (0.55) | z12 (0.05) | SI-5 | PEA (0.01) | W-4 (0.01) | B1/B5 = 60/40 | 23.1 |
| Comparative Example |  |  |  |  |  |  |  |
| si-1 | PAG-A (0.6) | — | SI-1 | DIA (0.03) | W-4 (0.01) | B1 = 100 | 31.3 |
| si-2 | PAG-B (0.6) | — | SI-1 (containing silicon) | DIA (0.03) | W-4 (0.01) | B1 = 100 | 29.5 |
| Example |  |  |  |  |  |  |  |
| Si-6 | A-67 (0.6) |  | SI-1 | DIA (0.03) | W-4 (0.01) | B1 = 100 | 23.5 |
| Si-7 | A-84 (0.4) | z14 (0.2) | SI-2 | TPA (0.03) | W-2 (0.02) | B1/B5 = 40/60 | 21.6 |

TABLE 2-continued

| | (A) Acid Generator (g) | Acid Generator Used in Combination | (B) Resin (g) | Basic Compound (g) | Surfactant (g) | Solvent (mass ratio) | Sensitivity (mJ/cm$^2$) |
|---|---|---|---|---|---|---|---|
| Si-8 | A-109 (0.6) | Z12 (0.1) | SI-1 | PEA (0.04) | W-4 (0.01) | B1 = 100 | 22.3 |
| Si-9 | A-117 (0.4) | Z35 (0.2) | SI-2 | DIA (0.03) | W-2 (0.02) | B1/B5 = 40/60 | 20.7 |

As apparent from the results in Table 2, the photosensitive composition of the present invention exhibits excellent sensitivity even when used as a two-layer resist.

Examples KrP-1 to KrP-31 and Comparative Examples krp-1 and krp-2

<Preparation of Resist>

The components shown in Table 4 below were dissolved in a solvent, and the resulting solution was filtered through a 0.1-µm polytetrafluoroethylene filter to prepare a positive resist solution having a solid content concentration of 14 mass %.

The positive resist solutions prepared were evaluated by the following method, and the results obtained are shown in Table 4.

The molar ratio and average molecular weight of each of Resins (R-2) to (R-27) in Table 4 are shown in Table 3 below. The repeating units constituting each of Resins (R-2) to (R-27) are those shown above.

TABLE 3

| Resin | Molar Ratio of Repeating Units (in the order from left) | Weight Average Molecular Weight |
|---|---|---|
| R-2 | 60/40 | 12000 |
| R-7 | 60/30/10 | 18000 |
| R-8 | 60/20/20 | 12000 |
| R-9 | 10/50/40 | 13000 |
| R-14 | 75/25 | 12000 |
| R-17 | 10/70/20 | 15000 |
| R-19 | 10/70/20 | 11000 |
| R-22 | 70/30 | 12000 |
| R-23 | 10/50/30 | 8000 |
| R-24 | 50/20/30 | 16000 |
| R-25 | 10/70/20 | 13000 |
| R-27 | 70/10/20 | 12000 |
| R-29 | 44/7/21/28 | 8800 |
| R-30 | 47/3/33/17 | 8400 |
| R-31 | 45/55 | 12700 |

TABLE 3-continued

| Resin | Molar Ratio of Repeating Units (in the order from left) | Weight Average Molecular Weight |
|---|---|---|
| R-34 | 70/30 | 9100 |
| R-38 | 75/25 | 11000 |
| R-41 | 10/60/30 | 8600 |
| R-48 | 70/30 | 12000 |
| R-50 | 70/10/20 | 13000 |
| R-54 | 42/20/15/23 | 9500 |
| R-55 | 45/13/25/17 | 10000 |
| R-58 | 73/27 | 10500 |
| R-65 | 25/64/11 | 12000 |
| R-70 | 76/24 | 8800 |
| R-74 | 80/5/15 | 15000 |
| R-79 | 10/78/12 | 8700 |
| R-82 | 81/15/4 | 9600 |
| R-86 | 76/20/4 | 11000 |

<Evaluation of Resist>

On a silicon substrate treated with hexamethyldisilazane, the positive resist solution prepared was uniformly coated by a spin coater and dried under heating on a hot plate at 120° C. for 90 seconds to form a resist film having a thickness of 0.4 µm.

The obtained resist film was exposed by using a KrF excimer laser stepper (NA=0.63) through a mask for a line-and-space pattern and immediately after the exposure, heated on a hot plate at 110° C. for 90 seconds. Thereafter, the resist film was developed with an aqueous 2.38 mass % tetramethylammonium hydroxide solution at 23° C. for 60 seconds, rinsed with pure water for 30 seconds and then dried to form a line pattern. The pattern falling and line edge roughness of the line pattern were evaluated.

Sensitivity:

The sensitivity was expressed by an exposure amount necessary for reproducing a line-and-space (1:1) pattern having a line width of 150 nm.

The evaluation results are shown in Table 4.

TABLE 4

| | (A) Acid Generator (g) | Acid Generator Used in Combination | (B) Resin (g) | Basic Compound (g) | Surfactant (g) | Solvent (mass ratio) | Sensitivity (mJ/cm$^2$) |
|---|---|---|---|---|---|---|---|
| Example | | | | | | | |
| KrP-1 | A-7 (0.3) | — | R-7 (10) | TPI (0.03) | W-4 (0.01) | B1/C1 = 70/30 | 21.8 |
| KrP-2 | A-7 (0.2) | z31 (0.1) | R-8 (10) | TPSA (0.03) | W-2 (0.02) | B1/B5 = 40/60 | 18.3 |
| KrP-3 | A-41 (0.15) | z6 (0.2) | R-9 (10) | HAP (0.02) | W-1 (0.01) | B1/C1 = 50/50 | 20.1 |
| KrP-4 | A-35 (0.2) | z57 (0.1) | R-14 (10) | DCMA (0.03) | W-4 (0.01) | B1/C1 = 60/40 | 19.9 |
| KrP-5 | A-50 (0.25) | z12 (0.05) | R-17 (10) | PEA (0.01) | W-4 (0.01) | B1/C1 = 60/40 | 24.0 |
| KrP-6 | A-7 (0.1) A-2 (0.1) | z4 (0.1) | R-19 (5) R-27 (5) | DIA (0.02) PEA (0.02) | W-4 (0.01) | B1/B5 = 60/40 | 23.5 |

TABLE 4-continued

| | (A) Acid Generator (g) | Acid Generator Used in Combination | (B) Resin (g) | Basic Compound (g) | Surfactant (g) | Solvent (mass ratio) | Sensitivity (mJ/cm$^2$) |
|---|---|---|---|---|---|---|---|
| KrP-7 | A-42 (0.2) | z40 (0.1) | R-23 (10) | TMEA (0.03) | W-3 (0.03) | B1/C2 = 80/20 | 21.5 |
| KrP-8 | A-60 (0.15) | z31 (0.3) | R-24 (10) | TBAH (0.04) | W-1 (0.005) | B2/C1 = 80/20 | 23.4 |
| KrP-9 | A-10 (0.5) | z32 (0.3) | R-25 (5) R-2 (5) | HEP (0.03) | W-3 (0.02) | B5/C1 = 70/30 | 20.6 |
| KrP-10 | A-1 (0.2) | z55 (0.1) | R-27 (5) R-22 (5) | TPSA (0.05) | W-3 (0.01) | B1/B5 = 60/40 | 22.1 |
| KrP-11 | A-38 (0.2) | z20 (0.1) | R-29 (10) | TPI (0.03) | W-1 (0.01) | B1/B5 = 60/40 | 21.5 |
| KrP-12 | A-1 (0.2) | z45 (0.1) | R-30 (10) | TPSA (0.03) | W-1 (0.01) | B1/C1 = 50/50 | 23.3 |
| KrP-13 | A-7 (0.2) | z5 (0.1) | R-31 (10) | HAP (0.02) | W-1 (0.01) | B1/C1 = 60/40 | 21.9 |
| Comparative Example | | | | | | | |
| krp-1 | PAG-A (0.3) | — | R-7 (10) | TPI (0.03) | W-4 (0.01) | B1/C1 = 70/30 | 29.8 |
| krp-2 | PAG-B (0.3) | — | R-7 (10) (KrF, positive) | TPI (0.03) | W-4 (0.01) | B1/C1 = 70/30 | 27.2 |
| Example | | | | | | | |
| KrP-14 | A-66 (0.3) | | R-34 (10) | TPI (0.03) | W-4 (0.01) | B1/C1 = 70/30 | 22.5 |
| KrP-15 | A-78 (0.2) | z31 (0.1) | R-38 (10) | TPSA (0.03) | W-2 (0.02) | B1/B5 = 40/60 | 18.6 |
| KrP-16 | A-86 (0.15) | z6 (0.15) | R-41 (10) | HAP (0.02) | W-1 (0.01) | B1/C1 = 50/500 | 19.2 |
| KrP-17 | A-72 (0.2) | z57 (0.1) | R-48 (10) | DCMA (0.03) | W-4 (0.01) | B1/C1 = 60/40 | 17.5 |
| KrP-18 | A-65 (0.3) | | R-50 (10) | PEA (0.01) | W-4 (0.01) | B1/C1 = 60/40 | 17.3 |
| KrP-19 | A-102 (0.2) | z40 (0.1) | R-54 (10) | TMEA (0.03) | W-4 (0.01) | B1/C2 = 80/20 | 20.6 |
| KrP-20 | A-105 (0.15) | z31 (0.15) | R-55 (10) | TBAH (0.04) | W-3 (0.03) | B2/C1 = 80/20 | 19.3 |
| KrP-21 | A'-24 (0.15) | z6 (0.15) | R-58 (10) | DCMA (0.03) | W-1 (0.005) | B1/C1 = 50/50 | 20.1 |
| KrP-22 | A-93 (0.2) | z57 (0.1) | R-65 (10) | PEA (0.01) | W-2 (0.02) | B1/C1 = 70/30 | 21.6 |
| KrP-23 | A-90 (0.2) | z20 (0.1) | R-70 (10) | TMEA (0.03) | W-1 (0.01) | B1/B5 = 40/60 | 21.5 |
| KrP-24 | A'-22 (0.15) | z31 (0.15) | R-74 (10) | TPSA (0.03) | W-4 (0.01) | B1/C1 = 50/50 | 19.6 |
| KrP-25 | A-66 (0.05) | z32 (0.25) | R-79 (10) | TPI (0.03) | W-1 (0.01) | B1/C1 = 60/40 | 18.5 |
| KrP-26 | A-69 (0.2) | z45 (0.1) | R-82 (10) | TPSA (0.03) | W-4 (0.01) | B1/C1 = 60/40 | 18.7 |
| KrP-27 | A-73 (0.2) | z5 (0.1) | R-86 (10) | HAP (0.02) | W-1 (0.01) | B1/C1 = 60/40 | 17.5 |
| KrP-28 | A-106 (0.3) | z39 (0.0) | R-34 (10) | TPI (0.03) | W-4 (0.01) | B1/C1 = 70/30 | 18.6 |
| KrP-29 | A-113 (0.2) | Z45 (0.1) | R-38 (10) | TPSA (0.03) | W-2 (0.02) | B1/B5 = 40/60 | 17.9 |
| KrP-30 | A-116 (0.15) | z5 (0.15) | R-41 (10) | HAP (0.02) | W-1 (0.01) | B1/C1 = 50/50 | 16.7 |
| KrP-31 | A-118 (0.2) | Z19 (0.1) | R-48 (10) | DGMA (0.03) | W-4 (0.01) | B1/C1 = 60/40 | 17.6 |

As apparent from the results in Table 4, the photosensitive composition of the present invention exhibits excellent sensitivity even when used as a positive resist composition for exposure with a KrF excimer laser.

Examples KrN-1 to KrN-21 and Comparative Examples krn-1 and krn-2

<Preparation of Resist>

The components shown in Table 5 below were dissolved in a solvent, and the resulting solution was filtered through a 0.1-μm polytetrafluoroethylene filter to prepare a negative resist solution having a solid content concentration of 14 mass %.

The prepared negative resist solutions were evaluated in the same manner as, for example, in Examples KrP-1 to KrP-13. The results obtained are shown in Table 5.

The structure, molecular weight and molecular weight distribution of each of the alkali-soluble resins in Table 5 are shown below.

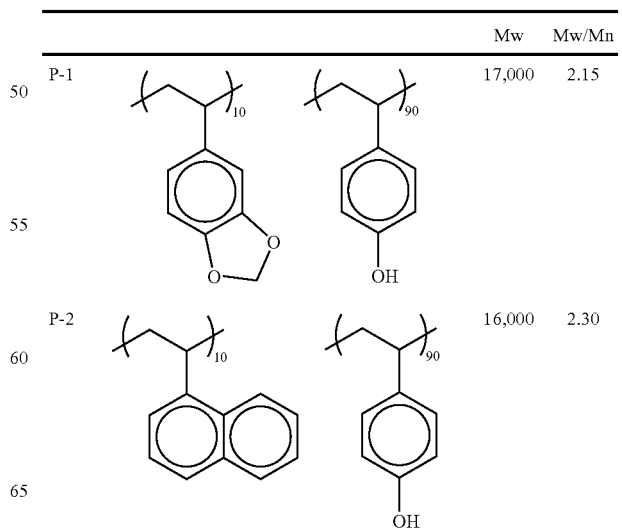

-continued
| | | Mw | Mw/Mn |
|---|---|---|---|
| P-3 | 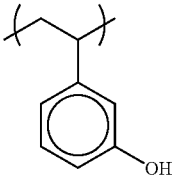 | 19,000 | 2.2 |
| P-4 | 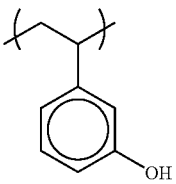 | 12,000 | 1.2 |
-continued
| | | Mw | Mw/Mn |
|---|---|---|---|
| P-5 | 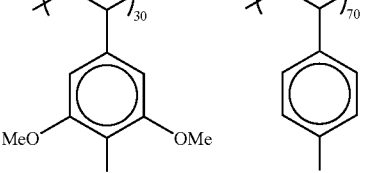 | 21,000 | 2.1 |
| P-6 | 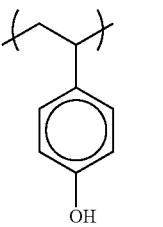 | 6,000 | 1.2 |
VP-5000 produced by Nippon Soda Co., Ltd.
The structures of the crosslinking agents in Table 5 are shown below.
TABLE 5
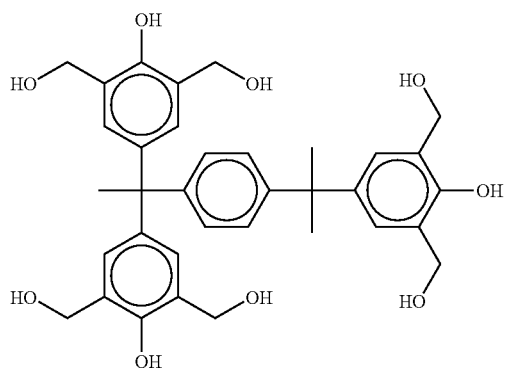
CL-1
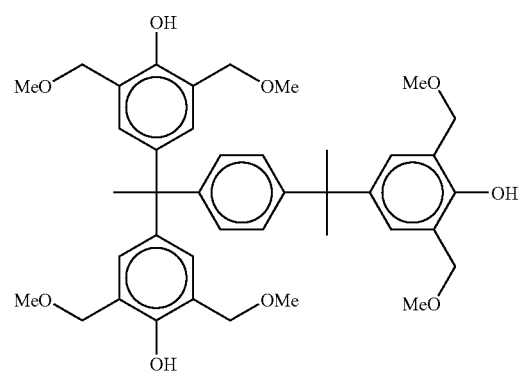
CL-2
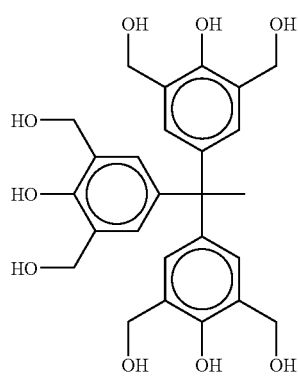
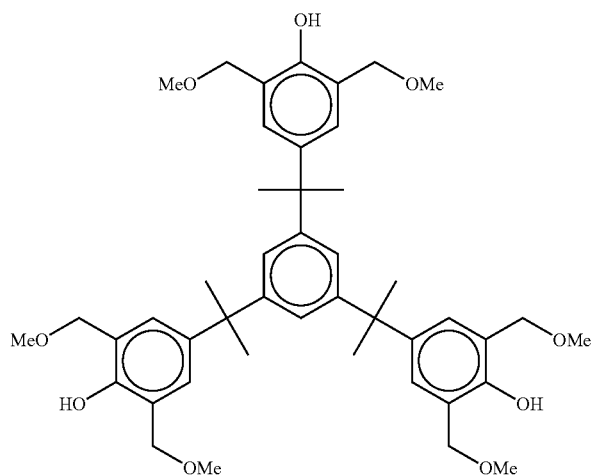

CL-3

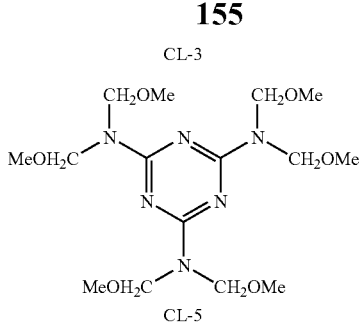

CL-4

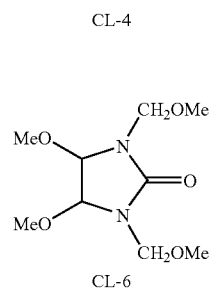

CL-5

CL-6

(KrF, negative)

| | (A) Acid Generator (g) | Acid Generator Used in Combination | (B) Resin (g) | Crosslinking Agent (g) | Basic Compound (g) | Surfactant (g) | Solvent | Sensitivity (mJ/cm$^2$) |
|---|---|---|---|---|---|---|---|---|
| Example | | | | | | | | |
| KrN-1 | A-7 (0.3) | — | P-1 (10) | CL-1 (2) | TPI (0.03) | W-4 (0.01) | B1/C1 = 70/30 | 23.5 |
| KrN-2 | A-7 (0.2) | z31 (0.1) | P-2 (10) | CL-2 (3) | TPSA (0.03) | W-2 (0.02) | B1/B5 = 40/60 | 20.3 |
| KrN-3 | A-39 (0.15) | z6 (0.2) | P-3 (10) | CL-3 (2.5) | HAP (0.02) | W-1 (0.01) | B1/C1 = 50/50 | 22.3 |
| KrN-4 | A-35 (0.2) | z57 (0.1) | P-4 (10) | CL-4 (3) | DCMA (0.03) | W-4 (0.01) | B1/C1 = 60/40 | 21.5 |
| KrN-5 | A-61 (0.25) | z12 (0.05) | P-5 (10) | CL-5 (1.5) | PEA (0.01) | W-4 (0.01) | B1/C1 = 60/40 | 26.1 |
| KrN-6 | A-7 (0.1) A-2 (0.1) | z4 (0.1) | P-2 (5) P-6 (5) | CL-1 (2) CL-5 (2) | DIA (0.02) PEA (0.02) | W-4 (0.01) | B1/B5 = 60/40 | 23.3 |
| KrN-7 | A-34 (0.2) | z40 (0.1) | P-1 (10) | CL-6 (2) | TMEA (0.03) | W-3 (0.03) | B1/C2 = 80/20 | 25.6 |
| KrN-8 | A-60 (0.15) | z31 (0.15) | P-6 (10) | CL-2 (3) | TBAH (0.04) | W-1 (0.005) | B2/C1 = 80/20 | 25.2 |
| KrN-9 | A-29 (0.5) | z32 (0.25) | P-3 (10) | CL-1 (2.5) | HEP (0.03) | W-3 (0.02) | B5/C1 = 70/30 | 22.3 |
| KrN-10 | A-1 (0.2) | z55 (0.1) | P-4 (10) | CL-4 (3) | TPSA (0.05) | W-3 (0.03) | B1/B5 = 60/40 | 24.3 |
| KrN-11 | A-72 (0.2) | z57 (0.1) | P-1 (10) | CL-4 (3) | TPI (0.03) | W-4 (0.01) | B1/C1 = 70/30 | 23.2 |
| KrN-12 | A-65 (0.3) | — | P-2 (10) | CL-5 (2) | TPSA (0.03) | W-2 (0.02) | B1/B5 = 40/60 | 23.0 |
| KrN-13 | A-102 (0.2) | z40 (0.1) | P-3 (10) | CL-1 (3) | HAP (0.02) | W-1 (0.01) | B1/C1 = 50/50 | 26.9 |
| KrN-14 | A-105 (0.15) | z31 (0.15) | P-4 (10) | CL-5 (2) | DCMA (0.03) | W-4 (0.01) | B1/C1 = 60/40 | 25.4 |
| KrN-15 | A-24 (0.15) | z6 (0.15) | P-5 (10) | CL-1 (2) | PEA (0.01) | W-4 (0.01) | B1/C1 = 60/40 | 26.3 |
| KrN-16 | A-93 (0.2) | z57 (0.1) | P-1 (10) | CL-2 (4) | TMEA (0.03) | W-3 (0.03) | B1/C2 = 80/20 | 28.1 |
| KrN-17 | A-90 (0.2) | z20 (0.1) | P-6 (10) | CL-4 (3) | TBAH (0.04) | W-1 (0.005) | B2/C1 = 80/20 | 28.0 |
| Comparative Example | | | | | | | | |
| krn 1 | PAG-A (0.3) | — | P-1 (10) | CL-1 (2) | TPI (0.03) | W-4 (0.01) | B1/C1 = 70/30 | 35.8 |
| krn 2 | PAG-B (0.3) | — | P-1 (10) | CL-1 (2) | TPI (0.03) | W-4 (0.01) | B1/C1 = 70/30 | 31.2 |
| KrN-18 | A-106 (0.3) | Z57 (0.1) | P-1 (10) | CL-1 (2) | TPI (0.03) | W-4 (0.01) | B1/C1 = 70/30 | 22.2 |
| KrN-19 | A-113 (0.2) | — | P-2 (10) | CL-2 (3) | TPSA (0.03) | W-2 (0.02) | B1/B5 = 40/60 | 23.3 |
| KrN-20 | A-116 (0.15) | Z40 (0.1) | P-3 (10) | CL-3 (2.5) | HAP (0.02) | W-1 (0.01) | B1/C1 = 50/50 | 20.9 |
| KrN-21 | A-118 (0.2) | Z31 (0.15) | P-4 (10) | CL-4 (3) | DCMA (0.03) | W-4 (0.01) | B1/C1 = 60/40 | 24.3 |

As apparent from the results in Table 5, the photosensitive composition of the present invention is assured of less pattern falling, small line edge roughness and excellent pattern profile even when used as a negative resist composition for exposure with a KrF excimer laser.

Examples EBP-1 to EBP-31 and Comparative Examples ebp-1 and ebp-2

<Preparation of Resist>

The components shown in Table 4 were dissolved in a solvent, and the resulting solution was filtered through a 0.1-μm polytetrafluoroethylene filter to prepare a positive resist solution having a solid content concentration of 12 mass %.

The positive resist solution prepared was evaluated by the following method, and the results obtained are shown in Table 6.

<Evaluation of Resist>

On a silicon substrate treated with hexamethyldisilazane, the positive resist solution prepared was uniformly coated by a spin coater and dried under heating on a hot plate at 120° C. for 60 seconds to form a resist film having a thickness of 0.3 μm.

The resist film obtained was irradiated by an electron beam projection lithography apparatus manufactured by Nikon Corp. (accelerating voltage: 100 KeV) and immediately after the irradiation, heated on a hot plate at 110° C. for 90 seconds. Thereafter, the resist film was developed with an aqueous tetramethylammonium hydroxide solution having a concentration of 2.38 mass % at 23° C. for 60 seconds, rinsed with pure water for 30 seconds and then dried to form a line-and-space pattern.

Sensitivity:

The sensitivity was expressed by an irradiation dose necessary for reproducing the 100-nm line and space (1:1) of the mask pattern.

Outgas:

The resist film was irradiated at a dose of 10 μC/cm$^2$, and the film thickness after irradiation based on the film thickness before irradiation was measured and evaluated as the amount of outgas.

TABLE 6

| | Sensitivity (µC/cm²) | Outgas (evaluation of film thickness) |
|---|---|---|
| Example | | |
| EBP-1 | 1.9 | 99.5% |
| EBP-2 | 1.7 | 98.7% |
| EBP-3 | 2.2 | 98.6% |
| EBP-4 | 2.4 | 99.0% |
| EBP-5 | 2.6 | 97.6% |
| EBP-6 | 2.5 | 98.2% |
| EBP-7 | 2.6 | 99.4% |
| EBP-8 | 2.6 | 98.5% |
| EBP-9 | 2.4 | 97.9% |
| EBP-10 | 2.8 | 98.8% |
| EBP-11 | 1.8 | 99.1% |
| EBP-12 | 2.4 | 98.6% |
| EBP-13 | 1.9 | 99.4% |
| Comparative Example | | |
| ebp-1 | 4.1 | 95.3% |
| ebp-2 | 3.5 | 97.3% |
| (electron beam, negative) | | |
| Example | | |
| EBP-14 | 2.4 | 99.1% |
| EBP-15 | 1.8 | 98.2% |
| EBP-16 | 1.9 | 97.4% |
| EBP-17 | 1.6 | 98.7% |
| EBP-18 | 1.6 | 98.3% |
| EBP-19 | 2.1 | 98.2% |
| EBP-20 | 1.9 | 99.4% |
| EBP-21 | 2.0 | 98.5% |
| EBP-22 | 2.2 | 99.5% |
| EBP-23 | 2.2 | 98.7% |
| EBP-24 | 1.9 | 98.6% |
| EBP-25 | 1.8 | 99.0% |
| EBP-26 | 1.8 | 97.6% |
| EBP-27 | 1.6 | 98.2% |
| EBP-28 | 1.8 | 99.1% |
| EBP-29 | 1.7 | 99.3% |
| EBP-30 | 1.6 | 98.9% |
| EBP-31 | 1.8 | 99.0% |

As apparent from the results in Table 6, the photosensitive composition of the present invention is excellent with high sensitivity and low outgas even when used as a positive resist composition for electron beam irradiation.

Examples EBN-1 to EBN-21 and Comparative Examples ebn-1 and ebn-2

<Preparation of Resist>

The components shown in Table 5 were dissolved in a solvent, and the resulting solution was filtered through a 0.1-µm polytetrafluoroethylene filter to prepare a negative resist-solution having a solid content concentration of 12 mass %.

The negative resist solutions prepared were evaluated by the following method, and the results obtained are shown in Table 7.

<Evaluation of Resist>

On a silicon substrate treated with hexamethyldisilazane, the negative resist solution prepared was uniformly coated by a spin coater and dried under heating on a hot plate at 120° C. for 60 seconds to form a resist film having a thickness of 0.3 µm.

The resist film obtained was irradiated by an electron beam projection lithography apparatus manufactured by Nikon Corp. (accelerating voltage: 100 KeV) and immediately after the irradiation, heated on a hot plate at 110° C. for 90 seconds. Thereafter, the resist film was developed with an aqueous tetramethylammonium hydroxide solution having a concentration of 2.38 mass % at 23° C. for 60 seconds, rinsed with pure water for 30 seconds and then dried to form a line-and-space pattern.

Sensitivity:

The sensitivity was expressed by an irradiation dose necessary for reproducing 100-nm line/150-nm space of the mask pattern.

Outgas:

The resist film was irradiated at a dose of 10 µC/cm², and the film thickness after irradiation when compared with the film thickness before irradiation was measured and evaluated as the amount of outgas.

TABLE 7

| | Sensitivity (µC/cm²) | Outgas (evaluation of film thickness) |
|---|---|---|
| Example | | |
| EBN-1 | 2.5 | 99.0% |
| EBN-2 | 2.2 | 98.8% |
| EBN-3 | 2.4 | 97.9% |
| EBN-4 | 2.5 | 98.1% |
| EBN-5 | 3.0 | 97.7% |
| EBN-6 | 2.9 | 98.5% |
| EBN-7 | 3.0 | 96.8% |
| EBN-8 | 3.1 | 97.8% |
| EBN-9 | 2.8 | 98.4% |
| EBN-10 | 3.3 | 97.2% |
| Comparative Example | | |
| ebn-1 | 4.8 | 94.6% |
| ebn-2 | 3.8 | 96.4% |
| (electron beam, negative) | | |
| Example | | |
| EBN-11 | 2.2 | 97.8% |
| EBN-12 | 2.2 | 98.4% |
| EBN-13 | 2.9 | 97.4% |
| EBN-14 | 2.6 | 98.7% |
| EBN-15 | 2.8 | 98.5% |
| EBN-16 | 3.1 | 98.7% |
| EBN-17 | 3.1 | 98.6% |
| EBN-18 | 2.1 | 98.9% |
| EBN-19 | 2.4 | 99.2% |
| EBN-20 | 2.0 | 99.0% |
| EBN-21 | 2.5 | 98.7% |

As apparent from the results in Table 7, the photosensitive composition of the present invention is excellent with high sensitivity and low outgas even when used as a negative resist composition for electron beam irradiation.

Examples EUVP-1 to EUVP-31 and Comparative Example euvp-1

Production and Evaluation of Pattern (EUV)

The components shown in Table 4 were dissolved in a solvent to prepare a solution having a solid content concentration of 5 mass %. This solution was filtered through a 0.1-µm Teflon (registered trademark) filter to obtain a positive resist solution. The resist film was formed to a thickness of 0.15 µm. The resist film obtained was planarly exposed with EUV light (wavelength: 13 nm) while changing the exposure amount in 0.5-mJ steps in the range from 0 to 10.0 mJ and baked at 100° C. for 90 seconds. Thereafter, the dissolution rate at each exposure amount was measured by using an aqueous 2.38% tetramethylammonium hydroxide (TMAH) solution, and a sensitivity curve was obtained from the measured values. The sensitivity was defined as the exposure amount when the dissolution rate of resist was saturated on the sensitivity curve. Separately, a resist film having a thickness of 0.3 μm was prepared, and the film thickness after exposure based on the film thickness before exposure of 5 mJ/m² was measured and evaluated as the amount of the outgas. The results obtained are shown in Table 8.

As seen from the results in Table 8, the resist composition of the present invention is excellent with high sensitivity and low outgas compared to the compositions of Comparative Examples in the characteristic evaluation by the exposure with EUV light.

TABLE 8

| | Sensitivity (mJ/cm²) | Outgas (evaluation of film thickness) |
|---|---|---|
| Example | | |
| EUVP-1 | 2.7 | 98.9% |
| EUVP-2 | 2.5 | 99.0% |
| EUVP-3 | 3.0 | 97.8% |
| EUVP-4 | 3.3 | 98.3% |
| EUVP-5 | 3.5 | 99.0% |
| EUVP-6 | 3.6 | 98.4% |
| EUVP-7 | 3.5 | 97.7% |
| EUVP-8 | 3.4 | 99.1% |
| EUVP-9 | 3.1 | 98.2% |
| EUVP-10 | 3.4 | 97.4% |
| EUVP-11 | 2.8 | 98.7% |
| EUVP-12 | 3.5 | 98.3% |
| EUVP-13 | 2.7 | 98.8% |
| Comparative Example | | |
| Euvp-1 | 5.5 | 95.5% |
| Euvp-2 | 4.8 | 97.2% |
| Example | | |
| EUVP-14 | 3.8 | 97.8% |
| EUVP-15 | 2.6 | 98.2% |
| EUVP-16 | 2.8 | 98.4% |
| EUVP-17 | 2.3 | 98.7% |
| EUVP-18 | 2.2 | 98.6% |
| EUVP-19 | 3.2 | 98.9% |
| EUVP-20 | 2.8 | 99.0% |
| EUVP-21 | 3.0 | 98.5% |
| EUVP-22 | 3.5 | 98.7% |
| EUVP-23 | 3.5 | 98.6% |
| EUVP-24 | 2.9 | 97.8% |
| EUVP-25 | 2.6 | 98.2% |
| EUVP-26 | 2.6 | 98.4% |
| EUVP-27 | 2.3 | 98.7% |
| EUVP-28 | 2.9 | 98.9% |
| EUVP-29 | 2.5 | 99.2% |
| EUVP-30 | 2.1 | 99.3% |
| EUVP-31 | 2.3 | 99.1% |

Examples EUVN-1 to EUVN-21 and Comparative Example euvn-1

Production and Evaluation of Pattern (EUV)

The components shown in Table 5 were dissolved in a solvent to prepare a solution having a solid content concentration of 5 mass %. This solution was filtered through a 0.1-μm Teflon (registered trademark) filter to obtain a negative resist solution. The resist film was formed to a thickness of 0.15 μm. The resist film obtained was planarly exposed with EUV light (wavelength: 13 nm) while changing the exposure amount in 0.5-mJ steps in the range from 0 to 10.0 mJ and baked at 100° C. for 90 seconds. Thereafter, the dissolution rate at each exposure amount was measured by using an aqueous 2.38% tetramethylammonium hydroxide (TMAH) solution, and a sensitivity curve was obtained from the measured values. The sensitivity was defined as the exposure amount when the dissolution rate of resist was saturated on the sensitivity curve. Separately, a resist film having a thickness of 0.3 μm was prepared, and the film thickness after exposure based on the film thickness before exposure of 5 mJ/m² was measured and evaluated as the amount of the outgas. The results obtained are shown in Table 9.

As seen from the results in Table 8, the resist composition of the present invention is excellent with high sensitivity and low outgas compared to the compositions of Comparative Examples in the characteristic evaluation by the exposure with EUV light.

TABLE 9

| | Sensitivity (mJ/cm²) | Outgas (evaluation of film thickness) |
|---|---|---|
| Example | | |
| EUVN-1 | 2.9 | 98.5% |
| EUVN-2 | 2.7 | 98.7% |
| EUVN-3 | 3.3 | 98.6% |
| EUVN-4 | 3.5 | 97.8% |
| EUVN-5 | 3.7 | 98.2% |
| EUVN-6 | 3.9 | 98.4% |
| EUVN-7 | 3.8 | 98.7% |
| EUVN-8 | 3.5 | 98.6% |
| EUVN-9 | 3.0 | 98.9% |
| EUVN-10 | 3.6 | 99.0% |
| Comparative Example | | |
| Euvn-1 | 6.0 | 94.4% |
| Euvn-1 | 4.7 | 96.4% |
| Example | | |
| EUVN-11 | 2.5 | 99.0% |
| EUVN-12 | 2.5 | 98.8% |
| EUVN-13 | 2.9 | 97.9% |
| EUVN-14 | 2.7 | 98.1% |
| EUVN-15 | 2.8 | 97.7% |
| EUVN-16 | 3.0 | 98.5% |
| EUVN-17 | 3.0 | 96.8% |
| EUVN-18 | 2.4 | 99.1% |
| EUVN-19 | 2.3 | 98.5% |
| EUVN-20 | 2.0 | 99.6% |
| EUVN-21 | 2.5 | 99.2% |

(Immersion Exposure)

<Preparation of Resist>

The components of each of Examples Ar1 to Ar22 shown in Table 1 were dissolved in a solvent to prepare a solution having a solid content concentration of 7 mass %, and this solution was filtered through a 0.1-μm polyethylene filter to prepare a positive resist solution. The positive resist solutions prepared were evaluated by the following methods <Evaluation of Resolution>

An organic antireflection film, ARC29A (produced by Nissan Chemical Industries, Ltd.), was coated on a silicon wafer and baked at 205° C. for 60 seconds to form a 78-nm antireflection film. On this film, the resist composition prepared was coated and baked at 120° C. for 60 seconds to form a 150-nm resist film. The thus-obtained wafer was subjected to two-beam interference exposure (wet exposure) by using pure water as the immersion solution. In the two-beam interference exposure (wet), as shown in FIG. 1, the wafer 10 with an antireflection film and a resist film was exposed through a prism 8 and an immersion solution (pure water) 9 by using a laser 1, a diaphragm 2, a shutter 3, three reflecting mirrors 4, 5 and 6, and a condenser lens 7. The wavelength of the laser 1 used was 193 nm, and a prism 8 of forming a 65-nm line-and-space pattern was used. Immediately after the exposure, the resist film was heated at 120° C. for 60 seconds, then developed with an aqueous tetramethylammonium hydroxide solution (2.38 mass %) for 60 seconds and after rinsing with pure water, spin-dried. The obtained resist pattern was observed by a scanning electron microscope (S-9260, manufactured by Hitachi Ltd.), as a result, a 65-nm line-and-space pattern was resolved.

In this way, the composition of the present invention exhibits a good image-forming capability even in the exposure method through an immersion solution.

This application is based on Japanese patent applications JP 2005-042328, filed on Feb. 18, 2005, and JP 2005-252611, filed on Aug. 31, 2005, the entire content of which is hereby incorporated by reference, the same as if set forth at length.

What is claimed is:

1. A resist composition comprising (A) a sulfonium salt represented by the following formula (I); and (B) a resin capable of decomposing under the action of an acid to increase the solubility in an alkali developer:

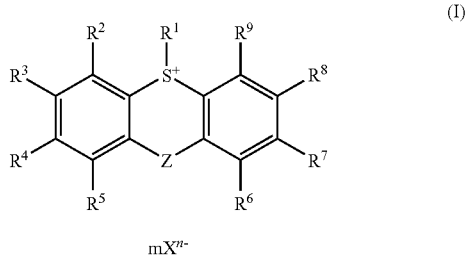

wherein $R^1$ represents an alkyl group or an aryl group, $R^2$ to $R^9$ each independently represents a hydrogen atom or a substituent and may combine with each other to form a ring, Z represents an electron-withdrawing divalent linking group, $X^{n-}$ represents an n-valent organic anion, n represents an integer of 1 to 3, and m represents the number of anions necessary for neutralizing the electric charge.

2. A resist composition capable of changing its properties by undergoing a reaction upon irradiation with X-rays, electron beams or EUV, comprising the resist composition as claimed in claim 1.

3. The resist composition as claimed in claim 1, wherein the resin (B) has a hydroxystyrene structural unit.

4. The resist composition as claimed in claim 3, which further comprises (C) a dissolution inhibiting compound capable of decomposing under the action of an acid to increase the solubility in an alkali developer and having a molecular weight of 3,000 or less.

5. The resist composition as claimed in claim 3, which further comprises (F) a basic compound and/or (G) a fluorine-and/or silicon-containing surfactant.

6. The resist composition as claimed in claim 3, wherein the resin (B) comprises: at least one repeating unit selected from 2-alkyl-2-adamantyl(meth)acrylate and dialkyl(1-adainantyl)methyl(meth)acrylate; and at least one repeating unit having a hydroxystyrene structure.

7. The resist composition as claimed in claim 1, wherein the resin (B) contains a repeating unit having a monocyclic or polycyclic hydrocarbon structure.

8. The resist composition as claimed in claim 7, wherein the resin (B) comprises: at least one repeating unit selected from 2-alkyl-2-adamantyl(meth)acrylate and dialkyl(1-adamantyl)methyl(meth)acrylate; at least one repeating unit having a lactone structure; and at least one repeating unit having two or more hydroxyl groups.

9. The resist composition as claimed in claim 8, wherein the resin (B) further contains a repeating unit having a carboxyl group.

10. The resist composition as claimed in claim 1, wherein the resin (B) is a resin containing a repeating unit having an alcoholic hydroxyl group and capable of decomposing under the action of an acid to increase the solubility in an alkali developer.

11. The resist composition as claimed in claim 10, wherein the repeating unit having an alcoholic hydroxyl group in the resin (B) is a repeating unit having at least one member selected from a monohydroxyadamantane structure, a dihydroxyadamantane structure and a trihydroxyadamantane structure.

12. The resist composition as claimed in claim 1, wherein the resin (B) is a resin containing a repeating unit having a lactone structure.

13. The resist composition as claimed in claim 1, wherein the resin (B) is a resin containing at least one methacrylic acid ester repeating unit and at least one acrylic acid ester repeating unit.

14. The resist composition as claimed in claim 1, wherein the resin (B) has a fluorine atom in the main or side chain.

15. The resist composition as claimed in claim 1, wherein the resin (B) has a hexafluoro-2-propanol structure.

16. A pattern forming method comprising: forming a photosensitive film from the resist composition claimed in claim 1; and exposing and developing the photosensitive film.

17. The resist composition as claimed in claim 1, wherein $R^1$ represents an aryl group.

18. A resist composition comprising (A) a sulfonium salt represented by the following formula (I); (D) a resin soluble in an alkali developer; and (E) an acid crosslinking agent capable of crosslinking with said resin soluble in an alkali developer under the action of an acid:

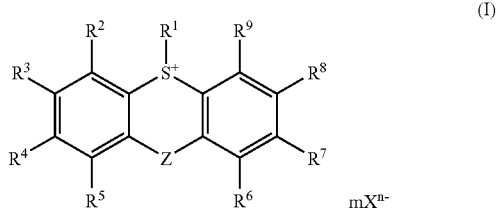

wherein $R^1$ represents an alkyl group or an aryl group, $R^2$ to $R^9$ each independently represents a hydrogen atom or a substituent and may combine with each other to form a ring, Z represents an electron-withdrawing divalent linking group,
$X^{n-}$ represents an n-valent organic anion,
n represents an integer of 1 to 3, and
m represents the number of anions necessary for neutralizing the electric charge;
and wherein the acid crosslinking agent (E) is selected from the group consisting of:
(1) phenol derivative acid crosslinking agents having a hydroxymethyl group, an alkoxymethyl group, or an acyloxymethyl group; and
(2) acid crosslinking agents having an N-hydroxymethyl group, an N-alkoxy-methyl group or an N-acyloxymethyl group.

19. A sulfonium compound represented by formula (II):

Formula (II):

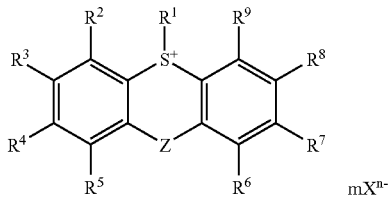

wherein
$R^1$ represents an aryl group,
$R^2$ to $R^9$ each independently represents a hydrogen atom or a substituent and may combine with each other to form a ring,
Z represents a sulfone group,
$X^{n-}$ represents an n-valent anion,
n represents an integer of 1 to 3, and
m represents the number of anions necessary for neutralizing the electric charge.

20. A sulfonium compound represented by formula (III):

Formula (III):

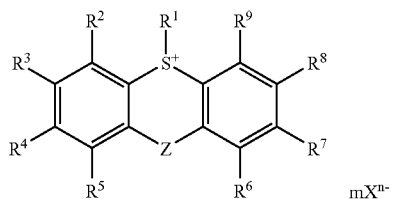

wherein
$R^1$ represents an alkyl group or an aryl group,
$R^2$ to $R^9$ each independently represents a hydrogen atom or a substituent and may combine with each other to form a ring, provided that at least one of $R^1$ to $R^9$ contains an alcoholic hydroxyl group,
Z represents an electron-withdrawing divalent linking group,
$X^{n-}$ represents an n-valent anion,
n represents an integer of 1 to 3, and
m represents the number of anions necessary for neutralizing the electric charge.

* * * * *